(12) United States Patent
Gurer et al.

(10) Patent No.: US 10,939,673 B2
(45) Date of Patent: *Mar. 9, 2021

(54) METHOD OF USING MOUSE HAVING A HUMANIZED CLUSTER OF DIFFERENTIATION 47 GENE

(71) Applicant: REGENERON PHARMACEUTICALS, INC., Tarrytown, NY (US)

(72) Inventors: Cagan Gurer, Chappaqua, NY (US); Ella Ioffe, Bronx, NY (US); Alexander Mujica, Elmsford, NY (US); Gavin Thurston, Briarcliff Manor, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/982,174

(22) Filed: May 17, 2018

(65) Prior Publication Data

US 2018/0249689 A1    Sep. 6, 2018

Related U.S. Application Data

(63) Continuation of application No. 14/951,825, filed on Nov. 25, 2015, now abandoned.

(60) Provisional application No. 62/087,992, filed on Dec. 5, 2014.

(51) Int. Cl.
| | |
|---|---|
| A01K 67/027 | (2006.01) |
| G01N 33/50 | (2006.01) |
| C07K 16/28 | (2006.01) |
| C07K 14/705 | (2006.01) |
| C07K 14/47 | (2006.01) |
| C12N 15/85 | (2006.01) |

(52) U.S. Cl.
CPC ...... *A01K 67/0278* (2013.01); *C07K 14/4703* (2013.01); *C07K 14/705* (2013.01); *C07K 14/70503* (2013.01); *C07K 14/70596* (2013.01); *C07K 16/2803* (2013.01); *C12N 15/8509* (2013.01); *G01N 33/5011* (2013.01); *G01N 33/5014* (2013.01); *G01N 33/5055* (2013.01); *G01N 33/5088* (2013.01); *A01K 2207/12* (2013.01); *A01K 2207/15* (2013.01); *A01K 2217/052* (2013.01); *A01K 2217/072* (2013.01); *A01K 2217/15* (2013.01); *A01K 2227/105* (2013.01); *A01K 2267/0331* (2013.01); *A01K 2267/0381* (2013.01); *C07K 2319/00* (2013.01); *C07K 2319/02* (2013.01); *G01N 2333/70596* (2013.01)

(58) Field of Classification Search
CPC .......... A01K 2217/052; A01K 67/0278; C07K 14/705
See application file for complete search history.

(56) References Cited

U.S. PATENT DOCUMENTS

| | | | |
|---|---|---|---|
| 6,586,251 B2 | 7/2003 | Economides et al. | |
| 7,294,754 B2 | 11/2007 | Poueymirou et al. | |
| 8,354,389 B2 | 1/2013 | Frendewey et al. | |
| 8,518,392 B2 | 8/2013 | Frendewey et al. | |
| 8,697,851 B2 | 4/2014 | Frendewey et al. | |
| 2007/0113297 A1* | 5/2007 | Yang | A01K 67/0271 800/17 |
| 2014/0369924 A1* | 12/2014 | Weissman | C07K 16/2887 424/1.49 |
| 2015/0106961 A1 | 4/2015 | Rojas et al. | |
| 2015/0143558 A1 | 5/2015 | McWhirter et al. | |
| 2015/0143559 A1 | 5/2015 | McWhirter et al. | |
| 2016/0345549 A1 | 12/2016 | Gurer et al. | |

FOREIGN PATENT DOCUMENTS

| | | | |
|---|---|---|---|
| CN | 101133083 A | 2/2008 | |
| CN | 101506235 A | 8/2009 | |
| RU | 2 425 880 C2 | 8/2011 | |
| WO | 2007/033221 A2 | 3/2007 | |
| WO | 2009/039244 A2 | 3/2009 | |
| WO | WO-2009039244 A2 * | 3/2009 | ........... C12Q 1/6883 |
| WO | 2011/044050 A2 | 4/2011 | |
| WO | 2012/112544 A2 | 8/2012 | |
| WO | 2013/056352 A1 | 4/2013 | |
| WO | 2013/063556 A1 | 5/2013 | |
| WO | WO-2013063556 A1 * | 5/2013 | |
| WO | 2013/144165 A1 | 10/2013 | |
| WO | WO-2013144165 A1 * | 10/2013 | |
| WO | 2013/192030 A2 | 12/2013 | |

(Continued)

OTHER PUBLICATIONS

Schickel Biochemistry and Cell Biology, 169-176, (Year: 2002).*

(Continued)

*Primary Examiner* — Anoop K Singh

(74) *Attorney, Agent, or Firm* — Scully, Scott, Murphy & Presser, P.C.; Elysa Goldberg

(57) ABSTRACT

Non-human animals, and methods and compositions for making and using the same, are provided, wherein said non-human animals comprise a humanization of an endogenous cluster of differentiation (CD) gene, in particular a humanization of a CD47 gene. Said non-human animals may be described, in some embodiments, as having a genetic modification to an endogenous CD47 gene so that said non-human animals express a CD47 polypeptide that includes a human portion and a non-human portion (e.g., a murine portion).

7 Claims, 9 Drawing Sheets

(9 of 9 Drawing Sheet(s) Filed in Color)

Specification includes a Sequence Listing.

(56) References Cited

FOREIGN PATENT DOCUMENTS

| WO | 2014/039782 A2 | 3/2014 |
|---|---|---|
| WO | 2014/071397 A2 | 5/2014 |
| WO | 2014/093678 A2 | 6/2014 |
| WO | 2015/042557 A1 | 3/2015 |
| WO | 2015/057758 A1 | 4/2015 |
| WO | 2015/077071 A1 | 5/2015 |
| WO | 2015/077072 A1 | 5/2015 |
| WO | 2015/171861 A1 | 11/2015 |
| WO | 2015/196051 A1 | 12/2015 |

OTHER PUBLICATIONS

Rebres et al the Journal of Bio. Chem., 34607-34616 (Year: 2001).*
Navarro-Alvarez et al. Cellular and Molecular Immunology, vol. 8, 285-288 (Year: 2011).*
Barclay et al Nature Review, 6, 457-464 (Year: 2006).*
Brooke et al. J. Innnnunol., vol. 173,2562-2570 (Year: 2004).*
Sano et al. Biochem. J., vol. 344, 667-675 (Year: 1999).*
Harari D. et al., "Bridging the Species Divide: Transgenic Mice Humanized for Type-I Interferon Response", PLoS ONE 9(1):e84259, XP055553720, DOI:10.1371/journal.pone.0084259 (Jan. 9, 2014).
Brevini T.A.L. et al., "No Shortcuts to Pig Embryonic Stem Cells", Theriogenology 74:544-550 (2010).
Cao S. et al., "Isolation and Culture of Primary Bovine Embryonic Stem Cell Colonies by a Novel Method", Journal of Experimental Zoology 311A:368-376 (2009).
Dennis Jr. M.B., "Welfare Issues of Genetically Modified Animals", ILAR Journal 43(2):100-109 (2002).
Frankel A.E. et al., "Characterization of Diphtheria Fusion Proteins Targeted to the Human Interleukin-3 Receptor", Protein Engineering 13(8):575-581 (2000).
Glick B. et al., Moleculyarnaya Biotehnologiya. Printsipy i primeneniye. Moscow: Mir, 2002, together with an English-language translation.
Hofker M.H. et al., "Transgenic Mouse Methods and Protocols", Methods in Molecular Biology 209:51-67 (2002-2003).
Houdebine L-M, "Methods to Generate Transgenic Animals", Genetic Engineering in Livestock, New Applications and Interdisciplinary Perspectives, Engelhard M. et al., XVI, 1 46, p. 8, illu. pp. 31-47 (2009).
Pakula A.A., "Genetic Analysis of Protein Stability and Function", Annu. Rev. Genet. 23:289-310 (1989).
Paris D.B.B.P. et al., "Equine Embryos and Embryonic Stem Cells: Defining Reliable Markers of Pluripotency", Theriogenology 74:516-524 (2010).
Rybchin V.N., "Fundamentals of Genetic Engineering", Textbook for High Schools, Saint-Petersburg, Publishing House SPbSTU 522:411-413 (2002).
Zhou H. et al., "Developing tTA Transgenic Rats for Inducible and Reversible Gene Expression", International Journal of Biological Sciences 5(2):171-181 (2009).
Russian Office Action and Search Report dated Jun. 3, 2019 received in Russian Patent Application No. 2017123357, together with an English-language translation.
Willinger T. et al., "Improving Human Hemato-Lymphoid-System Mice by Cytokine Knock-in Gene Replacement", Trends in Immunology 32(7):321-327 (Jul. 2011).
Willinger T. et al., "Human IL-3/GM-CSF Knock-In Mice Support Human Alveolar Macrophage Development and Human Immune Responses in the Lung", PNAS 108(6)2390-2395 (Feb. 8, 2011).
Database Accession No. HQ585874, XP-002753825 (2 pages) (Nov. 19, 2010).
Database Accession No. Q08722, XP-002753826 (7 pages) (Nov. 1995).
Database Accession No. E5Q371, XP-002753827 (2 pages) (Feb. 8, 2011).
International Search Report and Written Opinion dated Feb. 26, 2016 received in International Application No. PCT/US2015/062614.

Anderson P., "Post-Transcriptional Control of Cytokine Production", Nature Immunology 9(4):353-359 (Apr. 2008).
Barclay A.N. et al., "The SIRP Family of Receptors and Immune Regulation", Nature Reviews-Immunology 6:457-464 (Jun. 2006).
Brooke G. et al., "Human Lymphocytes Interact Directly With CD47 Through a Novel Member of the Signal Regulatory Protein (SIRP) Family", The Journal of Immunology 173:2562-2570 (2004).
Bruce L.J. et al., "A Band 3-Based Macrocomplex of Integral and Peripheral Proteins in the RBC Membrane", Blood 101(10):4180-4188 (May 15, 2003).
Chang H.P. et al., "Impaired Memory Retention and Decreased Long-Term Potentiation in Integrin-Associated Protein-Deficient Mice", Learning & Memory 6:448-457 (1999).
Chao M P et al., "The CD47-SIRPα Pathway in Cancer Immune Evasion and Potential Therapeutic Implications", Current Opinion in Immunology 24:225-232 (2012).
Clark J. et al., "A Future for Transgenic Livestock", Nature Reviews-Genetics 4:825-833 (Oct. 2003).
Devoy A. et al., "Genomically Humanized Mice: Technologies and Promises", Nature Reviews-Genetics 13:14-20 (Jan. 2012).
Gama Sosa M.A. et al., "Animal Transgenesis: An Overview", Brain Struct Funct 214:91-109 (2010).
Gimeno R. et al., "Monitoring the Effect of Gene Silencing by RNA Interference in Human CD34+ Cells Injected into Newborn RAG2-/-γc -/- Mice: Functional Inactivation of p53 in Development T Cells", Blood 104(13):3886-3893 (Dec. 15, 2004).
Johansen M.L. et al., "Dual Regulation of SIRPα Phosphorylation by Integrins and CD47", The Journal of Biological Chemistry 282(33):24219-24230 (Aug. 17, 2007).
Koshimizu H. et al., "Comprehensive Behavioral Analysis of Cluster of Differentiation 47 Knockout Mice", PLOS One 9(2):e89584 (Feb. 2014).
Lavender K.J. et al., "Production of Bone Marrow, Liver, Thymus (BLT) Humanized Mice on the C57BL/6 Rag2-/-γc -/-CD47-/-Background", Journal of Immunological Methods 407:127-134 (2014).
Lavender K.J. et al., "BLT-Humanized C57BL/6 Rag2-/- γc -/-CD47-/- Mice are Resistant to GVHD and Develop B- and T-Cell Immunity to HIV Infection", Blood 122(25):4013-4020 (Dec. 12, 2013).
Legrand N. et al., "Transient Accumulation of Human Mature Thymocytes and Regulatory T Cells with CD28 Superagonist in "Human Immune System" Rag2-/- γc -/- Mice", Blood 108(1):238-245 (Jul. 1, 2006).
Lindberg F.P. et al., "Decreased Resistance to Bacterial Infection and Granulocyte Defects in IAP-Deficient Mice", Science 274:795-798 (Nov. 1, 1996).
Muñoz M. et al., "Constraints to Progress in Embryonic Stem Cells from Domestic Species", Stem Cell Rev and Resp 5:6-9 (2009).
Mouro-Chanteloup I. et al., "Normal Red Cell Membrane Expression of Rh and Rhag Polypeptides in CD47-Deficient Mice", Vox Sanguinis 78:P030 (Jul. 2000).
Mouro-Chanteloup I. et al., "Evidence that the Red Cell Skeleton Protein 4.2 Interacts with the Rh Membrane Complex Member CD47", Blood 101(1):338-344 (Jan. 1, 2003).
Navarro-Alvarez N. et al., "CD47: A New Player in Phagocytosis and Xenograft Rejection", Cellular & Molecular Immunology 8:285-288 (2011).
Niemann H. et al., "Transgenic Farm Animals: Present and Future", Rev Sci. Techn. Off. Int. Epiz. 24(1):285-298 (2005).
Oldenborg P-A et al., "Role of CD47 as a Marker of Self on Red Blood Cells", Science 288:2051-2054 (Jun. 16, 2000).
Pan Y. et al., "Studying the Mechanism of CD47-SIRPa Interactions on Red Blood Cells by Single Molecule Force Spectroscopy", Nanoscale 6:9951-9964 (2014).
Prelle K. et al., "Pluripotent Stem Cells—Model of Embryonic Development, Tool for Gene Targeting, and Basis of Cell Therapy", Anat Histo Embryol. 31(3):169-186 (Jun. 2002).
Poueymirou W.T. et al., "F0 Generation Mice Fully Derived from Gene-Targeted Embryonic Stem Cells Allowing Immediate Phenotypic Analyses", Nature Biotechnology 25(1):91-99 (Jan. 2007).
Rebres R.A. et al., "Normal Ligand Binding and Signaling by CD47 (Integrin-Associated Protein) Requires a Long Range Disulfide

(56) References Cited

OTHER PUBLICATIONS

Bond Between the Extracellular and Membrane-Spanning Domains", The Journal of Biological Chemistry 276(37):34607-34616 (Sep. 14, 2001).

Reinhold M.I. et al., "In Vivo Expression of Alternatively Spliced Forms of Integrin-Associated Protein (CD47)", Journal of Cell Sciences 108:3419-3425 (1995).

Rendtlew J.M. et al., "Dysregulation of CD47 and the Ligands Thrombospondin 1 and 2 in Multiple Myeloma", British Journal of Maematology 138:756-760 (2007).

Ristevski S., "Making Better Transgenic Models", Molecular Biotechnology 29:153-163 (2005).

Rongvaux A. et al., "Human Thrombopoietin Knockin Mice Efficiently Support Human Hematopoiesis In Vivo", PNAS 108(6):2378-2383 (Feb. 8, 2011).

Sano S-I et al., "Gene Structure of Mouse BIT/SHPS-1", Biochem. J. 344:667-675 (1999).

Schickel J. et al., "Gene for Integrin-Associated Protein (IAP, CD47): Physical Mapping, Genomic Structure, and Expression Studies in Skeletal Muscle", Biochem. Cell Biol. 80:169-176 (2002).

Shultz L.D. et al., "Humanized Mice for Immune System Investigation: Progress, Promise and Challenges", Nature Reviews-Immunology 12:786-798 (Nov. 2012).

Sick E. et al., "CD47 Updated: A Multifaceted Actor in the Tumour Microenvironment of Potential Therapeutic Interest", British Journal of Pharmacology 167:1415-1430 (2012).

Sigmund C.D., "Viewpoint: Are Studies in Genetically Altered Mice Out of Control?", Arterioscler Thromb Vasc Biol. 20:1425-1429 (2000).

Smith K.R., "Gene Transfer in Higher Animals: Theoretical Considerations and Key Concepts", Journal of Biotechnology 99:1-22 (2002).

Takenaka K. et al., "Polymorphism in Sirpa Modulates Engraftment of Human Hematopoietic Stem Cells", Nature Immunology 8(12):1313-1323 (Dec. 2007).

Tena A. et al., "Transgenic Expression of Human CD47 Markedly Increases Engraftment in a Murine Model of Pig-to-Human Hematopoietic Cell Transplantation", American Journal of Transplantation 14:2713-2722 (2014).

Tena A. et al., "Miniature Swine Expressing Human CD47 to Enhance Bone Marrow Engraftment in Non-Human Primates", Supplement to Transplantation 94(10S):776 (Nov. 27, 2012).

Teraoka Y. et al., "Expression of Recipient CD47 on Rat Insulinoma Cell Xenografts Prevents Macrophage-Mediated Rejection Through SIRPa Inhibitory Signaling in Mice", PLOS One 8(3):e58359 (Mar. 2013).

Traggiai E. et al., "Development of a Human Adaptive Immune System in Cord Blood Cell-Transplanted Mice", Science 304:104-107 (Apr. 2, 2004).

Tseng D. et al., "Anti-CD47 Antibody-Mediated Phagocytosis of Cancer by Macrophages Primes an Effective Antitumor T-Cell Response", PNAS 110(27):11103-11108 (Jul. 2, 2013).

Tulasne D. et al., "C-Terminal Peptide of Thrombospondin-1 Induces Platelet Aggregation Through the Fc Receptor γ-Chain-Associated Signaling Pathway and by Agglutination", Blood 98(12):3346-3352 (Dec. 1, 2001).

Valenzuela D.M. et al., "High-Throughput Engineering of the Mouse Genome Coupled with High-Resolution Expression Analysis", Nature Biotechnology 21(6):652-659 (Jun. 2003).

Verdrengh M. et al., "Integrin-Associated Protein (IAP)-Deficient Mice are Less Susceptible to Development *Staphylococcus aureus*-Induced Arthritis", Microbes and Infection 1:745-751 (1999).

Waern J.M. et al., "Ectopic Expression of Murine CD47 Minimizes Macrophage Rejection of Human Hepatocyte Xenografts in Immunodeficient Mice", Hepatology 56:1479-1488 (Oct. 2012).

Wang C. et al., "Human CD47 Expression Permits Survival of Porcine Cells in Immunodeficient Mice that Express SIRPα Capable of Binding to Human CD47", Cell Transplantation 20:1915-1920 (2011).

Wang H. et al., "Lack of CD47 on Nonhematopoietic Cells Induces Split Macrophage Tolerance to CD47null Cells", PNAS 104(34):13744-13749 (Aug. 21, 2007).

Wang X-Q et al., "Integrin-Associated Protein Stimulates α2β1-Dependent Chemotaxis Via Gi-Mediated Inhibition of Adenylate Cyclase and Extracellular-Regulated Kinases", The Journal of Cell Biology 147(2):389-399 (Oct. 18, 1999).

Wheeler M.B. et al., "Transgenic Technology and Applications in Swine", Theriogenology 56:1345-1369 (2001).

Chinese Office Action dated Mar. 3, 2020 received in Chinese Patent Application No. 201580066047.0, together with an English-language translation.

\* cited by examiner

SEQUENCE LISTING

<160> NUMBER OF SEQ ID NOS: 36

<210> SEQ ID NO 1
<211> LENGTH: 5591
<212> TYPE: DNA
<213> ORGANISM: Mus musculus

<400> SEQUENCE: 1

```
gcctacaccg ggagagcagg gaggaggagt tggactgagg ttgggcggct ccgaggtcca        60
gggcgagctt ggccagaggg agtagagagc agcggggctg cgcagggacg cgtgccgtga       120
gttccggtga gcgtgtgtgt cccatgctcc cgtctttcag gccggcccag gacacgaagc       180
cggaagagag ctggctggag ggacgggggc cgtgagcaga gagtgcaacc cgcgcagccc       240
cggggacagg ctgattcttg gcgctctccg ccggagcctg cccagggctg ggtgtgaggc       300
tggcgtcacg tcaacgagca gaggcggcca ggcggggcgg agtgcgcgtg cgcggggcgg       360
cgagcacgcg cgcgcgcgca cccccgggca gcctgggcgg ccgctcctgc ctgtcactgc       420
tgcggcgctg ctggtcggtc gtttcccttg aaggcagcag cggaggcggc ggctgctcca       480
gacacctgcg gcggcgaccc cccggcggcg cggagatgtg gcccttggcg gcggcgctgt       540
tgctgggctc ctgctgctgc ggttcagctc aactactgtt tagtaacgtc aactccatag       600
agttcacttc atgcaatgaa actgtggtca tcccttgcat cgtccgtaat gtggaggcgc       660
aaagcaccga agaaatgttt gtgaagtgga agttgaacaa atcgtatatt ttcatctatg       720
atggaaataa aaatagcact actacagatc aaaacttta cagtgcaaaa atctcagtct       780
cagacttaat caatggcatt gcctctttga aaatggataa gcgcgatgcc atggtgggaa       840
actacacttg cgaagtgaca gagttatcca gagaaggcaa aacagttata gagctgaaaa       900
accgcacggc cttcaacact gaccaaggat cagcctgttc ttacgaggag gagaaaggag       960
gttgcaaatt agtttcgtgg ttttctccaa atgaaaagat cctcattgtt attttcccaa      1020
ttttggctat actcctgttc tggggaaagt ttggtatttt aacactcaaa tataaatcca      1080
```

-continued

```
gccatacgaa taagagaatc attctgctgc tcgttgccgg gctggtgctc acagtcatcg    1140
tggttgttgg agccatcctt ctcatcccag gagaaaagcc cgtgaagaat gcttctggac    1200
ttggcctcat tgtaatctct acggggatat taatactact tcagtacaat gtgtttatga    1260
cagcttttgg aatgacctct ttcaccattg ccatattgat cactcaagtg ctgggctacg    1320
tccttgcttt ggtcgggctg tgtctctgca tcatggcatg tgagccagtg cacggccccc    1380
ttttgatttc aggtttgggg atcatagctc tagcagaact acttggatta gtttatatga    1440
agtttgtcga ataggtgaag ggaagtgacg gactgtaact tggaagtcag aaatggaaga    1500
atacagttgt ctaagcacca ggtcttcacg actcacagct ggaaggaaca dacaacagta    1560
actgacttcc atccaggaaa acatgtcaca taaatgatta ctaagtttat attcaaagca    1620 gctgtactt  acataataaa aaaaatatga tgtgctgtgt aaccaattgg aatcccattt    1680
ttctattgtt tctactcaac tagggcaaaa cgtttcaggg gcaacttcca agaatgatgc    1740
ttgttagatc ctagagtctc tgaacactga gtttaaattg attccgagtg agactcgcca    1800
agcactaacc tgagggttag ttacccagag atacctatga aaaacagtgg tatccagcaa    1860
gccttagtaa actcaggttg ccagcagctt tgccacttcc gctgctagct gaataacaag    1920
actgccactt ctgggtcata gtgatagaga ctgaagtaga aaaacgaatg tggttgggca    1980
aatcccgtgt ggcccctctg tgtgctatga tattgatggc actggtgtct tcattcttgg    2040
gggttgccat cattcacaca cacccctttg acatacagtg cacccagtt ttgaatacat    2100 ttttttttgca ccctgtcccg ttctgctact ttgatttgcg ttatgatata tatatatata    2160
tataatacct tttctcctct ttaaacatgg tcctgtgaca caatagtcag ttgcagaaag    2220
gagccagact tattcgcaaa gcactgtgct caaactcttc agaaaaaaag gaaaaaaaaa    2280
aaaagctata gttgtaacat atgtattcca gacctctggt ttaaaggcaa aagaaaaaaa    2340
atctacagtg tttcttctca tgttttctga tcggaggcat gacaaagcaa gactgaaatc    2400
tgaactgtgt ctcctgcatg gcaacacgtg tctccgtcag gccctcgcaa ggcccgggga    2460
gggggttcta cgcctcttgt ctctttgttg catgctgaac actcatcgcc ttcctactgt    2520
atcctgcctc ctgcagcctc cctcttcctc ctccctcttcc tcttcctcct cttcctcctc    2580
ctcctcctct tcctccaagt tgaaaggtc aaacaaaact accacattcc ctacccagtt    2640
agaagaaaac caccgtcctg acagttgtga tcgcatggag tactttaga ttattagcac    2700 ctgtttttac ctcgtttgtg ggcgtgtttg tatgtgcaca tgtatgaagt cggcacatgc    2760
accttctgta tgggcagagg cgtggcatct acagaagagc agatgccaac tttgtgcttt    2820
tagtgaatac attaaaaaaa aaaaaccaac ggtccttatt gagtggaatt ctatttgatg    2880
caaatatttg agctctttaa gactttaaaa ctagataatg tgccaagctt ttaggactgc    2940
tcaccagtgc cctctgaaga aacaccagta cttttttcctg tttgtgtaat aaaggcatat    3000
ttgtatttgt gtttgcatca ctaatggtta tttcttctta gtccactgaa tgttccatg    3060 tgcctctcgt atgccaaact ttttgtcatc tttcatgtgg ggaccaaatg gtttgtctgt    3120
ggcaaaccta aacctatgac ctgctgaggc ctctcagaaa actgaccaca gtaccaagat    3180
agtacttcgc aaagaaaagt aggttccctc cctggttttg tagctgtcgc caatattagc    3240
gtaattccaa ggagctgaac gcctttatat aaatctgatg gcacctgatg cttttagttc    3300
tgaaaatatt tacactcgga tcatgttgtt gatgacttaa acaaagtttt gatgaagaga    3360
gcaaaaaaaa agcaggtgga tttggaacag tttcagggtt tttttgttt  ttgtttttt     3420 gttttttgttt tttttttttt attttgtttt ttctgttctc tgttagaaaa gtcaggtgtt    3480
```

```
ctctgtcagg ctatctttat agtcaatttt ttttacgaac taaagtagta cctttaata    3540
tgtagtcaac gccctctgc tcggggttca gttttgggtc ttaaccagct gtcatgttct    3600
ctatgctgcc tgccacttga ggcactgagt gccctagaca gtcccatcgg tggtagccag    3660
ggaaacgaaa gacgaactca actcttgctc ctaataatca actctctgta tgaaggatgg    3720
cagcattaag agtcctcctg cctgggcatt attgggccag ttcaccctct ttaaatcaaa    3780
cccgcagtgg ctcccagttc tcgtcccatc agatttaaat tgctaacagt atggggggca    3840
ccacgcatct gttttgtccc acaatgcgct tttctctccc aaatcccgat ttctgctgtc    3900
atagcctcta ttcaatttt atttattgtc tgccctccac ttatacaatc gtagagagca    3960
atgccatttg tcactttctg caacagtttt ttgagccttt atggctgaat cccatttttc    4020
ttctctttca aactgtttgc tccattgctc ctcccgcacg gctgtccgta cagtcatccc    4080
atccatctgg gggcctcttt catctctcac ccttcctggt gcttcgtgga tctctgctta    4140
cctctgtggg tttttttttt ttttttttgac ttattcttct cactggactt taagattact    4200
tccacagcga aagtgctgcc tccctttct gcccgcagtg ttctgcgtac tttagatact    4260
actcagtgct gacatttgat ggcaaaagtt gcctgcactt aaatttctct ttttaatagg    4320
gtgaactaga gttggagttt ttttctcttt tttctctttt ctctctctct ctctctctct    4380
ctctctctct ctctctctct ctccctccct cctccctcc ctccctccct ccctctctct    4440
ctcttttct ttctttcttt ctttctttct ttctttcttt ctttctttct tctttcttt     4500
ttttgacaaa tctcacaggc tttgagaatt ataaaaggtg acagttcacc tgaaaatcac    4560
aggtctggtc tgtttaaatt gttgagaaat atccgattaa aagtcttgtg gctgtgtcct    4620
aataggctct ctttcaggac gttgtagtca atagagtggc tgaaccatac ttgagtttat    4680
aaagctcaaa aactgatgca cccactctgc tattatcgtg ttagtaagag ttcagctgta    4740
tatcattgtc taggtttatc ttgtcctaca gtgggtattc aaatatggcc accagaggat    4800
atgtgtaaat ataagcacct gtatttgcct gttgttgaga actggaggga aaacaaaaaa    4860
tgtctggcaa ccctttgcct tttaaccgt aattaattga cagtttattt agagataaga    4920
gttttcaaaa atctcttaac tgccacaacc cacagagggt cttgttttgc catcttcagt    4980
ggctcacaga tatgatccaa gttaacttga aagagatgag cagtacccag gaaattgtcc    5040
tgcctttaac tctggctgtc cttaattatg actgtttaat gctgaatttt ccatccgtct    5100
agtgtttgag ggtaaagaaa agcctttttt aaataagtat ttctgtaaaa cggcatcggt    5160
gggatcttct gtgttgctat cacgggtgaa agagggaaac atttcttatt tttattaagc    5220
agagcattat ttacagaaag ccattgttga gaattagttc ccacatcata taaatatcca    5280
ttaaccattc taaattgtaa gagaactcca gtgttgctat gcacaaggaa ctctcctggg    5340
ggcctttttt tgcatagcaa ttaaaggtat gctatttgtc agtagccatt ttttgcagtg    5400
atttaaagac caaagttgtt ttacagctgt gttacccta aaggttttt tttatgtat      5460
taaatcaatt tatcactgtt tgaagctttg aatacctgca atctttgcca agatacttt     5520
ttatttaaaa aaataactgt gtaaatatta ccctgtaata ttatatatac ttaataaaac    5580
attttaagct a                                                        5591

<210> SEQ ID NO 2
<211> LENGTH: 312
<212> TYPE: PRT
<213> ORGANISM: Mus musculus
```

<400> SEQUENCE: 2

```
Met Trp Pro Leu Ala Ala Ala Leu Leu Leu Gly Ser Cys Cys Cys Gly
1               5                   10                  15

Ser Ala Gln Leu Leu Phe Ser Asn Val Asn Ser Ile Glu Phe Thr Ser
            20                  25                  30

Cys Asn Glu Thr Val Val Ile Pro Cys Ile Val Arg Asn Val Glu Ala
        35                  40                  45

Gln Ser Thr Glu Glu Met Phe Val Lys Trp Lys Leu Asn Lys Ser Tyr
    50                  55                  60

Ile Phe Ile Tyr Asp Gly Asn Lys Asn Ser Thr Thr Asp Gln Asn
65                  70                  75                  80

Phe Thr Ser Ala Lys Ile Ser Val Ser Asp Leu Ile Asn Gly Ile Ala
                85                  90                  95

Ser Leu Lys Met Asp Lys Arg Asp Ala Met Val Gly Asn Tyr Thr Cys
            100                 105                 110

Glu Val Thr Glu Leu Ser Arg Glu Gly Lys Thr Val Ile Glu Leu Lys
        115                 120                 125

Asn Arg Thr Ala Phe Asn Thr Asp Gln Gly Ser Ala Cys Ser Tyr Glu
130                 135                 140

Glu Glu Lys Gly Gly Cys Lys Leu Val Ser Trp Phe Ser Pro Asn Glu
145                 150                 155                 160

Lys Ile Leu Ile Val Ile Phe Pro Ile Leu Ala Ile Leu Leu Phe Trp
                165                 170                 175

Gly Lys Phe Gly Ile Leu Thr Leu Lys Tyr Lys Ser Ser His Thr Asn
            180                 185                 190

Lys Arg Ile Ile Leu Leu Leu Val Ala Gly Leu Val Leu Thr Val Ile
        195                 200                 205

Val Val Val Gly Ala Ile Leu Leu Ile Pro Gly Glu Lys Pro Val Lys
    210                 215                 220

Asn Ala Ser Gly Leu Gly Leu Ile Val Ile Ser Thr Gly Ile Leu Ile
225                 230                 235                 240

Leu Leu Gln Tyr Asn Val Phe Met Thr Ala Phe Gly Met Thr Ser Phe
                245                 250                 255

Thr Ile Ala Ile Leu Ile Thr Gln Val Leu Gly Tyr Val Leu Ala Leu
            260                 265                 270

Val Gly Leu Cys Leu Cys Ile Met Ala Cys Glu Pro Val His Gly Pro
        275                 280                 285

Leu Leu Ile Ser Gly Leu Gly Ile Ile Ala Leu Ala Glu Leu Leu Gly
    290                 295                 300

Leu Val Tyr Met Lys Phe Val Glu
305                 310
```

<210> SEQ ID NO 3
<211> LENGTH: 5560
<212> TYPE: DNA
<213> ORGANISM: Mus musculus

<400> SEQUENCE: 3

| | | |
|---|---|---|
| gcctacaccg ggagagcagg gaggaggagt tggactgagg ttgggcggct ccgaggtcca | 60 |
| gggcgagctt ggccagaggg agtagagagc agcggggctg cgcagggacg cgtgccgtga | 120 |
| gttccggtga gcgtgtgtgt cccatgctcc cgtctttcag gccggcccag gacacgaagc | 180 |
| cggaagagag ctggctggag ggacgggggc cgtgagcaga gagtgcaacc cgcgcagccc | 240 |
| cggggacagg ctgattcttg gcgctctccg ccggagcctg cccagggctg ggtgtgaggc | 300 |

```
tggcgtcacg tcaacgagca gaggcggcca ggcggggcgg agtgcgcgtg cgcggggcgg    360
cgagcacgcg cgcgcgcgca cccccgggca gcctgggcgg ccgctcctgc ctgtcactgc    420
tgcggcgctg ctggtcggtc gtttcccttg aaggcagcag cggaggcggc ggctgctcca    480
gacacctgcg gcgcgaccc cccggcggcg cggagatgtg gcccttggcg gcggcgctgt     540
tgctgggctc ctgctgctgc ggttcagctc aactactgtt tagtaacgtc aactccatag    600
agttcacttc atgcaatgaa actgtggtca tcccttgcat cgtccgtaat gtggaggcgc    660
aaagcaccga agaaatgttt gtgaagtgga agttgaacaa atcgtatatt ttcatctatg    720
atggaaataa aaatagcact actacagatc aaaactttac cagtgcaaaa atctcagtct    780
cagacttaat caatggcatt gcctctttga aaatggataa gcgcgatgcc atggtgggaa    840
actacacttg cgaagtgaca gagttatcca gagaaggcaa aacagttata gagctgaaaa    900
accgcacggt tcgtggtttt ctccaaatg aaaagatcct cattgttatt tcccaatttt     960
tggctatact cctgttctgg ggaaagtttg gtattttaac actcaaatat aaatccagcc   1020
atacgaataa gagaatcatt ctgctgctcg ttgccgggct ggtgctcaca gtcatcgtgg   1080
ttgttggagc catccttctc atcccaggag aaaagcccgt gaagaatgct tctggacttg   1140
gcctcattgt aatctctacg gggatattaa tactacttca gtacaatgtg tttatgacag   1200
cttttggaat gacctctttc accattgcca tattgatcac tcaagtgctg gctacgtcc    1260
ttgctttggt cgggctgtgt ctctgcatca tggcatgtga gccagtgcac ggcccccttt   1320
tgatttcagg tttggggatc atagctctag cagaactact tggattagtt tatatgaagt   1380
ttgtcgcttc caaccagagg actatccaac ctcctaggaa taggtgaagg gaagtgacgg   1440
actgtaactt ggaagtcaga aatggaagaa tacagttgtc taagcaccag gtcttcacga   1500
ctcacagctg gaaggaacag acaacagtaa ctgacttcca tccaggaaaa catgtcacat   1560
aaatgattac taagttttata ttcaaagcag ctgtactta cataataaaa aaatatgat    1620
gtgctgtgta accaattgga atcccatttt tctattgttt ctactcaact aggggcaaac   1680
gtttcagggg caacttccaa gaatgatgct tgttagatcc tagagtctct gaacactgag   1740
tttaaattga ttccgagtga gactcgccaa gcactaacct gagggttagt tacccagaga   1800
tacctatgaa aaacagtggt atccagcaag ccttagtaaa ctcaggttgc agcagctttt   1860
gccacttccg ctgctagctg aataacaaga ctgccacttc tgggtcatag tgatagagac   1920
tgaagtagaa aaacgaatgt ggttgggcaa atcccgtgtg gcccctctgt gtgctatgat   1980
attgatggca ctggtgtctt cattcttggg ggttgccatc attcacacac accccttga    2040
catacagtgc acccccagttt tgaatacatt tttttttgcac cctgtcccgt tctgctactt  2100
tgatttgcgt tatgatatat atatatatat ataatacctt ttctcctctt taaacatggt   2160
cctgtgacac aatagtcagt tgcagaaagg agccagactt attcgcaaag cactgtgctc   2220
aaactcttca gaaaaaaagg aaaaaaaaaa aaagctatag ttgtaacata tgtattccag   2280
acctctggtt taaaggcaaa agaaaaaaaa tctacagtgt ttcttctcat gtttttctgat 2340
cggaggcatg acaaagcaag actgaaatct gaactgtgtc cctgcatgg caacacgtgt    2400
ctccgtcagg ccctcgcaag gcccggggag ggggttctac gcctcttgtc tctttgttgc   2460
atgctgaaca ctcatcgcct tcctactgta tcctgcctcc tgcagcctcc ctcttcctcc    2520
tcctcttcct cttcctcctc ttcctcctcc tcctcctctt cctccaagtt tgaaaggtca   2580
aacaaaacta ccacattccc tacccagtta gaagaaaacc accgtcctga cagttgtgat  2640
```

```
cgcatggagt actttagat tattagcacc tgttttacc tcgtttgtgg gcgtgtttgt    2700
atgtgcacat gtatgaagtc ggcacatgca ccttctgtat gggcagaggc gtggcatcta    2760
cagaagagca gatgccaact ttgtgctttt agtgaataca ttaaaaaaaa aaaaccaacg    2820
gtccttattg agtggaattc tatttgatgc aaatatttga gctctttaag actttaaaac    2880
tagataatgt gccaagcttt taggactgct caccagtgcc ctctgaagaa acaccagtac    2940
tttttcctgc ttgtgtaata aaggcatatt tgtatttgtg tttgcatcac taatggttat    3000
ttcttcttag tccactgaat gtttccatgt gcctctcgta tgccaaactt tttgtcatct    3060
ttcatgtggg gaccaaatgg tttgtctgtg gcaaacctaa acctatgacc tgctgaggcc    3120
tctcagaaaa ctgaccacag taccaagata gtacttcgca agaaaagta  ggttccctcc    3180
ctggttttgt agctgtcgcc aatattagcg taattccaag gagctgaacg cctttatata    3240
aatctgatgg cacctgatgc ttttagttct gaaaatattt acactcggat catgttgttg    3300
atgacttaaa caaagttttg atgaagagag caaaaaaaaa gcaggtggat ttggaacagt    3360
ttcagggttt ttttgtttt ttgttttttg ttttgtttt ttttttta ttttgtttt    3420
tctgttctct gttagaaaag tcaggtgttc tctgtcaggc tatctttata gtcaatttt    3480
tttacgaact aaagtagtac cttttaatat gtagtcaacg ccctctgct cggggttcag    3540
ttttgggtct taaccagctg tcatgttctc tatgctgcct gccacttgag gcactgagtg    3600
ccctagacag tcccatcggt ggtagccagg gaaacgaaag acgaactcaa ctcttgctcc    3660
taataatcaa ctctctgtat gaaggatggc agcattaaga gtcctcctgc ctgggcatta    3720
tgggccagt tcaccctctt taaatcaaac ccgcagtggc tcccagttct cgtcccatca    3780
gatttaaatt gctaacagta tggggggcac cacgcatctg ttttgtccca caatgcgctt    3840
ttctctccca aatcccgatt tctgctgtca tagcctctat tcaattttta tttattgtct    3900
gccctccact tatacaatcg tagagagcaa tgccatttgt cactttctgc aacagttttt    3960
tgagccttta tggctgaatc ccattttct tctctttcaa actgtttgct ccattgctcc    4020
tcccgcacgg ctgtccgtac agtcatccca tccatctggg ggcctctttc atctctcacc    4080
cttcctggtg cttcgtggat ctctgcttac ctctgtgggt tttttttt tttttgact    4140
tattcttctc actggacttt aagattactt ccacagcgaa agtgctgcct ccctttctg    4200
cccgcagtgt tctgcgtact ttagatacta ctcagtgctg acatttgatg gcaaagttg    4260
cctgcactta aattctctct tttaataggg tgaactagag ttggagtttt ttctctttt    4320
ttctcttttc tctctctctc tctctctctc tctctctctc tccctccctc    4380
cctcctccc tccctccctc cctctctctc tcttttcct tctttctttc tttctttctt    4440
tctttctttc tttctttctt tctttcttt tttgacaaat ctcacaggct ttgagaatta    4500
taaaaggtga cagttcacct gaaaatcaca ggtctggtct gtttaaattg ttgagaaata    4560
tccgattaaa agtcttgtgg ctgtgtccta ataggctctc tttcaggacg ttgtagtcaa    4620
tagagtggct gaaccatact tgagtttata aagctcaaaa actgatgcac ccactctgct    4680
attatcgtgt tagtaagagt tcagctgtat atcattgtct aggtttatct tgtcctacag    4740
tgggtattca aatatggcca ccagaggata tgtgtaaata taagcacctg tatttgcctg    4800
ttgttgagaa ctggagggaa aacaaaaaat gtctggcaac cctttgcctt tttaaccgta    4860
attaattgac agtttattta gagataagag ttttcaaaaa tctcttaact gccacaaccc    4920
acagagggtc ttgttttgcc atcttcagtg gctcacagat atgatccaag ttaacttgaa    4980
agagatgagc agtacccagg aaattgtcct gccttttaact ctggctgtcc ttaattatga    5040
```

```
ctgtttaatg ctgaattttc catccgtcta gtgtttgagg gtaaagaaaa gccttttttta    5100 aataagtatt tctgtaaaac ggcatcggtg ggatcttctg tgttgctatc acgggtgaaa    5160
gagggaaaca tttcttattt ttattaagca gagcattatt tacagaaagc cattgttgag    5220
aattagttcc cacatcatat aaatatccat taaccattct aaattgtaag agaactccag    5280
tgttgctatg cacaaggaac tctcctgggg ccttttttt gcatagcaat taaaggtatg     5340
ctatttgtca gtagccattt tttgcagtga tttaaagacc aaagttgttt tacagctgtg    5400
ttacccttaa aggttttttt tttatgtatt aaatcaattt atcactgttt gaagctttga    5460
atacctgcaa tctttgccaa gatacttttt tatttaaaaa aataactgtg taaatattac    5520
cctgtaatat tatatatact taataaaaca ttttaagcta                          5560
```

<210> SEQ ID NO 4
<211> LENGTH: 303
<212> TYPE: PRT
<213> ORGANISM: Mus musculus

<400> SEQUENCE: 4

```
Met Trp Pro Leu Ala Ala Ala Leu Leu Leu Gly Ser Cys Cys Cys Gly
1               5                   10                  15

Ser Ala Gln Leu Leu Phe Ser Asn Val Asn Ser Ile Glu Phe Thr Ser
            20                  25                  30

Cys Asn Glu Thr Val Val Ile Pro Cys Ile Val Arg Asn Val Glu Ala
        35                  40                  45

Gln Ser Thr Glu Glu Met Phe Val Lys Trp Lys Leu Asn Lys Ser Tyr
    50                  55                  60

Ile Phe Ile Tyr Asp Gly Asn Lys Asn Ser Thr Thr Thr Asp Gln Asn
65                  70                  75                  80

Phe Thr Ser Ala Lys Ile Ser Val Ser Asp Leu Ile Asn Gly Ile Ala
                85                  90                  95

Ser Leu Lys Met Asp Lys Arg Asp Ala Met Val Gly Asn Tyr Thr Cys
            100                 105                 110

Glu Val Thr Glu Leu Ser Arg Glu Gly Lys Thr Val Ile Glu Leu Lys
        115                 120                 125

Asn Arg Thr Val Ser Trp Phe Ser Pro Asn Glu Lys Ile Leu Ile Val
    130                 135                 140

Ile Phe Pro Ile Leu Ala Ile Leu Leu Phe Trp Gly Lys Phe Gly Ile
145                 150                 155                 160

Leu Thr Leu Lys Tyr Lys Ser Ser His Thr Asn Lys Arg Ile Ile Leu
                165                 170                 175

Leu Leu Val Ala Gly Leu Val Leu Thr Val Ile Val Val Gly Ala
            180                 185                 190

Ile Leu Leu Ile Pro Gly Glu Lys Pro Val Lys Asn Ala Ser Gly Leu
        195                 200                 205

Gly Leu Ile Val Ile Ser Thr Gly Ile Leu Ile Leu Gln Tyr Asn
    210                 215                 220

Val Phe Met Thr Ala Phe Gly Met Thr Ser Phe Thr Ile Ala Ile Leu
225                 230                 235                 240

Ile Thr Gln Val Leu Gly Tyr Val Leu Ala Leu Val Gly Leu Cys Leu
                245                 250                 255

Cys Ile Met Ala Cys Glu Pro Val His Gly Pro Leu Leu Ile Ser Gly
            260                 265                 270

Leu Gly Ile Ile Ala Leu Ala Glu Leu Leu Gly Leu Val Tyr Met Lys
```

```
          275                 280                 285
Phe Val Ala Ser Asn Gln Arg Thr Ile Gln Pro Pro Arg Asn Arg
   290                 295                 300

<210> SEQ ID NO 5
<211> LENGTH: 5648
<212> TYPE: DNA
<213> ORGANISM: Mus musculus

<400> SEQUENCE: 5
gcctacaccg ggagagcagg gaggaggagt tggactgagg ttgggcggct ccgaggtcca      60
gggcgagctt ggccagaggg agtagagagc agcggggctg cgcagggacg cgtgccgtga     120
gttccggtga gcgtgtgtgt cccatgctcc cgtctttcag gccggcccag gacacgaagc     180
cggaagagag ctggctggag ggacgggggc cgtgagcaga gagtgcaacc cgcgcagccc     240
cggggacagg ctgattcttg gcgctctccg ccggagcctg cccagggctg ggtgtgaggc     300
tggcgtcacg tcaacgagca gaggcggcca ggcggggcgg agtgcgcgtg cgcggggcgg     360
cgagcacgcg cgcgcgcgca ccccgggca  gcctgggcgg ccgctcctgc ctgtcactgc     420
tgcggcgctg ctggtcggtc gtttcccttg aaggcagcag cggaggcggc ggctgctcca     480
gacacctgcg gcggcgaccc cccggcggcg cggagatgtg gcccttggcg gcggcgctgt     540
tgctgggctc ctgctgctgc ggttcagctc aactactgtt tagtaacgtc aactccatag     600
agttcacttc atgcaatgaa actgtggtca tcccttgcat cgtccgtaat gtggaggcgc     660
aaagcaccga agaaatgttt gtgaagtgga agttgaacaa atcgtatatt ttcatctatg     720
atggaaataa aaatagcact actacagatc aaaactttac cagtgcaaaa atctcagtct     780
cagacttaat caatggcatt gcctctttga aaatggataa gcgcgatgcc atggtgggaa     840
actacacttg cgaagtgaca gagttatcca gagaaggcaa aacagttata gagctgaaaa     900
accgcacggc cttcaacact gaccaaggat cagcctgttc ttacgaggag gagaaaggag     960
gttgcaaatt agtttcgtgg tttctccaa  atgaaaagat cctcattgtt attttcccaa    1020
ttttggctat actcctgttc tggggaaagt ttggtatttt aacactcaaa tataaatcca    1080
gccatacgaa taagagaatc attctgctgc tcgttgccgg gctggtgctc acagtcatcg    1140
tggttgttgg agccatcctt ctcatcccag gagaaaagcc cgtgaagaat gcttctggac    1200
ttggcctcat tgtaatctct acggggatat taatactact tcagtacaat gtgtttatga    1260
cagcttttgg aatgacctct ttcaccattg ccatattgat cactcaagtg ctgggctacg    1320
tccttgcttt ggtcgggctg tgtctctgca tcatggcatg tgagccagtg cacggccccc    1380
ttttgatttc aggtttgggg atcatagctc tagcagaact acttggatta gtttatatga    1440
gtttgtcgc  ttccaaccag aggactatcc aacctcctag gaaagctgta gaggaacccc    1500
ttaacgaata ggtgaaggga agtgacggac tgtaacttgg aagtcagaaa tggaagaata    1560
cagttgtcta agcaccaggt cttcacgact cacagctgga aggaacagac aacagtaact    1620
gacttccatc caggaaaaca tgtcacataa atgattacta agtttatatt caaagcagct    1680
gtactttaca taataaaaaa aatatgatgt gctgtgtaac caattggaat cccattttc     1740
tattgtttct actcaactag gggcaaacgt ttcaggggca acttccaaga atgatgcttg    1800
ttagatccta gagtctctga acactgagtt taaattgatt ccgagtgaga ctcgccaagc    1860
actaacctga gggttagtta cccagagata cctatgaaaa acagtggtat ccagcaagcc    1920
ttagtaaact caggttgcca gcagctttgc cacttccgct gctagctgaa taacaagact    1980
```

```
gccacttctg ggtcatagtg atagagactg aagtagaaaa acgaatgtgg ttgggcaaat    2040
cccgtgtggc ccctctgtgt gctatgatat tgatggcact ggtgtcttca ttcttggggg    2100
ttgccatcat tcacacacac ccctttgaca tacagtgcac cccagttttg aatacatttt    2160
ttttgcaccc tgtcccgttc tgctacttg atttgcgtta tgatatatat atatatatat    2220
aatacctttt ctcctctta aacatggtcc tgtgacacaa tagtcagttg cagaaaggag    2280
ccagacttat tcgcaaagca ctgtgctcaa actcttcaga aaaaaggaa aaaaaaaaa    2340 agctatagtt gtaacatatg tattccagac ctctggttta aaggcaaaag aaaaaaaatc    2400
tacagtgttt cttctcatgt tttctgatcg gaggcatgac aaagcaagac tgaaatctga    2460
actgtgtctc ctgcatggca acacgtgtct ccgtcaggcc ctcgcaaggc ccggggaggg    2520
ggttctacgc ctcttgtctc tttgttgcat gctgaacact catcgccttc ctactgtatc    2580
ctgcctcctg cagcctccct cttcctcctc tcttcctct tcctcctctt cctcctcctc    2640
ctcctcttcc tccaagtttg aaaggtcaaa caaaactacc acattcccta cccagttaga    2700
agaaaaccac cgtcctgaca gttgtgatcg catggagtac ttttagatta ttagcacctg    2760
tttttacctc gtttgtgggc gtgtttgtat gtgcacatgt atgaagtcgg cacatgcacc    2820
ttctgtatgg gcagaggcgt ggcatctaca gaagagcaga tgccaacttt gtgcttttag    2880
tgaatacatt aaaaaaaaaa aaccaacggt ccttattgag tggaattcta tttgatgcaa    2940
atatttgagc tctttaagac tttaaaacta gataatgtgc caagctttta ggactgctca    3000
ccagtgccct ctgaagaaac accagtactt tttcctgttt gtgtaataaa ggcatatttg    3060
tatttgtgtt tgcatcacta atggttattt cttcttagtc cactgaatgt ttccatgtgc    3120
ctctcgtatg ccaaactttt tgtcatcttt catgtgggga ccaaatggtt tgtctgtggc    3180
aaacctaaac ctatgacctg ctgaggcctc tcagaaaact gaccacagta ccaagatagt    3240
acttcgcaaa gaaaagtagg ttccctccct ggttttgtag ctgtcgccaa tattagcgta    3300
attccaagga gctgaacgcc tttatataaa tctgatggca cctgatgctt ttagttctga    3360
aaatatttac actcggatca tgttgttgat gacttaaaca aagttttgat gaagagagca    3420
aaaaaaaagc aggtggattt ggaacagttt cagggttttt tttgttttt gttttttgtt    3480 tttgttttt tttttttatt tttgttttc tgttctctgt tagaaaagtc aggtgttctc    3540
tgtcaggcta tctttatagt caattttttt tacgaactaa agtagtacct tttaatatgt    3600
agtcaacgcc cctctgctcg gggttcagtt ttgggtctta accagctgtc atgttctcta    3660
tgctgcctgc cacttgaggc actgagtgcc ctagacagtc ccatcggtgg tagccaggga    3720
aacgaaagac gaactcaact cttgctccta ataatcaact ctctgtatga aggatggcag    3780
cattaagagt cctcctgcct gggcattatt gggccagttc accctcttta aatcaaaccc    3840
gcagtggctc ccagttctcg tcccatcaga tttaaattgc taacagtatg gggggcacca    3900
cgcatctgtt ttgtcccaca atgcgctttt ctctcccaaa tcccgatttc tgctgtcata    3960
gcctctattc aatttttatt tattgtctgc cctccactta tacaatcgta gagagcaatg    4020
ccatttgtca ctttctgcaa cagttttttg agcctttatg gctgaatccc attttttcttc    4080 tctttcaaac tgtttgctcc attgctcctc ccgcacggct gtccgtacag tcatcccatc    4140
catctggggg cctctttcat ctctcaccct tcctggtgct tcgtggatct ctgcttacct    4200
ctgtgggttt tttttttttt ttttgactta ttcttctcac tggactttaa gattacttcc    4260
acagcgaaag tgctgcctcc cttttctgcc cgcagtgttc tgcgtacttt agatactact    4320
cagtgctgac atttgatggc aaaagttgcc tgcacttaaa tttctcttt taatagggtg    4380
```

```
aactagagtt ggagttttt tctcttttt ctcttttctc tctctctctc tctctctctc    4440
tctctctctc tctctctctc cctccctccc tccctccctc cctccctccc tctctctctc    4500
tttttctttc tttctttctt tcttttctttc tttctttctt tctttcttc tttctttttt    4560 tgacaaatct cacaggcttt gagaattata aaggtgaca gttcacctga aaatcacagg    4620
tctggtctgt ttaaattgtt gagaaatatc cgattaaaag tcttgtggct gtgtcctaat    4680
aggctctctt tcaggacgtt gtagtcaata gagtggctga accatacttg agtttataaa    4740
gctcaaaaac tgatgcaccc actctgctat tatcgtgtta gtaagagttc agctgtatat    4800
cattgtctag gttatcttg tcctacagtg ggtattcaaa tatggccacc agaggatatg    4860
tgtaaatata agcacctgta tttgcctgtt gttgagaact ggagggaaaa caaaaaatgt    4920
ctggcaaccc tttgcctttt taaccgtaat taattgacag tttatttaga gataagagtt    4980
ttcaaaaatc tcttaactgc cacaacccac agagggtctt gttttgccat cttcagtggc    5040
tcacagatat gatccaagtt aacttgaaag agatgagcag tacccaggaa attgtcctgc    5100
ctttaactct ggctgtcctt aattatgact gtttaatgct gaattttcca tccgtctagt    5160
gtttgagggt aaagaaaagc ctttttttaaa taagtatttc tgtaaaacgg catcggtggg    5220
atcttctgtg ttgctatcac gggtgaaaga gggaaacatt tcttattttt attaagcaga    5280
gcattattta cagaaagcca ttgttgagaa ttagttccca catcatataa atatccatta    5340
accattctaa attgtaagag aactccagtg ttgctatgca caaggaactc tcctgggggc    5400 cttttttgc atagcaatta aaggtatgct atttgtcagt agccattttt tgcagtgatt    5460
taaagaccaa agttgtttta cagctgtgtt acccttaaag gttttttttt tatgtattaa    5520
atcaatttat cactgtttga agctttgaat acctgcaatc tttgccaaga tactttttta    5580
tttaaaaaaa taactgtgta aatattaccc tgtaatatta tatatactta ataaaacatt    5640
ttaagcta                                                              5648
```

<210> SEQ ID NO 6
<211> LENGTH: 331
<212> TYPE: PRT
<213> ORGANISM: Mus musculus

<400> SEQUENCE: 6

```
Met Trp Pro Leu Ala Ala Ala Leu Leu Leu Gly Ser Cys Cys Cys Gly
  1               5                  10                  15

Ser Ala Gln Leu Leu Phe Ser Asn Val Asn Ser Ile Glu Phe Thr Ser
             20                  25                  30

Cys Asn Glu Thr Val Val Ile Pro Cys Ile Val Arg Asn Val Glu Ala
         35                  40                  45

Gln Ser Thr Glu Glu Met Phe Val Lys Trp Lys Leu Asn Lys Ser Tyr
     50                  55                  60

Ile Phe Ile Tyr Asp Gly Asn Lys Asn Ser Thr Thr Thr Asp Gln Asn
 65                  70                  75                  80

Phe Thr Ser Ala Lys Ile Ser Val Ser Asp Leu Ile Asn Gly Ile Ala
                 85                  90                  95

Ser Leu Lys Met Asp Lys Arg Asp Ala Met Val Gly Asn Tyr Thr Cys
            100                 105                 110

Glu Val Thr Glu Leu Ser Arg Glu Gly Lys Thr Val Ile Glu Leu Lys
        115                 120                 125

Asn Arg Thr Ala Phe Asn Thr Asp Gln Gly Ser Ala Cys Ser Tyr Glu
    130                 135                 140
```

```
Glu Lys Gly Gly Cys Lys Leu Val Ser Trp Phe Ser Pro Asn Glu
145                 150                 155                 160

Lys Ile Leu Ile Val Ile Phe Pro Ile Leu Ala Ile Leu Leu Phe Trp
            165                 170                 175

Gly Lys Phe Gly Ile Leu Thr Leu Lys Tyr Lys Ser Ser His Thr Asn
            180                 185                 190

Lys Arg Ile Ile Leu Leu Leu Val Ala Gly Leu Val Leu Thr Val Ile
            195                 200                 205

Val Val Val Gly Ala Ile Leu Leu Ile Pro Gly Glu Lys Pro Val Lys
        210                 215                 220

Asn Ala Ser Gly Leu Gly Leu Ile Val Ile Ser Thr Gly Ile Leu Ile
225                 230                 235                 240

Leu Leu Gln Tyr Asn Val Phe Met Thr Ala Phe Gly Met Thr Ser Phe
            245                 250                 255

Thr Ile Ala Ile Leu Ile Thr Gln Val Leu Gly Tyr Val Leu Ala Leu
            260                 265                 270

Val Gly Leu Cys Leu Cys Ile Met Ala Cys Glu Pro Val His Gly Pro
        275                 280                 285

Leu Leu Ile Ser Gly Leu Gly Ile Ile Ala Leu Ala Glu Leu Leu Gly
            290                 295                 300

Leu Val Tyr Met Lys Phe Val Ala Ser Asn Gln Arg Thr Ile Gln Pro
305                 310                 315                 320

Pro Arg Lys Ala Val Glu Glu Pro Leu Asn Glu
                325                 330

<210> SEQ ID NO 7
<211> LENGTH: 5618
<212> TYPE: DNA
<213> ORGANISM: Mus musculus

<400> SEQUENCE: 7
gcctacaccg ggagagcagg gaggaggagt tggactgagg ttgggcggct ccgaggtcca    60
gggcgagctt ggccagaggg agtagagagc agcggggctg cgcagggacg cgtgccgtga   120
gttccggtga gcgtgtgtgt cccatgctcc cgtctttcag gccggcccag gacacgaagc   180
cggaagagag ctggctggag ggacgggggc cgtgagcaga gagtgcaacc cgcgcagccc   240
cggggacagg ctgattcttg cgctctccg ccggagcctg cccagggctg gtgtgaggc   300 tggcgtcacg tcaacgagca gaggcggcca ggcggggcgg agtgcgcgtg cgcggggcgg   360
cgagcacgcg cgcgcgcgca ccccgggca gcctgggcgg ccgctcctgc ctgtcactgc   420
tgcggcgctg ctggtcggtc gtttcccttg aaggcagcag cggaggcggc ggctgctcca   480
gacacctgcg gcggcgaccc cccggcggcg cggagatgtg gcccttggcg gcggcgctgt   540
tgctgggctc ctgctgctgc ggttcagctc aactactgtt tagtaacgtc aactccatag   600
agttcacttc atgcaatgaa actgtggtca tccctttgcat cgtccgtaat gtggaggcgc   660
aaagcaccga agaaatgttt gtgaagtgga agttgaacaa atcgtatatt ttcatctatg   720
atggaaataa aaatagcact actacagatc aaaactttac cagtgcaaaa atctcagtct   780
cagacttaat caatggcatt gcctctttga aatggataa gcgcgatgcc atggtgggaa   840
actacacttg cgaagtgaca gagttatcca gagaaggcaa aacagttata gagctgaaaa   900
accgcacggt tcgtggtttt ctccaaatg aaaagatcct cattgttatt ttcccaattt   960
tggctatact cctgttctgg ggaaagtttg gtattttaac actcaaatat aaatccagcc  1020
```

```
atacgaataa gagaatcatt ctgctgctcg ttgccgggct ggtgctcaca gtcatcgtgg   1080
ttgttggagc catccttctc atcccaggag aaaagcccgt gaagaatgct tctggacttg   1140
gcctcattgt aatctctacg gggatattaa tactacttca gtacaatgtg tttatgacag   1200
cttttggaat gacctctttc accattgcca tattgatcac tcaagtgctg gctacgtcc    1260 ttgctttggt cgggctgtgt ctctgcatca tggcatgtga gccagtgcac ggccccttt    1320 tgatttcagg tttggggatc atagctctag cagaactact tggattagtt tatatgaagt   1380
ttgtcgcttc caaccagagg actatccaac ctcctaggaa agctgtagag gaacccctta   1440
acgcatttaa agagtcaaaa ggaatgatga atgacgaata ggtgaaggga agtgacggac   1500
tgtaacttgg aagtcagaaa tggaagaata cagttgtcta agcaccaggt cttcacgact   1560
cacagctgga aggaacagac aacagtaact gacttccatc caggaaaaca tgtcacataa   1620
atgattacta agtttatatt caaagcagct gtacttaca  taataaaaaa aatatgatgt   1680
gctgtgtaac caattggaat cccatttttc tattgtttct actcaactag gggcaaacgt   1740 ttcagggca  acttccaaga atgatgcttg ttagatccta gagtctctga acactgagtt   1800
taaattgatt ccgagtgaga ctcgccaagc actaacctga gggttagtta cccagagata   1860
cctatgaaaa acagtggtat ccagcaagcc ttagtaaact caggttgcca gcagctttgc   1920
cacttccgct gctagctgaa taacaagact gccacttctg ggtcatagtg atagagactg   1980
aagtagaaaa acgaatgtgg ttgggcaaat cccgtgtggc ccctctgtgt gctatgatat   2040
tgatggcact ggtgtcttca ttcttggggg ttgccatcat tcacacacac ccctttgaca   2100
tacagtgcac cccagttttg aatacatttt ttttgcaccc tgtcccgttc tgctactttg   2160
atttgcgtta tgatatatat atatatatat aataccttt  ctcctcttta aacatggtcc   2220
tgtgacacaa tagtcagttg cagaaaggag ccagacttat tcgcaaagca ctgtgctcaa   2280
actcttcaga aaaaaggaa  aaaaaaaaaa agctatagtt gtaacatatg tattccagac   2340
ctctggttta aaggcaaaag aaaaaaaatc tacagtgttt cttctcatgt tttctgatcg   2400
gaggcatgac aaagcaagac tgaaatctga actgtgtctc ctgcatggca acacgtgtct   2460
ccgtcaggcc ctcgcaaggc ccgggggagg ggttctacgc ctcttgtctc tttgttgcat   2520
gctgaacact catcgccttc ctactgtatc ctgcctcctg cagcctccct cttcctcctc   2580
ctcttcctct tcctcctctt cctcctcctc ctcctcttcc tccaagtttg aaaggtcaaa   2640
caaaactacc acattcccta cccagttaga agaaaaccac cgtcctgaca gttgtgatcg   2700
catggagtac ttttagatta ttagcacctg ttttttacctc gtttgtgggc gtgtttgtat   2760
gtgcacatgt atgaagtcgg cacatgcacc ttctgtatgg gcagaggcgt ggcatctaca   2820
gaagagcaga tgccaacttt gtgcttttag tgaatacatt aaaaaaaaaa aaccaacggt   2880
ccttattgag tggaattcta tttgatgcaa atatttgagc tctttaagac tttaaaacta   2940
gataatgtgc caagcttta  ggactgctca ccagtgccct ctgaagaaac accagtactt   3000
tttcctgttt gtgtaataaa ggcatatttg tatttgtgtt tgcatcacta atggttattt   3060
cttcttagtc cactgaatgt ttccatgtgc ctctcgtatg ccaaacttt  tgtcatcttt   3120 catgtgggga ccaaatggtt tgtctgtggc aaacctaaac ctatgacctg ctgaggcctc   3180
tcagaaaact gaccacagta ccaagatagt acttcgcaaa gaaaagtagg ttccctccct   3240
ggttttgtag ctgtcgccaa tattagcgta attccaagga gctgaacgcc tttatataaa   3300
tctgatggca cctgatgctt ttagttctga aaatatttac actcggatca tgttgttgat   3360
gacttaaaca aagttttgat gaagagagca aaaaaaaagc aggtggattt ggaacagttt   3420
```

```
cagggttttt tttgttttt gtttttgtt tttgttttt ttttttatt tttgttttc    3480
tgttctctgt tagaaaagtc aggtgttctc tgtcaggcta tctttatagt caatttttt    3540
tacgaactaa agtagtacct tttaatatgt agtcaacgcc cctctgctcg gggttcagtt    3600
ttgggtctta accagctgtc atgttctcta tgctgcctgc cacttgaggc actgagtgcc    3660
ctagacagtc ccatcggtgg tagccaggga acgaaagac gaactcaact cttgctccta    3720
ataatcaact ctctgtatga aggatggcag cattaagagt cctcctgcct gggcattatt    3780
gggccagttc accctcttta aatcaaaccc gcagtggctc ccagttctcg tcccatcaga    3840
tttaaattgc taacagtatg gggggcacca cgcatctgtt ttgtcccaca atgcgctttt    3900
ctctcccaaa tcccgatttc tgctgtcata gcctctattc aattttatt tattgtctgc    3960
cctccactta tacaatcgta gagagcaatg ccatttgtca ctttctgcaa cagttttttg    4020
agcctttatg gctgaatccc attttctc tctttcaaac tgtttgctcc attgctcctc    4080
ccgcacggct gtccgtacag tcatcccatc catctggggg cctctttcat ctctcaccct    4140
tcctggtgct tcgtggatct ctgcttacct ctgtgggttt ttttttttt ttttgactta    4200
ttcttctcac tggactttaa gattacttcc acagcgaaag tgctgcctcc ctttctgcc    4260
cgcagtgttc tgcgtacttt agatactact cagtgctgac atttgatggc aaaagttgcc    4320
tgcacttaaa tttctctttt taatagggtg aactagagtt ggagtttttt tctcttttt    4380
ctcttttctc tctctctctc tctctctctc tctctctctc tctctctctc cctccctccc    4440
tccctccctc cctccctccc tctctctctc ttttcttttc tttctttctt tctttctttc    4500
tttctttctt tctttctttc tttctttttt tgacaaatct cacaggcttt gagaattata    4560
aaaggtgaca gttcacctga aaatcacagg tctggtctgt ttaaattgtt gagaaatatc    4620
cgattaaaag tcttgtggct gtgtcctaat aggctctctt tcaggacgtt gtagtcaata    4680
gagtggctga accatacttg agtttataaa gctcaaaaac tgatgcaccc actctgctat    4740
tatcgtgtta gtaagagttc agctgtatat cattgtctag gtttatcttg tcctacagtg    4800
ggtattcaaa tatggccacc agaggatatg tgtaaatata agcacctgta tttgcctgtt    4860
gttgagaact ggagggaaaa caaaaaatgt ctggcaaccc tttgccttt taaccgtaat    4920
taattgacag tttatttaga gataagagtt ttcaaaaatc tcttaactgc cacaacccac    4980
agagggtctt gttttgccat cttcagtggc tcacagatat gatccaagtt aacttgaaag    5040
agatgagcag tacccaggaa attgtcctgc ctttaactct ggctgtcctt aattatgact    5100
gtttaatgct gaattttcca tccgtctagt gtttgagggt aaagaaaagc cttttttaaa    5160
taagtatttc tgtaaaacgg catcggtggg atcttctgtg ttgctatcac gggtgaaaga    5220
gggaaacatt tcttattttt attaagcaga gcattattta cagaaagcca ttgttgagaa    5280
ttagttccca catcatataa atatccatta accattctaa attgtaagag aactccagtg    5340
ttgctatgca caaggaactc tcctgggggc cttttttgc atagcaatta aaggtatgct    5400
atttgtcagt agccattttt tgcagtgatt taaagaccaa agttgtttta cagctgtgtt    5460
acccttaaag gttttttttt tatgtattaa atcaatttat cactgtttga agctttgaat    5520
acctgcaatc tttgccaaga tactttttta tttaaaaaaa taactgtgta aatattaccc    5580
tgtaatatta tatatactta ataaaacatt ttaagcta                           5618

<210> SEQ ID NO 8
<211> LENGTH: 321
<212> TYPE: PRT
```

<213> ORGANISM: Mus musculus

<400> SEQUENCE: 8

Met Trp Pro Leu Ala Ala Leu Leu Leu Gly Ser Cys Cys Cys Gly
1               5                   10                  15

Ser Ala Gln Leu Leu Phe Ser Asn Val Asn Ser Ile Glu Phe Thr Ser
            20                  25                  30

Cys Asn Glu Thr Val Val Ile Pro Cys Ile Val Arg Asn Val Glu Ala
        35                  40                  45

Gln Ser Thr Glu Glu Met Phe Val Lys Trp Lys Leu Asn Lys Ser Tyr
    50                  55                  60

Ile Phe Ile Tyr Asp Gly Asn Lys Asn Ser Thr Thr Asp Gln Asn
65                  70                  75                  80

Phe Thr Ser Ala Lys Ile Ser Val Ser Asp Leu Ile Asn Gly Ile Ala
                85                  90                  95

Ser Leu Lys Met Asp Lys Arg Asp Ala Met Val Gly Asn Tyr Thr Cys
            100                 105                 110

Glu Val Thr Glu Leu Ser Arg Glu Gly Lys Thr Val Ile Glu Leu Lys
        115                 120                 125

Asn Arg Thr Val Ser Trp Phe Ser Pro Asn Glu Lys Ile Leu Ile Val
    130                 135                 140

Ile Phe Pro Ile Leu Ala Ile Leu Leu Phe Trp Gly Lys Phe Gly Ile
145                 150                 155                 160

Leu Thr Leu Lys Tyr Lys Ser Ser His Thr Asn Lys Arg Ile Ile Leu
                165                 170                 175

Leu Leu Val Ala Gly Leu Val Leu Thr Val Ile Val Val Gly Ala
            180                 185                 190

Ile Leu Leu Ile Pro Gly Glu Lys Pro Val Lys Asn Ala Ser Gly Leu
    195                 200                 205

Gly Leu Ile Val Ile Ser Thr Gly Ile Leu Ile Leu Leu Gln Tyr Asn
210                 215                 220

Val Phe Met Thr Ala Phe Gly Met Thr Ser Phe Thr Ile Ala Ile Leu
225                 230                 235                 240

Ile Thr Gln Val Leu Gly Tyr Val Leu Ala Leu Val Gly Leu Cys Leu
                245                 250                 255

Cys Ile Met Ala Cys Glu Pro Val His Gly Pro Leu Leu Ile Ser Gly
            260                 265                 270

Leu Gly Ile Ile Ala Leu Ala Glu Leu Leu Gly Leu Val Tyr Met Lys
    275                 280                 285

Phe Val Ala Ser Asn Gln Arg Thr Ile Gln Pro Pro Arg Lys Ala Val
290                 295                 300

Glu Glu Pro Leu Asn Ala Phe Lys Glu Ser Lys Gly Met Met Asn Asp
305                 310                 315                 320

Glu

<210> SEQ ID NO 9
<211> LENGTH: 5021
<212> TYPE: DNA
<213> ORGANISM: Homo sapiens

<400> SEQUENCE: 9
agtgggagcg cgcgtgcgcg cggccgtgca gcctgggcag tgggtcctgc ctgtgacgcg     60
cggcggcggt cggtcctgcc tgtaacggcg gcggcggctg ctgctccgga cacctgcggc    120
ggcggcggcg accccgcggc gggcgcggag atgtggcccc tggtagcggc gctgttgctg    180

-continued

```
ggctcggcgt gctgcggatc agctcagcta ctatttaata aaacaaaatc tgtagaattc    240
acgttttgta atgacactgt cgtcattcca tgctttgtta ctaatatgga ggcacaaaac    300
actactgaag tatacgtaaa gtggaaattt aaaggaagag atatttacac ctttgatgga    360
gctctaaaca agtccactgt ccccactgac tttagtagtg caaaaattga agtctcacaa    420
ttactaaaag gagatgcctc tttgaagatg gataagagtg atgctgtctc acacacagga    480
aactacactt gtgaagtaac agaattaacc agagaaggtg aaacgatcat cgagctaaaa    540
tatcgtgttg tttcatggtt ttctccaaat gaaaatattc ttattgttat tttcccaatt    600
tttgctatac tcctgttctg gggacagttt ggtattaaaa cacttaaata tagatccggt    660
ggtatggatg agaaaacaat tgctttactt gttgctggac tagtgatcac tgtcattgtc    720
attgttggag ccattctttt cgtcccaggt gaatattcat aaagaatgc tactggcctt    780 ggtttaattg tgacttctac agggatatta atattacttc actactatgt gtttagtaca    840
gcgattggat taacctcctt cgtcattgcc atattggtta ttcaggtgat agcctatatc    900
ctcgctgtgg ttgactgag tctctgtatt gcggcgtgta taccaatgca tggccctctt    960
ctgatttcag gtttgagtat cttagctcta gcacaattac ttggactagt ttatatgaaa   1020
tttgtggaat aactgaagtg aagtgatgga ctccgatttg gagagtagta agacgtgaaa   1080
ggaatacact tgtgtttaag caccatggcc ttgatgattc actgttgggg agaagaaaca   1140
agaaaagtaa ctggttgtca cctatgagac ccttacgtga ttgttagtta agtttttatt   1200
caaagcagct gtaatttagt taataaaata attatgatct atgttgtttg cccaattgag   1260
atccagtttt ttgttgttat ttttaatcaa ttaggggcaa tagtagaatg gacaatttcc   1320
aagaatgatg cctttcaggt cctagggcct ctggcctcta ggtaaccagt ttaaattggt   1380
tcagggtgat aactacttag cactgccctg gtgattaccc agagatatct atgaaaacca   1440
gtggcttcca tcaaaccttt gccaactcag gttcacagca gctttgggca gttatggcag   1500
tatggcatta gctgagaggt gtctgccact tctgggtcaa tggaataata aattaagtac   1560
aggcaggaat ttggttggga gcatcttgta tgatctccgt atgatgtgat attgatggag   1620
atagtggtcc tcattcttgg gggttgccat tcccacattc cccttcaac aaacagtgta   1680 acaggtcctt cccagattta gggtactttt attgatggat atgttttcct tttattcaca   1740
taaccccttg aaaccctgtc ttgtcctcct gttacttgct tctgctgtac aagatgtagc   1800
accttttctc ctctttgaac atggtctagt gacacggtag caccagttgc aggaaggagc   1860
cagacttgtt ctcagagcac tgtgttcaca cttttcagca aaaatagcta tggttgtaac   1920
atatgtattc ccttcctctg atttgaaggc aaaaatctac agtgtttctt cacttctttt   1980
ctgatctggg gcatgaaaaa agcaagattg aaatttgaac tatgagtctc ctgcatggca   2040
acaaaatgtg tgtcaccatc aggccaacag gccagccctt gaatggggat ttattactgt   2100
tgtatctatg ttgcatgata acattcatc accttcctcc tgtagtcctg cctcgtactc   2160
cccttcccct atgattgaaa agtaaacaaa acccacattt cctatcctgg ttagaagaaa   2220
attaatgttc tgacagttgt gatcgcctgg agtactttta gacttttagc attcgttttt   2280
tacctgtttg tggatgtgtg tttgtatgtg catacgtatg agataggcac atgcatcttc   2340
tgtatggaca aaggtggggt acctacagga gagcaaaggt taattttgtg cttttagtaa   2400
aaacatttaa atacaaagtt ctttattggg tggaattata tttgatgcaa atatttgatc   2460
acttaaaact tttaaaactt ctaggtaatt tgccacgctt tttgactgct caccaatacc   2520
```

```
ctgtaaaaat acgtaattct tcctgtttgt gtaataagat attcatattt gtagttgcat   2580
taataatagt tatttcttag tccatcagat gttcccgtgt gcctctttta tgccaaattg   2640
attgtcatat ttcatgttgg gaccaagtag tttgcccatg gcaaacctaa atttatgacc   2700
tgctgaggcc tctcagaaaa ctgagctac tagcaagaca gctcttcttg aaaaaaaaaa   2760
tatgtataca caaatatata cgtatatcta tatatacgta tgtatataca cacatgtata   2820
ttcttccttg attgtgtagc tgtccaaaat aataacatat atagagggag ctgtattcct   2880
ttatacaaat ctgatggctc ctgcagcact ttttccttct gaaaatattt acattttgct   2940
aacctagttt gttactttaa aaatcagttt tgatgaaagg agggaaaagc agatggactt   3000 gaaaagatc caagctccta ttagaaaagg tatgaaaatc tttatagtaa aattttttat   3060
aaactaaagt tgtaccttt aatatgtagt aaactctcat ttatttgggg ttcgctcttg   3120
gatctcatcc atccattgtg ttctctttaa tgctgcctgc cttttgaggc attcactgcc   3180
ctagacaatg ccaccagaga tagtggggga aatgccagat gaaaccaact cttgctctca   3240
ctagttgtca gcttctctgg ataagtgacc acagaagcag gagtcctcct gcttgggcat   3300
cattgggcca gttccttctc tttaaatcag atttgtaatg gctcccaaat tccatcacat   3360
cacatttaaa ttgcagacag tgttttgcac atcatgtatc tgttttgtcc cataatatgc   3420
tttttactcc ctgatcccag tttctgctgt tgactcttcc attcagtttt atttattgtg   3480
tgttctcaca gtgacaccat ttgtcctttt ctgcaacaac ctttccagct acttttgcca   3540
aattctattt gtcttctcct tcaaaacatt ctcctttgca gttcctcttc atctgtgtag   3600
ctgctctttt gtctcttaac ttaccattcc tatagtactt tatgcatctc tgcttagttc   3660 tattagttt ttggccttgc tcttctcctt gattttaaaa ttccttctat agctagagct   3720
tttctttctt tcattctctc ttcctgcagt gttttgcata catcagaagc taggtacata   3780
agttaaatga ttgagagttg gctgtattta gatttatcac ttttaatag ggtgagcttg   3840 agagttttct ttctttctgt ttttttttt tgtttttttt tttttttttt tttttttttt   3900
ttttgactaa tttcacatgc tctaaaaacc ttcaaggtg attattttc tcctggaaac   3960 tccaggtcca ttctgtttaa atccctaaga atgtcagaat taaaataaca gggctatccc   4020
gtaattggaa atatttcttt tttcaggatg ctatagtcaa tttagtaagt gaccaccaaa   4080
ttgttatttg cactaacaaa gctcaaaaca cgataagttt actcctccat ctcagtaata   4140
aaaattaagc tgtaatcaac cttctaggtt tctcttgtct taaaatgggt attcaaaaat   4200
ggggatctgt ggtgtatgta tggaaacaca tactccttaa tttacctgtt gttggaaact   4260
ggagaaatga ttgtcgggca accgtttatt ttttattgta ttttatttgg ttgagggatt   4320
tttttataaa cagtttact tgtgtcatat tttaaaatta ctaactgcca tcacctgctg   4380
gggtcctttg ttaggtcatt ttcagtgact aataggata atccaggtaa ctttgaagag   4440
atgagcagtg agtgaccagg cagttttct gcctttagct ttgacagttc ttaattaaga   4500
tcattgaaga ccagctttct cataaattc tcttttgaa aaaagaaag catttgtact   4560 aagctcctct gtaagacaac atcttaaatc ttaaagtgt tgttatcatg actggtgaga   4620
gaagaaaaca ttttgttttt attaaatgga gcattattta caaaaagcca ttgttgagaa   4680
ttagatccca catcgtataa atatctatta accattctaa ataaagagaa ctccagtgtt   4740
gctatgtgca agatcctctc ttggagcttt tttgcatagc aattaaaggt gtgctatttg   4800
tcagtagcca ttttttgca gtgatttgaa gaccaaagtt gttttacagc tgtgttaccg   4860
ttaaaggttt tttttttat atgtattaaa tcaattatc actgtttaaa gctttgaata   4920
```

```
tctgcaatct tgccaaggt acttttttat ttaaaaaaa acataacttt gtaaatatta      4980
ccctgtaata ttatatatac ttaataaaac attttaagct a                         5021

<210> SEQ ID NO 10
<211> LENGTH: 293
<212> TYPE: PRT
<213> ORGANISM: Homo sapiens

<400> SEQUENCE: 10

Met Trp Pro Leu Val Ala Ala Leu Leu Gly Ser Ala Cys Cys Gly
1               5                   10                  15

Ser Ala Gln Leu Leu Phe Asn Lys Thr Lys Ser Val Glu Phe Thr Phe
            20                  25                  30

Cys Asn Asp Thr Val Val Ile Pro Cys Phe Val Thr Asn Met Glu Ala
        35                  40                  45

Gln Asn Thr Thr Glu Val Tyr Val Lys Trp Lys Phe Lys Gly Arg Asp
    50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
        115                 120                 125

Leu Lys Tyr Arg Val Val Ser Trp Phe Ser Pro Asn Glu Asn Ile Leu
    130                 135                 140

Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Gly Met Asp Glu Lys Thr
                165                 170                 175

Ile Ala Leu Leu Val Ala Gly Leu Val Ile Thr Val Ile Val Ile Val
            180                 185                 190

Gly Ala Ile Leu Phe Val Pro Gly Glu Tyr Ser Leu Lys Asn Ala Thr
        195                 200                 205

Gly Leu Gly Leu Ile Val Thr Ser Thr Gly Ile Leu Ile Leu Leu His
    210                 215                 220

Tyr Tyr Val Phe Ser Thr Ala Ile Gly Leu Thr Ser Phe Val Ile Ala
225                 230                 235                 240

Ile Leu Val Ile Gln Val Ile Ala Tyr Ile Leu Ala Val Val Gly Leu
                245                 250                 255

Ser Leu Cys Ile Ala Ala Cys Ile Pro Met His Gly Pro Leu Leu Ile
            260                 265                 270

Ser Gly Leu Ser Ile Leu Ala Leu Ala Gln Leu Leu Gly Leu Val Tyr
        275                 280                 285

Met Lys Phe Val Glu
    290

<210> SEQ ID NO 11
<211> LENGTH: 5288
<212> TYPE: DNA
<213> ORGANISM: Homo sapiens

<400> SEQUENCE: 11
ggggagcagg cgggggagcg ggcgggaagc agtgggagcg cgcgtgcgcg cggccgtgca     60
```

```
gcctgggcag tgggtcctgc ctgtgacgcg cggcggcggt cggtcctgcc tgtaacggcg      120
gcggcggctg ctgctccaga cacctgcggc ggcggcggcg accccgcggc gggcgcggag      180
atgtggcccc tggtagcggc gctgttgctg ggctcggcgt gctgcggatc agctcagcta      240
ctatttaata aaacaaaatc tgtagaattc acgttttgta atgacactgt cgtcattcca      300
tgctttgtta ctaatatgga ggcacaaaac actactgaag tatacgtaaa gtggaaattt      360
aaaggaagag atatttacac ctttgatgga gctctaaaca agtccactgt ccccactgac      420
tttagtagtg caaaaattga agtctcacaa ttactaaaag gagatgcctc tttgaagatg      480
gataagagtg atgctgtctc acacacagga aactacactt gtgaagtaac agaattaacc      540
agagaaggtg aaacgatcat cgagctaaaa tatcgtgttg tttcatggtt ttctccaaat      600
gaaaatattc ttattgttat tttcccaatt tttgctatac tcctgttctg gggacagttt      660
ggtattaaaa cacttaaata tagatccggt ggtatggatg agaaaacaat tgctttactt      720
gttgctggac tagtgatcac tgtcattgtc attgttggag ccattctttt cgtcccaggt      780
gaatattcat aaagaatgc tactggcctt ggtttaattg tgacttctac agggatatta      840
atattacttc actactatgt gtttagtaca gcgattggat taacctcctt cgtcattgcc      900
atattggtta ttcaggtgat agcctatatc ctcgctgtgg ttggactgag tctctgtatt      960
gcggcgtgta taccaatgca tggccctctt ctgatttcag gtttgagtat cttagctcta     1020
gcacaattac ttggactagt ttatatgaaa tttgtggctt ccaatcagaa gactatacaa     1080
cctcctagga ataactgaag tgaagtgatg gactccgatt tggagagtag taagacgtga     1140
aaggaataca cttgtgttta agcaccatgg ccttgatgat tcactgttgg ggagaagaaa     1200
caagaaaagt aactggttgt cacctatgag acccttacgt gattgttagt aagttttta      1260 ttcaaagcag ctgtaattta gttaataaaa taattatgat ctatgttgtt tgcccaattg     1320
agatccagtt ttttgttgtt atttttaatc aattaggggc aatagtagaa tggacaattt     1380
ccaagaatga tgccttttcag gtcctagggc ctctggcctc taggtaacca gtttaaattg     1440
gttcagggtg ataactactt agcactgccc tggtgattac ccagagatat ctatgaaaac     1500
cagtggcttc catcaaacct tgccaactc aggttcacag cagctttggg cagttatggc      1560
agtatggcat tagctgagag gtgtctgcca cttctgggtc aatggaataa taaattaagt     1620
acaggcagga atttggttgg gagcatcttg tatgatctcc gtatgatgtg atattgatgg     1680
agatagtggt cctcattctt gggggttgcc attcccacat tccccttca caaacagtg      1740 taacaggtcc ttcccagatt tagggtactt ttattgatgg atatgttttc ctttattca      1800 cataacccct tgaaaccctg tcttgtcctc ctgttacttg cttctgctgt acaagatgta     1860
gcaccttttc tcctctttga acatggtcta gtgacacggt agcaccagtt gcaggaagga     1920
gccagacttg ttctcagagc actgtgttca cacttttcag caaaaatagc tatggttgta     1980
acatatgtat tccttcctc tgatttgaag gcaaaaatct acagtgtttc ttcacttctt     2040
ttctgatctg gggcatgaaa aaagcaagat tgaaatttga actatgagtc tcctgcatgg     2100
caacaaaatg tgtgtcacca tcaggccaac aggccagccc ttgaatgggg atttattact     2160
gttgtatcta tgttgcatga taaacattca tcaccttcct cctgtagtcc tgcctcgtac     2220
tccccttccc ctatgattga aaagtaaaca aaacccacat ttcctatcct ggttagaaga     2280
aaattaatgt tctgacagtt gtgatcgcct ggagtacttt tagacttta gcattcgttt      2340 tttacctgtt tgtggatgtg tgtttgtatg tgcatacgta tgagataggc acatgcatct     2400
```

```
tctgtatgga caaaggtggg gtacctacag gagagcaaag gttaattttg tgcttttagt    2460
aaaaacattt aaatacaaag ttctttattg ggtggaatta tatttgatgc aaatatttga    2520
tcacttaaaa cttttaaaac ttctaggtaa tttgccacgc ttttgactg ctcaccaata     2580
ccctgtaaaa atacgtaatt cttcctgttt gtgtaataag atattcatat ttgtagttgc    2640
attaataata gttatttctt agtccatcag atgttcccgt gtgcctcttt tatgccaaat    2700
tgattgtcat atttcatgtt gggaccaagt agtttgccca tggcaaacct aaatttatga    2760
cctgctgagg cctctcagaa aactgagcat actagcaaga cagctcttct tgaaaaaaaa    2820
aatatgtata cacaaatata tacgtatatc tatatatacg tatgtatata cacacatgta    2880
tattcttcct tgattgtgta gctgtccaaa ataataacat atatagaggg agctgtattc    2940
ctttatacaa atctgatggc tcctgcagca cttttcctt ctgaaaatat ttacattttg     3000
ctaacctagt ttgttacttt aaaaatcagt tttgatgaaa ggagggaaaa gcagatggac    3060
ttgaaaaaga tccaagctcc tattagaaaa ggtatgaaaa tctttatagt aaaatttttt    3120
ataaactaaa gttgtacctt ttaatatgta gtaaactctc atttatttgg ggttcgctct    3180
tggatctcat ccatccattg tgttctcttt aatgctgcct gccttttgag gcattcactg    3240
ccctagacaa tgccaccaga gatagtgggg gaaatgccag atgaaaccaa ctcttgctct    3300
cactagttgt cagcttctct ggataagtga ccacagaagc aggagtcctc ctgcttgggc    3360
atcattgggc cagttccttc tctttaaatc agatttgtaa tggctcccaa attccatcac    3420
atcacattta aattgcagac agtgttttgc acatcatgta tctgttttgt cccataatat    3480
gcttttact ccctgatccc agtttctgct gttgactctt ccattcagtt ttatttattg     3540
tgtgttctca cagtgacacc atttgtcctt ttctgcaaca accttccag ctactttgc     3600
caaattctat ttgtcttctc cttcaaaaca ttctcctttg cagttcctct tcatctgtgt    3660
agctgctctt ttgtctctta acttaccatt cctatagtac tttatgcatc tctgcttagt    3720
tctattagtt ttttggcctt gctcttctcc ttgattttaa aattccttct atagctagag    3780
cttttcttc tttcattctc tcttcctgca gtgttttgca tacatcagaa gctaggtaca     3840
taagttaaat gattgagagt tggctgtatt tagatttatc actttttaat agggtgagct    3900
tgagagttttt cttctttct gttttttttt tttgttttt tttttttttt tttttttt      3960
tttttttgact aatttcacat gctctaaaaa ccttcaaagg tgattatttt tctcctggaa   4020
actccaggtc cattctgttt aaatccctaa gaatgtcaga attaaaataa cagggctatc    4080
ccgtaattgg aaatatttct ttttttcagga tgctatagtc aatttagtaa gtgaccacca   4140
aattgttatt tgcactaaca aagctcaaaa cacgataagt ttactcctcc atctcagtaa    4200
taaaaattaa gctgtaatca accttctagg tttctcttgt cttaaaatgg gtattcaaaa    4260
atggggatct gtggtgtatg tatggaaaca catactcctt aatttacctg ttgttggaaa    4320
ctggagaaat gattgtcggg caaccgttta ttttttattg tattttattt ggttgaggga    4380
ttttttttata aacagtttta cttgtgtcat attttaaaat tactaactgc catcacctgc   4440
tggggtcctt tgttaggtca ttttcagtga ctaataggga taatccaggt aactttgaag    4500
agatgagcag tgagtgacca ggcagttttt ctgcctttag ctttgacagt tcttaattaa    4560
gatcattgaa gaccagcttt ctcataaatt tctctttttg aaaaaaagaa agcatttgta    4620
ctaagctcct ctgtaagaca acatcttaaa tcttaaaagt gttgttatca tgactggtga    4680
gagaagaaaa cattttgttt ttattaaatg gagcattatt tacaaaaagc cattgttgag    4740
aattagatcc cacatcgtat aaatatctat taaccattct aaataaagag aactccagtg    4800
```

-continued

```
ttgctatgtg caagatcctc tcttggagct ttttgcata gcaattaaag gtgtgctatt      4860
tgtcagtagc cattttttg cagtgatttg aagaccaaag ttgttttaca gctgtgttac      4920
cgttaaaggt tttttttttt atatgtatta aatcaattta tcactgttta aagctttgaa    4980
tatctgcaat ctttgccaag gtactttttt atttaaaaaa aaacataact ttgtaaatat    5040
taccctgtaa tattatatat acttaataaa acattttaag ctattttgtt gggctatttc    5100
tattgctgct acagcagacc acaagcacat ttctgaaaaa tttaatttat taatgtattt    5160
ttaagttgct tatattctag gtaacaatgt aaagaatgat ttaaaatatt aattatgaat    5220
tttttgagta taatacccaa taagcttta attagagcag agttttaatt aaaagttta    5280 aatcagtc                                                              5288
```

<210> SEQ ID NO 12
<211> LENGTH: 305
<212> TYPE: PRT
<213> ORGANISM: Homo sapiens

<400> SEQUENCE: 12

```
Met Trp Pro Leu Val Ala Ala Leu Leu Leu Gly Ser Ala Cys Cys Gly
1               5                   10                  15

Ser Ala Gln Leu Leu Phe Asn Lys Thr Lys Ser Val Glu Phe Thr Phe
            20                  25                  30

Cys Asn Asp Thr Val Val Ile Pro Cys Phe Val Thr Asn Met Glu Ala
        35                  40                  45

Gln Asn Thr Thr Glu Val Tyr Val Lys Trp Lys Phe Lys Gly Arg Asp
    50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
        115                 120                 125

Leu Lys Tyr Arg Val Val Ser Trp Phe Ser Pro Asn Glu Asn Ile Leu
    130                 135                 140

Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Gly Met Asp Glu Lys Thr
                165                 170                 175

Ile Ala Leu Leu Val Ala Gly Leu Val Ile Thr Val Ile Val Ile Val
            180                 185                 190

Gly Ala Ile Leu Phe Val Pro Gly Glu Tyr Ser Leu Lys Asn Ala Thr
        195                 200                 205

Gly Leu Gly Leu Ile Val Thr Ser Thr Gly Ile Leu Ile Leu Leu His
    210                 215                 220

Tyr Tyr Val Phe Ser Thr Ala Ile Gly Leu Thr Ser Phe Val Ile Ala
225                 230                 235                 240

Ile Leu Val Ile Gln Val Ile Ala Tyr Ile Leu Ala Val Val Gly Leu
                245                 250                 255

Ser Leu Cys Ile Ala Ala Cys Ile Pro Met His Gly Pro Leu Leu Ile
            260                 265                 270

Ser Gly Leu Ser Ile Leu Ala Leu Ala Gln Leu Leu Gly Leu Val Tyr
```

```
            275                 280                 285
Met Lys Phe Val Ala Ser Asn Gln Lys Thr Ile Gln Pro Pro Arg Asn
        290                 295                 300

Asn
305

<210> SEQ ID NO 13
<211> LENGTH: 5078
<212> TYPE: DNA
<213> ORGANISM: Homo sapiens

<400> SEQUENCE: 13
agtgggagcg cgcgtgcgcg cggccgtgca gcctgggcag tgggtcctgc ctgtgacgcg      60
cggcggcggt cggtcctgcc tgtaacggcg gcggcggctg ctgctccgga cacctgcggc     120
ggcggcggcg accccgcggc gggcgcggag atgtggcccc tggtagcggc gctgttgctg     180
ggctcggcgt gctgcggatc agctcagcta ctatttaata aaacaaaatc tgtagaattc     240
acgttttgta atgacactgt cgtcattcca tgctttgtta ctaatatgga ggcacaaaac     300
actactgaag tatacgtaaa gtggaaattt aaaggaagag atatttacac ctttgatgga     360
gctctaaaca agtccactgt ccccactgac tttagtagtg caaaaattga agtctcacaa     420
ttactaaaag gagatgcctc tttgaagatg ataagagtg atgctgtctc acacacagga     480
aactacactt gtgaagtaac agaattaacc agagaaggtg aaacgatcat cgagctaaaa     540
tatcgtgttg tttcatggtt ttctccaaat gaaaatattc ttattgttat tttcccaatt     600
tttgctatac tcctgttctg gggacagttt ggtattaaaa cacttaaata tagatccggt     660
ggtatggatg agaaaacaat tgctttactt gttgctggac tagtgatcac tgtcattgtc     720
attgttggag ccattctttt cgtcccaggt gaatattcat aaagaatgc tactggcctt     780 ggtttaattg tgacttctac agggatatta atattacttc actactatgt gtttagtaca     840
gcgattggat taacctcctt cgtcattgcc atattggtta ttcaggtgat agcctatatc     900
ctcgctgtgg ttgactgag tctctgtatt gcggcgtgta taccaatgca tggccctctt     960
ctgatttcag gtttgagtat cttagctcta gcacaattac ttggactagt ttatatgaaa    1020
tttgtggctt ccaatcagaa gactatacaa cctcctagga agctgtaga ggaaccccctt    1080 aatgaataac tgaagtgaag tgatggactc cgatttggag agtagtaaga cgtgaaagga    1140
atacacttgt gtttaagcac catggccttg atgattcact gttggggaga gaaacaaga    1200 aaagtaactg ttgtcacct atgagaccct tacgtgattg ttagttaagt ttttattcaa    1260
agcagctgta atttagttaa taaaataatt atgatctatg ttgtttgccc aattgagatc    1320
cagttttttg ttgttatttt taatcaatta ggggcaatag tagaatggac aatttccaag    1380
aatgatgcct ttcaggtcct agggcctctg gcctctaggt aaccagttta aattggttca    1440
gggtgataac tacttagcac tgccctggtg attacccaga gatatctatg aaaaccagtg    1500
gcttccatca aacctttgcc aactcaggtt cacagcagct ttgggcagtt atggcagtat    1560
ggcattagct gagaggtgtc tgccacttct gggtcaatgg aataataaat taagtacagg    1620
caggaatttg gttgggagca tcttgtatga tctccgtatg atgtgatatt gatggagata    1680
gtggtcctca ttcttggggg ttgccattcc cacattcccc cttcaacaaa cagtgtaaca    1740
ggtccttccc agatttaggg tacttttatt gatggatatg ttttcctttt attcacataa    1800 cccccttgaaa ccctgtcttg tcctcctgtt acttgcttct gctgtacaag atgtagcacc    1860
ttttctcctc tttgaacatg gtctagtgac acggtagcac cagttgcagg aaggagccag    1920
```

```
acttgttctc agagcactgt gttcacactt ttcagcaaaa atagctatgg ttgtaacata      1980
tgtattccct tcctctgatt tgaaggcaaa aatctacagt gtttcttcac ttctttttctg     2040 atctggggca tgaaaaaagc aagattgaaa tttgaactat gagtctcctg catggcaaca     2100
aaatgtgtgt caccatcagg ccaacaggcc agcccttgaa tggggattta ttactgttgt     2160
atctatgttg catgataaac attcatcacc ttcctcctgt agtcctgcct cgtactcccc     2220
ttcccctatg attgaaaagt aaacaaaacc cacatttcct atcctggtta gaagaaaatt     2280
aatgttctga cagttgtgat cgcctggagt acttttagac ttttagcatt cgttttttac     2340
ctgtttgtgg atgtgtgttt gtatgtgcat acgtatgaga taggcacatg catcttctgt     2400
atggacaaag gtggggtacc tacaggagag caaaggttaa ttttgtgctt ttagtaaaaa     2460
catttaaata caaagttctt tattgggtgg aattatattt gatgcaaata tttgatcact     2520
taaaactttt aaaacttcta ggtaatttgc cacgcttttt gactgctcac caatacccctg    2580 taaaaatacg taattcttcc tgtttgtgta ataagatatt catatttgta gttgcattaa     2640
taatagttat ttcttagtcc atcagatgtt cccgtgtgcc tcttttatgc caaattgatt    2700
gtcatatttc atgttgggac caagtagttt gcccatggca aacctaaatt tatgacctgc    2760
tgaggcctct cagaaaactg agcatactag caagacagct cttcttgaaa aaaaaaatat    2820
gtatacacaa atatatacgt atatctatat atacgtatgt atatacacac atgtatattc    2880
ttccttgatt gtgtagctgt ccaaaataat aacatatata gagggagctg tattcctttta  2940 tacaaatctg atggctcctg cagcactttt tccttctgaa atatttaca ttttgctaac     3000 ctagtttgtt acttttaaaaa tcagttttga tgaaaggagg gaaaagcaga tggacttgaa    3060
aaagatccaa gctcctatta gaaaaggtat gaaaatcttt atagtaaaat tttttataaa    3120
ctaaagttgt acctttttaat atgtagtaaa ctctcattta tttgggggttc gctcttggat   3180 ctcatccatc cattgtgttc tcttttaatgc tgcctgcctt ttgaggcatt cactgccta    3240 gacaatgcca ccagagatag tgggggaaat gccagatgaa accaactctt gctctcacta    3300
gttgtcagct tctctggata agtgaccaca gaagcaggag tcctcctgct tgggcatcat    3360
tgggccagtt ccttctcttt aaatcagatt tgtaatggct cccaaattcc atcacatcac    3420
atttaaattg cagacagtgt tttgcacatc atgtatctgt tttgtcccat aatatgcttt    3480
ttactccctg atcccagttt ctgctgttga ctcttccatt cagttttatt tattgtgtgt   3540
tctcacagtg acaccatttg tccttttctg caacaacctt tccagctact tttgccaaat   3600
tctatttgtc ttctccttca aaacattctc ctttgcagtt cctcttcatc tgtgtagctg   3660
ctcttttgtc tcttaactta ccattcctat agtactttat gcatctctgc ttagttctat   3720
tagttttttg gccttgctct tctccttgat tttaaaattc cttctatagc tagagctttt   3780 cttttctttca ttctctcttc ctgcagtgtt ttgcatacat cagaagctag gtacataagt   3840
taaatgattg agagttggct gtatttagat ttatcacttt ttaatagggt gagcttgaga   3900
gttttctttc tttctgttttt ttttttttgt tttttttttt tttttttttt tttttttttt  3960
tgactaattt cacatgctct aaaaaccttc aaaggtgatt attttttctcc tggaaactcc   4020 aggtccattc tgtttaaatc cctaagaatg tcagaattaa aataacaggg ctatcccgta   4080
attggaaata tttctttttt caggatgcta tagtcaattt agtaagtgac caccaaattg   4140
ttatttgcac taacaaagct caaaacacga taagtttact cctccatctc agtaataaaa   4200
attaagctgt aatcaacctt ctaggtttct cttgtcttaa aatgggtatt caaaaatggg    4260
```

```
gatctgtggt gtatgtatgg aaacacatac tccttaattt acctgttgtt ggaaactgga    4320
gaaatgattg tcgggcaacc gtttatttt tattgtattt tatttggttg agggatttt    4380 ttataaacag ttttacttgt gtcatatttt aaaattacta actgccatca cctgctgggg    4440
tcctttgtta ggtcattttc agtgactaat agggataatc caggtaactt tgaagagatg    4500
agcagtgagt gaccaggcag ttttctgcc tttagctttg acagttctta attaagatca    4560
ttgaagacca gctttctcat aaatttctct ttttgaaaaa aagaaagcat ttgtactaag    4620
ctcctctgta agacaacatc ttaaatctta aaagtgttgt tatcatgact ggtgagagaa    4680
gaaaacattt tgtttttatt aaatggagca ttatttacaa aaagccattg ttgagaatta    4740
gatcccacat cgtataaata tctattaacc attctaaata aagagaactc cagtgttgct    4800
atgtgcaaga tcctctcttg gagcttttt gcatagcaat taaggtgtg ctatttgtca    4860 gtagccattt ttttgcagtg atttgaagac caaagttgtt ttacagctgt gttaccgtta    4920 aaggttttt tttttatatg tattaaatca atttatcact gtttaaagct ttgaatatct    4980
gcaatctttg ccaaggtact tttttattta aaaaaaaaca taactttgta aatattaccc    5040
tgtaatatta tatatactta ataaaacatt ttaagcta                           5078
```

<210> SEQ ID NO 14
<211> LENGTH: 312
<212> TYPE: PRT
<213> ORGANISM: Homo sapiens

<400> SEQUENCE: 14

Met Trp Pro Leu Val Ala Ala Leu Leu Leu Gly Ser Ala Cys Cys Gly
1               5                   10                  15

Ser Ala Gln Leu Leu Phe Asn Lys Thr Lys Ser Val Glu Phe Thr Phe
            20                  25                  30

Cys Asn Asp Thr Val Val Ile Pro Cys Phe Val Thr Asn Met Glu Ala
        35                  40                  45

Gln Asn Thr Thr Glu Val Tyr Val Lys Trp Lys Phe Lys Gly Arg Asp
    50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
        115                 120                 125

Leu Lys Tyr Arg Val Val Ser Trp Phe Ser Pro Asn Glu Asn Ile Leu
    130                 135                 140

Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Gly Met Asp Glu Lys Thr
                165                 170                 175

Ile Ala Leu Leu Val Ala Gly Leu Val Ile Thr Val Ile Val Ile Val
            180                 185                 190

Gly Ala Ile Leu Phe Val Pro Gly Glu Tyr Ser Leu Lys Asn Ala Thr
        195                 200                 205

Gly Leu Gly Leu Ile Val Thr Ser Thr Gly Ile Leu Ile Leu Leu His
    210                 215                 220

Tyr Tyr Val Phe Ser Thr Ala Ile Gly Leu Thr Ser Phe Val Ile Ala

```
            225                 230                 235                 240
Ile Leu Val Ile Gln Val Ile Ala Tyr Ile Leu Ala Val Val Gly Leu
                245                 250                 255
Ser Leu Cys Ile Ala Ala Cys Ile Pro Met His Gly Pro Leu Leu Ile
                260                 265                 270
Ser Gly Leu Ser Ile Leu Ala Leu Ala Gln Leu Leu Gly Leu Val Tyr
                275                 280                 285
Met Lys Phe Val Ala Ser Asn Gln Lys Thr Ile Gln Pro Pro Arg Lys
                290                 295                 300
Ala Val Glu Glu Pro Leu Asn Glu
305                 310

<210> SEQ ID NO 15
<211> LENGTH: 5346
<212> TYPE: DNA
<213> ORGANISM: Homo sapiens

<400> SEQUENCE: 15
```

| | | | | | |
|---|---|---|---|---|---|
| ggggagcagg | cggggagcg | ggcgggaagc | agtgggagcg | cgcgtgcgcg | cggccgtgca | 60 |
| gcctgggcag | tgggtcctgc | ctgtgacgcg | cggcggcggt | cggtcctgcc | tgtaacggcg | 120 |
| gcggcggctg | ctgctccaga | cacctgcggc | ggcggcggcg | accccgcggc | gggcgcggag | 180 |
| atgtggcccc | tggtagcggc | gctgttgctg | ggctcggcgt | gctgcggatc | agctcagcta | 240 |
| ctatttaata | aaacaaaatc | tgtagaattc | acgttttgta | atgacactgt | cgtcattcca | 300 |
| tgctttgtta | ctaatatgga | ggcacaaaac | actactgaag | tatacgtaaa | gtggaaattt | 360 |
| aaaggaagag | atatttacac | ctttgatgga | gctctaaaca | agtccactgt | ccccactgac | 420 |
| tttagtagtg | caaaaattga | agtctcacaa | ttactaaaag | gagatgcctc | tttgaagatg | 480 |
| gataagagtg | atgctgtctc | acacacagga | aactacactt | gtgaagtaac | agaattaacc | 540 |
| agagaaggtg | aaacgatcat | cgagctaaaa | tatcgtgttg | tttcatggtt | ttctccaaat | 600 |
| gaaaatattc | ttattgttat | tttcccaatt | tttgctatac | tcctgttctg | gggacagttt | 660 |
| ggtattaaaa | cacttaaata | tagatccggt | ggtatggatg | agaaaacaat | tgctttactt | 720 |
| gttgctggac | tagtgatcac | tgtcattgtc | attgttggag | ccattctttt | cgtcccaggt | 780 |
| gaatattcat | taagaatgc | tactggcctt | ggtttaattg | tgacttctac | agggatatta | 840 |
| atattacttc | actactatgt | gtttagtaca | gcgattggat | taacctcctt | cgtcattgcc | 900 |
| atattggtta | ttcaggtgat | agcctatatc | ctcgctgtgg | ttggactgag | tctctgtatt | 960 |
| gcggcgtgta | taccaatgca | tggccctctt | ctgatttcag | gttgagtat | cttagctcta | 1020 |
| gcacaattac | ttggactagt | ttatatgaaa | tttgtggctt | ccaatcagaa | gactatacaa | 1080 |
| cctcctagga | aagctgtaga | ggaaccccctt | aatgcattca | agaatcaaa | aggaatgatg | 1140 |
| aatgatgaat | aactgaagtg | aagtgatgga | ctccgatttg | gagagtagta | agacgtgaaa | 1200 |
| ggaatacact | tgtgtttaag | caccatggcc | ttgatgattc | actgttgggg | agaagaaaca | 1260 |
| agaaaagtaa | ctggttgtca | cctatgagac | ccttacgtga | ttgttagtta | agttttatt | 1320 |
| caaagcagct | gtaatttagt | taataaaata | attatgatct | atgttgtttg | cccaattgag | 1380 |
| atccagtttt | ttgttgttat | ttttaatcaa | ttaggggcaa | tagtagaatg | gacaatttcc | 1440 |
| aagaatgatg | cctttcaggt | cctagggcct | ctggcctcta | ggtaaccagt | ttaaattggt | 1500 |
| tcagggtgat | aactacttag | cactgccctg | tgattaccc | agatatatct | atgaaaacca | 1560 |
| gtggcttcca | tcaaacccttt | gccaactcag | gttcacagca | gctttgggca | gttatggcag | 1620 |

```
tatggcatta gctgagaggt gtctgccact tctgggtcaa tggaataata aattaagtac   1680
aggcaggaat ttggttggga gcatcttgta tgatctccgt atgatgtgat attgatggag   1740
atagtggtcc tcattcttgg gggttgccat tcccacattc ccccttcaac aaacagtgta   1800
acaggtcctt cccagattta gggtacttt attgatggat atgttttcct tttattcaca    1860
taacccettg aaaccctgtc ttgtcctcct gttacttgct tctgctgtac aagatgtagc   1920
acctttctc ctctttgaac atggtctagt gacacggtag caccagttgc aggaaggagc    1980
cagacttgtt ctcagagcac tgtgttcaca cttttcagca aaaatagcta tggttgtaac   2040
atatgtattc ccttcctctg atttgaaggc aaaaatctac agtgtttctt cacttctttt   2100
ctgatctggg gcatgaaaaa agcaagattg aaatttgaac tatgagtctc ctgcatggca   2160
acaaaatgtg tgtcaccatc aggccaacag gccagcccett gaatggggat ttattactgt   2220
tgtatctatg ttgcatgata acattcatc accttcctcc tgtagtcctg cctcgtactc    2280
cccttccect atgattgaaa agtaaacaaa acccacattt cctatcctgg ttagaagaaa   2340
attaatgttc tgacagttgt gatcgcctgg agtactttta gacttttagc attcgttttt   2400
tacctgtttg tggatgtgtg tttgtatgtg catacgtatg agataggcac atgcatcttc   2460
tgtatggaca aaggtggggt acctacagga gagcaaaggt taattttgtg cttttagtaa   2520
aaacatttaa atacaaagtt ctttattggg tggaattata tttgatgcaa atatttgatc   2580
acttaaaact tttaaaactt ctaggtaatt tgccacgctt tttgactgct caccaatacc   2640
ctgtaaaaat acgtaattct tcctgtttgt gtaataagat attcatattt gtagttgcat   2700
taataatagt tatttcttag tccatcagat gttcccgtgt gcctctttta tgccaaattg   2760
attgtcatat ttcatgttgg gaccaagtag tttgcccatg gcaaacctaa atttatgacc   2820
tgctgaggcc tctcagaaaa ctgagcatac tagcaagaca gctcttcttg aaaaaaaaaa   2880
tatgtataca caaatatata cgtatatcta tatacgta tgtatataca cacatgtata    2940
ttcttccttg attgtgtagc tgtccaaaat aataacatat atagagggag ctgtattcct   3000
ttatacaaat ctgatggctc ctgcagcact ttttccttct gaaaatattt acattttgct   3060
aacctagttt gttactttaa aaatcagttt tgatgaaagg agggaaaagc agatggactt   3120
gaaaaagatc caagctccta ttagaaaagg tatgaaaatc tttatagtaa aattttttat   3180
aaactaaagt tgtacctttt aatatgtagt aaactctcat ttatttgggg ttcgctcttg   3240
gatctcatcc atccattgtg ttctctttaa tgctgcctgc cttttgaggc attcactgcc   3300
ctagacaatg ccaccagaga tagtgggga aatgccagat gaaaccaact cttgctctca    3360
ctagttgtca gcttctctgg ataagtgacc acagaagcag gagtcctcct gcttgggcat   3420
cattgggcca gttccttctc tttaaatcag atttgtaatg ctcccaaat tccatcacat    3480
cacatttaaa ttgcagacag tgttttgcac atcatgtatc tgttttgtcc cataatatgc   3540
tttttactcc ctgatcccag tttctgctgt tgactcttcc attcagtttt atttattgtg   3600
tgttctcaca gtgacaccat ttgtcctttt ctgcaacaac ctttccagct acttttgcca   3660
aattctattt gtcttctcct tcaaaacatt ctcctttgca gttcctcttc atctgtgtag   3720
ctgctctttt gtctcttaac ttaccattcc tatagtactt tatgcatctc tgcttagttc   3780
tattagtttt ttggccttgc tcttctcctt gattttaaaa ttccttctat agctagagct   3840
tttctttctt tcattctctc ttcctgcagt gttttgcata catcagaagc taggtacata   3900
agttaaatga ttgagagttg gctgtattta gatttatcac ttttaatag ggtgagcttg    3960
agagttttct ttctttctgt tttttttttt tgtttttttt tttttttttt tttttttttt   4020
```

```
ttttgactaa tttcacatgc tctaaaaacc ttcaaaggtg attattttc tcctggaaac    4080 tccaggtcca ttctgtttaa atccctaaga atgtcagaat taaaataaca gggctatccc    4140
gtaattggaa atatttcttt tttcaggatg ctatagtcaa tttagtaagt gaccaccaaa    4200
ttgttatttg cactaacaaa gctcaaaaca cgataagttt actcctccat ctcagtaata    4260
aaaattaagc tgtaatcaac cttctaggtt tctcttgtct taaaatgggt attcaaaaat    4320
ggggatctgt ggtgtatgta tggaaacaca tactccttaa tttacctgtt gttgaaaact    4380
ggagaaatga ttgtcgggca accgttatt ttttattgta ttttatttgg ttgagggatt     4440 ttttataaa cagttttact tgtgtcatat tttaaaatta ctaactgcca tcacctgctg      4500
gggtcctttg ttaggtcatt ttcagtgact aatagggata atccaggtaa ctttgaagag    4560
atgagcagtg agtgaccagg cagttttct gcctttagct ttgacagttc ttaattaaga     4620
tcattgaaga ccagctttct cataaatttc tcttttgaa aaaagaaag catttgtact      4680 aagctcctct gtaagacaac atcttaaatc ttaaagtgt tgttatcatg actggtgaga     4740
gaagaaaaca ttttgttttt attaaatgga gcattattta caaaaagcca ttgttgagaa    4800
ttagatccca catcgtataa atatctatta accattctaa ataagagaa ctccagtgtt     4860 gctatgtgca agatcctctc ttggagcttt tttgcatagc aattaaaggt gtgctatttg    4920
tcagtagcca tttttttgca gtgatttgaa gaccaaagtt gttttacagc tgtgttaccg    4980
ttaaaggttt tttttttat atgtattaaa tcaatttatc actgtttaaa gctttgaata    5040
tctgcaatct ttgccaaggt acttttttat ttaaaaaaaa acataacttt gtaaatatta    5100
ccctgtaata ttatatatac ttaataaaac attttaagct attttgttgg gctatttcta    5160
ttgctgctac agcagaccac aagcacattt ctgaaaaatt taatttatta atgtattttt    5220
aagttgctta tattctaggt aacaatgtaa agaatgattt aaaatattaa ttatgaattt    5280
tttgagtata atacccaata agcttttaat tagagcagag ttttaattaa aagtttaaa     5340 tcagtc                                                               5346
```

<210> SEQ ID NO 16
<211> LENGTH: 323
<212> TYPE: PRT
<213> ORGANISM: Homo sapiens

<400> SEQUENCE: 16

```
Met Trp Pro Leu Val Ala Ala Leu Leu Leu Gly Ser Ala Cys Cys Gly
  1               5                  10                  15

Ser Ala Gln Leu Leu Phe Asn Lys Thr Lys Ser Val Glu Phe Thr Phe
                 20                  25                  30

Cys Asn Asp Thr Val Val Ile Pro Cys Phe Val Thr Asn Met Glu Ala
             35                  40                  45

Gln Asn Thr Thr Glu Val Tyr Val Lys Trp Lys Phe Lys Gly Arg Asp
         50                  55                  60

Ile Tyr Thr Phe Asp Gly Ala Leu Asn Lys Ser Thr Val Pro Thr Asp
 65                  70                  75                  80

Phe Ser Ser Ala Lys Ile Glu Val Ser Gln Leu Leu Lys Gly Asp Ala
                 85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
            115                 120                 125
```

```
Leu Lys Tyr Arg Val Val Ser Trp Phe Ser Pro Asn Glu Asn Ile Leu
        130                 135                 140

Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Gly Met Asp Glu Lys Thr
                165                 170                 175

Ile Ala Leu Leu Val Ala Gly Leu Val Ile Thr Val Ile Val Ile Val
                180                 185                 190

Gly Ala Ile Leu Phe Val Pro Gly Glu Tyr Ser Leu Lys Asn Ala Thr
                195                 200                 205

Gly Leu Gly Leu Ile Val Thr Ser Thr Gly Ile Leu Ile Leu Leu His
        210                 215                 220

Tyr Tyr Val Phe Ser Thr Ala Ile Gly Leu Thr Ser Phe Val Ile Ala
225                 230                 235                 240

Ile Leu Val Ile Gln Val Ile Ala Tyr Ile Leu Ala Val Val Gly Leu
                245                 250                 255

Ser Leu Cys Ile Ala Ala Cys Ile Pro Met His Gly Pro Leu Leu Ile
                260                 265                 270

Ser Gly Leu Ser Ile Leu Ala Leu Ala Gln Leu Leu Gly Leu Val Tyr
        275                 280                 285

Met Lys Phe Val Ala Ser Asn Gln Lys Thr Ile Gln Pro Pro Arg Lys
        290                 295                 300

Ala Val Glu Glu Pro Leu Asn Ala Phe Lys Glu Ser Lys Gly Met Met
305                 310                 315                 320

Asn Asp Glu

<210> SEQ ID NO 17
<211> LENGTH: 293
<212> TYPE: PRT
<213> ORGANISM: Artificial Sequence
<220> FEATURE:
<223> OTHER INFORMATION: Synthetic polypeptide

<400> SEQUENCE: 17

Met Trp Pro Leu Ala Ala Ala Leu Leu Leu Gly Ser Cys Cys Cys Gly
1               5                   10                  15

Ser Ala Gln Leu Leu Phe Asn Lys Thr Lys Ser Val Glu Phe Thr Phe
                20                  25                  30

Cys Asn Asp Thr Val Val Ile Pro Cys Phe Val Thr Asn Met Glu Ala
                35                  40                  45

Gln Asn Thr Thr Glu Val Tyr Val Lys Trp Lys Phe Lys Gly Arg Asp
        50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
                100                 105                 110

Thr Cys Glu Val Thr Glu Leu Thr Arg Glu Gly Glu Thr Ile Ile Glu
                115                 120                 125

Leu Lys Tyr Arg Val Val Ser Trp Phe Ser Pro Asn Glu Asn Ile Leu
        130                 135                 140

Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Gly Met Asp Glu Lys Thr
```

```
            165                 170                 175
Ile Ala Leu Leu Val Ala Gly Leu Val Ile Thr Val Ile Val Ile Val
            180                 185                 190

Gly Ala Ile Leu Phe Val Pro Gly Glu Tyr Ser Leu Lys Asn Ala Thr
            195                 200                 205

Gly Leu Gly Leu Ile Val Thr Ser Thr Gly Ile Leu Ile Leu Leu His
            210                 215                 220

Tyr Tyr Val Phe Ser Thr Ala Ile Gly Leu Thr Ser Phe Val Ile Ala
225                 230                 235                 240

Ile Leu Val Ile Gln Val Ile Ala Tyr Ile Leu Ala Val Val Gly Leu
            245                 250                 255

Ser Leu Cys Ile Ala Ala Cys Ile Pro Met His Gly Pro Leu Leu Ile
            260                 265                 270

Ser Gly Leu Ser Ile Leu Ala Leu Ala Gln Leu Leu Gly Leu Val Tyr
            275                 280                 285

Met Lys Phe Val Glu
            290

<210> SEQ ID NO 18
<211> LENGTH: 305
<212> TYPE: PRT
<213> ORGANISM: Artificial Sequence
<220> FEATURE:
<223> OTHER INFORMATION: Synthetic polypeptide

<400> SEQUENCE: 18

Met Trp Pro Leu Ala Ala Leu Leu Leu Gly Ser Cys Cys Cys Gly
1               5                   10                  15

Ser Ala Gln Leu Leu Phe Asn Lys Thr Lys Ser Val Glu Phe Thr Phe
            20                  25                  30

Cys Asn Asp Thr Val Val Ile Pro Cys Phe Val Thr Asn Met Glu Ala
            35                  40                  45

Gln Asn Thr Thr Glu Val Tyr Val Lys Trp Lys Phe Lys Gly Arg Asp
            50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
            115                 120                 125

Leu Lys Tyr Arg Val Val Ser Trp Phe Ser Pro Asn Glu Asn Ile Leu
            130                 135                 140

Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Gly Met Asp Glu Lys Thr
            165                 170                 175

Ile Ala Leu Leu Val Ala Gly Leu Val Ile Thr Val Ile Val Ile Val
            180                 185                 190

Gly Ala Ile Leu Phe Val Pro Gly Glu Tyr Ser Leu Lys Asn Ala Thr
            195                 200                 205

Gly Leu Gly Leu Ile Val Thr Ser Thr Gly Ile Leu Ile Leu Leu His
            210                 215                 220

Tyr Tyr Val Phe Ser Thr Ala Ile Gly Leu Thr Ser Phe Val Ile Ala
```

```
225                 230                 235                 240

Ile Leu Val Ile Gln Val Ile Ala Tyr Ile Leu Ala Val Val Gly Leu
                245                 250                 255

Ser Leu Cys Ile Ala Ala Cys Ile Pro Met His Gly Pro Leu Leu Ile
                260                 265                 270

Ser Gly Leu Ser Ile Leu Ala Leu Ala Gln Leu Leu Gly Leu Val Tyr
                275                 280                 285

Met Lys Phe Val Ala Ser Asn Gln Arg Thr Ile Gln Pro Pro Arg Asn
                290                 295                 300

Arg
305

<210> SEQ ID NO 19
<211> LENGTH: 312
<212> TYPE: PRT
<213> ORGANISM: Artificial Sequence
<220> FEATURE:
<223> OTHER INFORMATION: Synthetic polypeptide

<400> SEQUENCE: 19

Met Trp Pro Leu Ala Ala Leu Leu Leu Gly Ser Cys Cys Cys Gly
1               5                   10                  15

Ser Ala Gln Leu Leu Phe Asn Lys Thr Lys Ser Val Glu Phe Thr Phe
                20                  25                  30

Cys Asn Asp Thr Val Val Ile Pro Cys Phe Val Thr Asn Met Glu Ala
                35                  40                  45

Gln Asn Thr Thr Glu Val Tyr Val Lys Trp Lys Phe Lys Gly Arg Asp
    50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
                100                 105                 110

Thr Cys Glu Val Thr Glu Leu Thr Arg Glu Gly Glu Thr Ile Ile Glu
                115                 120                 125

Leu Lys Tyr Arg Val Val Ser Trp Phe Ser Pro Asn Glu Asn Ile Leu
    130                 135                 140

Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Gly Met Asp Glu Lys Thr
                165                 170                 175

Ile Ala Leu Leu Val Ala Gly Leu Val Ile Thr Val Ile Val Ile Val
                180                 185                 190

Gly Ala Ile Leu Phe Val Pro Gly Glu Tyr Ser Leu Lys Asn Ala Thr
                195                 200                 205

Gly Leu Gly Leu Ile Val Thr Ser Thr Gly Ile Leu Ile Leu Leu His
    210                 215                 220

Tyr Tyr Val Phe Ser Thr Ala Ile Gly Leu Thr Ser Phe Val Ile Ala
225                 230                 235                 240

Ile Leu Val Ile Gln Val Ile Ala Tyr Ile Leu Ala Val Val Gly Leu
                245                 250                 255

Ser Leu Cys Ile Ala Ala Cys Ile Pro Met His Gly Pro Leu Leu Ile
                260                 265                 270

Ser Gly Leu Ser Ile Leu Ala Leu Ala Gln Leu Leu Gly Leu Val Tyr
```

```
            275                 280                 285
Met Lys Phe Val Ala Ser Asn Gln Arg Thr Ile Gln Pro Pro Arg Lys
    290                 295                 300

Ala Val Glu Glu Pro Leu Asn Glu
305                 310

<210> SEQ ID NO 20
<211> LENGTH: 323
<212> TYPE: PRT
<213> ORGANISM: Artificial Sequence
<220> FEATURE:
<223> OTHER INFORMATION: Synthetic polypeptide

<400> SEQUENCE: 20

Met Trp Pro Leu Ala Ala Leu Leu Leu Gly Ser Cys Cys Cys Gly
1               5                   10                  15

Ser Ala Gln Leu Leu Phe Asn Lys Thr Lys Ser Val Glu Phe Thr Phe
                20                  25                  30

Cys Asn Asp Thr Val Val Ile Pro Cys Phe Val Thr Asn Met Glu Ala
            35                  40                  45

Gln Asn Thr Thr Glu Val Tyr Val Lys Trp Lys Phe Lys Gly Arg Asp
        50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
        115                 120                 125

Leu Lys Tyr Arg Val Val Ser Trp Phe Ser Pro Asn Glu Asn Ile Leu
130                 135                 140

Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Gly Met Asp Glu Lys Thr
                165                 170                 175

Ile Ala Leu Leu Val Ala Gly Leu Val Ile Thr Val Ile Val Ile Val
            180                 185                 190

Gly Ala Ile Leu Phe Val Pro Gly Glu Tyr Ser Leu Lys Asn Ala Thr
        195                 200                 205

Gly Leu Gly Leu Ile Val Thr Ser Thr Gly Ile Leu Ile Leu Leu His
    210                 215                 220

Tyr Tyr Val Phe Ser Thr Ala Ile Gly Leu Thr Ser Phe Val Ile Ala
225                 230                 235                 240

Ile Leu Val Ile Gln Val Ile Ala Tyr Ile Leu Ala Val Val Gly Leu
                245                 250                 255

Ser Leu Cys Ile Ala Ala Cys Ile Pro Met His Gly Pro Leu Leu Ile
            260                 265                 270

Ser Gly Leu Ser Ile Leu Ala Leu Ala Gln Leu Leu Gly Leu Val Tyr
        275                 280                 285

Met Lys Phe Val Ala Ser Asn Gln Arg Thr Ile Gln Pro Pro Arg Lys
    290                 295                 300

Ala Val Glu Glu Pro Leu Asn Ala Phe Lys Glu Ser Lys Gly Met Met
305                 310                 315                 320

Asn Asp Glu
```

<210> SEQ ID NO 21
<211> LENGTH: 22
<212> TYPE: DNA
<213> ORGANISM: Artificial Sequence
<220> FEATURE:
<223> OTHER INFORMATION: Synthetic primer

<400> SEQUENCE: 21
tgcagaagtc actaggagga at                                    22

<210> SEQ ID NO 22
<211> LENGTH: 27
<212> TYPE: DNA
<213> ORGANISM: Artificial Sequence
<220> FEATURE:
<223> OTHER INFORMATION: Synthetic probe

<400> SEQUENCE: 22
tcagtcaact tcttctgggt tgtttcc                               27

<210> SEQ ID NO 23
<211> LENGTH: 23
<212> TYPE: DNA
<213> ORGANISM: Artificial Sequence
<220> FEATURE:
<223> OTHER INFORMATION: Synthetic primer

<400> SEQUENCE: 23
gtgccagact cactttctat cca                                   23

<210> SEQ ID NO 24
<211> LENGTH: 22
<212> TYPE: DNA
<213> ORGANISM: Artificial Sequence
<220> FEATURE:
<223> OTHER INFORMATION: Synthetic primer

<400> SEQUENCE: 24
tgctgccaat atacggcttc tg                                    22

<210> SEQ ID NO 25
<211> LENGTH: 26
<212> TYPE: DNA
<213> ORGANISM: Artificial Sequence
<220> FEATURE:
<223> OTHER INFORMATION: Synthetic probe

<400> SEQUENCE: 25
cagctctcat agccaactat ggtgcc                                26

<210> SEQ ID NO 26
<211> LENGTH: 22
<212> TYPE: DNA
<213> ORGANISM: Artificial Sequence
<220> FEATURE:
<223> OTHER INFORMATION: Synthetic primer

<400> SEQUENCE: 26
tcaagcagag cctggttatc tg                                    22

<210> SEQ ID NO 27
<211> LENGTH: 23
<212> TYPE: DNA
<213> ORGANISM: Artificial Sequence
<220> FEATURE:

<223> OTHER INFORMATION: Synthetic primer

<400> SEQUENCE: 27
gtcgtcattc catgctttgt tac                                               23

<210> SEQ ID NO 28
<211> LENGTH: 30
<212> TYPE: DNA
<213> ORGANISM: Artificial Sequence
<220> FEATURE:
<223> OTHER INFORMATION: Synthetic probe

<400> SEQUENCE: 28
tggaggcaca aaacactact gaagtatacg                                        30

<210> SEQ ID NO 29
<211> LENGTH: 22
<212> TYPE: DNA
<213> ORGANISM: Artificial Sequence
<220> FEATURE:
<223> OTHER INFORMATION: Synthetic primer

<400> SEQUENCE: 29
ggacagtgga cttgtttaga gc                                                22

<210> SEQ ID NO 30
<211> LENGTH: 21
<212> TYPE: DNA
<213> ORGANISM: Artificial Sequence
<220> FEATURE:
<223> OTHER INFORMATION: Synthetic primer

<400> SEQUENCE: 30
ggcttggtgg ctgattgttc t                                                 21

<210> SEQ ID NO 31
<211> LENGTH: 28
<212> TYPE: DNA
<213> ORGANISM: Artificial Sequence
<220> FEATURE:
<223> OTHER INFORMATION: Synthetic probe

<400> SEQUENCE: 31
agcacccaaa ctgatatgcc tgtatttg                                          28

<210> SEQ ID NO 32
<211> LENGTH: 23
<212> TYPE: DNA
<213> ORGANISM: Artificial Sequence
<220> FEATURE:
<223> OTHER INFORMATION: Synthetic primer

<400> SEQUENCE: 32
tgggaactgg tgtttcaagt cta                                               23

<210> SEQ ID NO 33
<211> LENGTH: 158
<212> TYPE: DNA
<213> ORGANISM: Artificial Sequence
<220> FEATURE:
<223> OTHER INFORMATION: Synthetic polynucleotide

<400> SEQUENCE: 33
gcagacatga ttacttcaga gctttcaaag ctagatactg taccttgcat attccaacac       60
gcgatcgcat tttaagattt tccatcctag tggaaagata tgatttgatt catcctattt      120

```
<210> SEQ ID NO 34
<211> LENGTH: 160
<212> TYPE: DNA
<213> ORGANISM: Artificial Sequence
<220> FEATURE:
<223> OTHER INFORMATION: Synthetic polynucleotide

<400> SEQUENCE: 34
ggatccattt taagtaatag aataggattt ttaattgttc cagtgtttct gtgatagagc    60
tgtcctgcac agacctgttt ctcgagataa cttcgtataa tgtatgctat acgaagttat   120
atgcatggcc tccgcgccgg gttttggcgc ctcccgcggg                         160

<210> SEQ ID NO 35
<211> LENGTH: 160
<212> TYPE: DNA
<213> ORGANISM: Artificial Sequence
<220> FEATURE:
<223> OTHER INFORMATION: Synthetic polynucleotide

<400> SEQUENCE: 35
catgtctgga ataacttcgt ataatgtatg ctatacgaag ttatgctagt aactataacg    60
gtcctaaggt agcgactagc attagtatgg aaggtccgtc cactgtccag gttcctcttg   120
cggagctctt tgtctctctg gactctgtat acactgcttg                         160

<210> SEQ ID NO 36
<211> LENGTH: 239
<212> TYPE: DNA
<213> ORGANISM: Artificial Sequence
<220> FEATURE:
<223> OTHER INFORMATION: Synthetic polynucleotide

<400> SEQUENCE: 36
ggatccattt taagtaatag aataggattt ttaattgttc cagtgtttct gtgatagagc    60
tgtcctgcac agacctgttt ctcgagataa cttcgtataa tgtatgctat acgaagttat   120
gctagtaact ataacggtcc taaggtagcg actagcatta gtatggaagg tccgtccact   180
gtccaggttc ctcttgcgga gctctttgtc tctctggact ctgtatacac tgcttgcat    239
```
actttgtata ttaaagtaca gtagaacctg ccactttt                            158

METHOD OF USING MOUSE HAVING A HUMANIZED CLUSTER OF DIFFERENTIATION 47 GENE

CROSS-REFERENCE TO RELATED APPLICATIONS

This application is a continuation of U.S. patent application Ser. No. 14/951,825, filed Nov. 25, 2015, which claims the benefit of U.S. Provisional Patent Application Ser. No. 62/087,992, filed Dec. 5, 2014, which is incorporated herein by reference in its entirety.

INCORPORATION BY REFERENCE OF SEQUENCE LISTING

10021 The Sequence Listing in the ASCII text file, named as 10108US03_32584Y_SequenceListing.txt of 92 KB, created on May 1, 2018, and submitted to the United States Patent and Trademark Office via EFS-Web, is incorporated herein by reference.

BACKGROUND

Cancer therapy can be separated into four main categories: chemo/radio therapy, hormone therapy, targeted therapy, and immunotherapy. An intense focus of medical research and development has focused on targeted therapy and significant improvements have been made, yet cancer remains a major challenge to patients and to the healthcare industry worldwide. This major challenge is due, in part, to the ability of cancer cells to evade the monitoring mechanisms of the innate and adaptive immune systems, which is partly the result of inhibition of phagocytic clearance. Currently, no in vivo system exists to optimally determine the therapeutic potential of new cancer therapies that are designed to activate phagocytic clearance of cancer cells and determine the molecular aspects of how cancer cells provide inhibitory signals to macrophages and phagocytic cells. Such a system provides a source for assays in phagocytosis and macrophage functions in vivo, and identification of new cancer therapies that are targeted at providing an anti-tumor environment by promoting pro-phagocytic signals to the immune system.

SUMMARY

The present invention encompasses the recognition that it is desirable to engineer non-human animals to permit improved systems for identifying and developing new cancer therapeutics. The present invention also encompasses the recognition that it is desirable to engineer non-human animals to permit improved engraftment of human hematopoietic stem cells. Further, the present invention also encompasses the recognition that non-human animals having a humanized CD47 gene and/or otherwise expressing, containing, or producing a human or humanized CD47 polypeptide are desirable, for example for use in identifying and developing cancer therapeutics that overcome systemic toxicity associated with blockade of CD47 and overcome CD47-mediated inhibition of phagocytosis of tumor cells, and provide a more efficient in vivo system for engraftment of human hemotopoietic stem cells that provides an increase in homeostasis of a broader number of human cell types.

In some embodiments, the present invention provides a non-human animal having a genome comprising a CD47 gene that includes genetic material from two different species (e.g., a human and a non-human). In some embodiments, the CD47 gene of the non-human animals as described herein encodes a CD47 polypeptide that contains human and non-human portions, wherein the human and non-human portions are linked together and form a functional CD47 polypeptide.

In some embodiments, a non-human animal of the present invention comprises a CD47 gene that comprises an endogenous portion and a human portion, wherein the endogenous and human portions are operably linked to an endogenous promoter.

In some embodiments, an endogenous portion comprises exon 1 and the exons downstream of exon 7 of an endogenous CD47 gene. In some certain embodiments, exon 1 and the exons downstream of exon 7 of an endogenous CD47 gene are at least 50%, at least 55%, at least 60%, at least 65%, at least 70%, at least 75%, at least 80%, at least 85%, at least 90%, at least 95%, or at least 98% identical to the corresponding exon 1 and the exons downstream of exon 7 of a mouse CD47 gene that appears in Table 3. In some embodiments, exon 1 and the exons downstream of exon 7 of an endogenous CD47 gene are identical to the corresponding exon 1 and the exons downstream of exon 7 of a mouse CD47 gene that appears in Table 3.

In some embodiments, a human portion encodes amino acids 16-292 of a human CD47 polypeptide. In some embodiments, a human portion encodes amino acids 19-292 of a human CD47 polypeptide. In some embodiments, a human portion encodes amino acides 19-141 of a human CD47 polypeptide. In some embodiments, a human portion encodes amino acids 19-127 of a human CD47 polypeptide. In some embodiments, a human portion comprises exons 2-7 of a human CD47 gene.

In some embodiments, exons 2-7 of a human CD47 gene are at least 50%, at least 55%, at least 60%, at least 65%, at least 70°, at least 75%, at least 80%, at least 85%, at least 90%, at least 95%, or at least 98% identical to the corresponding exons 2-7 of a human CD47 gene that appears in Table 3. In some embodiments, exons 2-7 of a human CD47 gene are identical to the corresponding exons 2-7 of a human CD47 gene that appears in Table 3.

In some embodiments, a non-human animal of the present invention expresses a CD47 polypeptide comprising an extracellular portion of a human CD47 polypeptide and an intracellular portion of an endogenous CD47 polypeptide. In some embodiments, a CD47 polypeptide comprises a transmembrane portion of a human CD47 polypeptide. In other embodiments, a CD47 polypeptide comprises a transmembrane portion of a non-human CD47 polypeptide. In some embodiments, a CD47 polypeptide is translated in a cell of a non-human animal with a non-human signal peptide. In some certain embodiments, a non-human signal peptide is a rodent (e.g., a mouse or a rat) signal peptide.

In some embodiments, a CD47 polypeptide of the present invention is expressed from an endogenous non-human CD47 gene.

In some embodiments, an intracellular portion of an endogenous CD47 polypeptide comprises an intracytoplasmic tail that has an amino acid sequence that is at least 50%, at least 55%, at least 60%, at least 65%, at least 70%, at least 75%, at least 80%, at least 85%, at least 90%, at least 95%, or at least 98% identical to an intracytoplasmic tail of a mouse CD47 polypeptide that appears in Table 3. In some embodiments, an intracellular portion of the endogenous CD47 polypeptide comprises an intracytoplasmic tail that has an amino acid sequence that is identical to an intracytoplasmic tail of a mouse CD47 polypeptide that appears in Table 3.

In some embodiments, an extracellular portion of a human CD47 polypeptide comprises amino acids corresponding to residues 19-141 of a human CD47 polypeptide. In some embodiments, an extracellular portion of a human CD47 polypeptide comprises amino acids corresponding to residues 19-127 of a human CD47 polypeptide. In some embodiments, the extracellular portion of a human CD47 polypeptide comprises an amino acid sequence that is at least 500%, at least 55%, at least 60%, at least 65%, at least 70%, at least 75%, at least 80%, at least 85%, at least 90%, at least 95%, or at least 98% identical to a corresponding amino acid sequence of an extracellular portion of a human CD47 polypeptide that appears in Table 3. In some embodiments, an extracellular portion of a human CD47 polypeptide comprises an amino acid sequence that is identical to a corresponding amino acid sequence of an extracellular portion of a human CD47 polypeptide that appears in Table 3.

In some embodiments, the present invention provides a CD47 polypeptide encoded by the CD47 gene of a non-human animal as described herein. In some certain embodiments, an encoded CD47 polypeptide comprises an amino acid sequence that is at least 50%, at least 55%, at least 60%, at least 65%, at least 70%, at least 75%, at least 80%, at least 85%, at least 90%, at least 95%, or at least 98% identical to SEQ ID NO: 17, SEQ ID NO: 18, SEQ ID NO: 19 or SEQ ID NO: 20. In some certain embodiments, an encoded CD47 polypeptide comprises an amino acid sequence that is identical to SEQ ID NO: 17, SEQ ID NO: 18, SEQ ID NO: 19 or SEQ ID NO: 20.

In some embodiments, the present invention provides a humanized CD47 gene comprising one or more exons of a non-human CD47 gene operably linked to one or more exons of a human CD47 gene. In some certain embodiments, a humanized CD47 gene of the present invention comprises non-human exons that encode an intracellular portion of a CD47 polypeptide and human exons that encode an extracellular portion of a human CD47 polypeptide. In some embodiments, a humanized CD47 gene also comprises human exons that encode a transmembrane portion of a human CD47 polypeptide. In some certain embodiments, a humanized CD47 gene of the present invention comprises non-human exons that encode a signal peptide, in whole or in part, and an intracellular portion of a CD47 polypeptide, and human exons that encode an extracellular portion and optionally a transmembrane portion of a CD47 polypeptide.

In some embodiments, the present invention provides an isolated cell or tissue from a non-human animal as described herein. In some embodiments, the present invention provides an isolated cell or tissue comprising a CD47 gene as described herein. In some embodiments, a cell is selected from a dendritic cell, lymphocyte (e.g., a B or T cell), macrophage and a monocyte. In some embodiments, a tissue is selected from adipose, bladder, brain, breast, bone marrow, eye, heart, intestine, kidney, liver, lung, lymph node, muscle, pancreas, plasma, serum, skin, spleen, stomach, thymus, testis, ovum, and a combination thereof.

In some embodiments, the present invention provides a non-human embryonic stem cell whose genome comprises a CD47 gene as described herein. In some embodiments, a non-human embryonic stem cell is a mouse embryonic stem cell and is from a 129 strain, C57BL/6 strain or a BALB/c strain. In some embodiments, a non-human embryonic stem cell is a mouse embryonic stem cell and is from a mixture of 129 and C57BL/6 strains.

In some embodiments, the present invention provides the use of a non-human embryonic stem cell as described herein to make a non-human animal. In some certain embodiments, a non-human embryonic stem cell is a mouse embryonic stem cell and is used to make a mouse comprising a CD47 gene as described herein. In some certain embodiments, a non-human embryonic stem cell is a rat embryonic stem cell and is used to make a rat comprising a CD47 gene as described herein.

In some embodiments, the present invention provides a non-human embryo comprising, made from, obtained from, or generated from a non-human embryonic stem cell comprising a CD47 gene as described herein. In some certain embodiments, a non-human embryo is a rodent embryo. In some embodiments, a rodent embryo is a mouse embryo. In some embodiments, a rodent embryo is a rat embryo.

In some embodiments, the present invention provides a method of making a non-human animal that expresses a CD47 polypeptide from an endogenous CD47 gene, wherein the CD47 polypeptide comprises a human sequence, the method comprising inserting a genomic fragment into an endogenous CD47 gene in a non-human embryonic stem cell, said genomic fragment comprising a nucleotide sequence that encodes a human CD47 polypeptide in whole or in part; obtaining a non-human embryonic stem cell comprising an endogenous CD47 gene that comprises the nucleotide sequence that encodes a human CD47 polypeptide in whole or in part; and creating a non-human animal using the non-human embryonic stem cell comprising said nucleotide sequence that encodes a human CD47 polypeptide in whole or in part.

In some embodiments, a human sequence comprises amino acids corresponding to residues 19-141 (or 19-292) of a human CD47 polypeptide. In some embodiments, a human sequence comprises amino acids corresponding to residues 19-127 of a human CD47 polypeptide.

In some embodiments, a nucleotide sequence comprises exons 2-7 of a human CD47 gene. In some embodiments, a nucleotide sequence comprises one or more selection markers. In some embodiments, a nucleotide sequence comprises one or more site-specific recombination sites.

In some embodiments, the method further comprises a step of inserting a genomic fragment into an endogenous SIRPα gene of a non-human embryonic stem cell, said genomic fragment comprising a nucleotide sequence that encodes a human SIRPα polypeptide in whole or in part (e.g., encodes an extracellular portion of a human SIRPα polypeptide). In some certain embodiments, a genomic fragment comprising a nucleotide sequence that encodes a human SIRPα polypeptidein whole or in part (e.g., encodes an extracellular portion of a human SIRPα polypeptide) is inserted into an endogenous SIRPα gene of the non-human embryonic stem cell prior to an insertion into an endogenous CD47 gene.

In some embodiments, the method further comprises breeding a non-human animal comprising an endogenous CD47 gene that includes a nucleotide sequence that encodes a human CD47 polypeptide, in whole or in part, with a second non-human animal, said second non-human animal having a genome comprising a SIRPα gene that encodes a SIRPα polypeptide comprising an extracellular portion of a human SIRPα polypeptide (e.g., amino acids corresponding to residues 28-362 of a human SIRPα polypeptide) and an intracellular portion of an endogenous SIRPα polypeptide.

In some embodiments, the present invention provides a method of providing a non-human animal whose genome comprises a CD47 gene that encodes an extracellular portion of a human CD47 polypeptide linked to an intracellular portion of an endogenous CD47 polypeptide, the method comprising modifying the genome of a non-human animal so that it comprises a CD47 gene that encodes the extracellular portion of a human CD47 polypeptide linked to the intracellular portion of an endogenous CD47 polypeptide thereby providing said non-human animal. In some embodiments, a CD47 gene encodes a CD47 polypeptide that comprises an extracellular portion and a transmembrane portion of a human CD47 polypeptide linked to an intracellular portion of an endogenous non-human CD47 polypeptide. In other embodiments, a CD47 gene encodes a CD47 polypeptide that comprises an extracellular portion of a human CD47 polypeptide linked to a transmembrane portion and an intracellular portion of an endogenous non-human CD47 polypeptide.

In some embodiments, the modifying the genome of a non-human animal is performed in a non-human embryonic stem cell. In some certain embodiments, the non-human embryonic stem cell is a rodent embryonic stem cell; in some embodiments, a mouse embryonic stem cell; in some embodiments, a rat embryonic stem cell.

In some embodiments, the method further comprises modifying the genome of the non-human animal so that it comprises a SIRPα gene that encodes the extracellular portion of a human SIRPα polypeptide (e.g., amino acids corresponding to residues 28-362 of a human SIRPα polypeptide) linked to the intracellular portion of an endogenous SIRPα polypeptide. In some certain embodiments, the modifying the genome of the non-human animal so that it comprises a SIRPα gene that encodes the extracellular portion of a human SIRPα polypeptide (e.g., amino acids corresponding to residues 28-362 of a human SIRPα polypeptide) linked to the intracellular portion of an endogenous SIRPα polypeptide is performed prior to modifying the genome of the non-human animal so that it comprises a CD47 gene that encodes the extracellular portion and optionally a transmembrane portion of a human CD47 polypeptide linked to the intracellular portion of an endogenous CD47 polypeptide.

In some embodiments, the method further comprises breeding a non-human animal whose genome comprises a CD47 gene that encodes an extracellular portion of a human CD47 polypeptide linked to an intracellular portion of an endogenous CD47 polypeptide with a second non-human animal, said second non-human animal having a genome comprising a SIRPα gene that encodes a SIRPα polypeptide comprising an extracellular portion of a human SIRPα polypeptide (e.g., amino acids corresponding to residues 28-362 of a human SIRPα polypeptide) and an intracellular portion of an endogenous SIRPα polypeptide.

In some embodiments, the present invention provides a non-human animal obtainable by methods as described herein.

In some embodiments, the present invention provides a method of engrafting human cells into a non-human animal, the method comprising steps of providing a non-human animal whose genome comprises a CD47 gene that encodes the extracellular portion of a human CD47 polypeptide linked to the intracellular portion of an endogenous CD47 polypeptide; and transplanting one or more human cells into said non-human animal. In some certain embodiments, the method further comprises a step of assaying engraftment of the one or more human cells in said non-human animal. In some certain embodiments, a step of assaying comprises comparing the engraftment of the one or more human cells to the engraftment in one or more wild-type non-human animals or in one or more non-human animals whose genome does not comprise a CD47 gene that encodes the extracellular portion of a human CD47 polypeptide linked to the intracellular portion of an endogenous CD47 polypeptide.

In some embodiments, human cells are hematopoietic stem cells. In some embodiments, human cells are transplanted intravenously. In some embodiments, human cells are transplanted intraperitoneally. In some embodiments, human cells are transplanted subcutaneously.

In some embodiments, the present invention provides a method of assessing the therapeutic efficacy of a drug targeting human cells, the method comprising providing a non-human animal whose genome comprises a CD47 gene that encodes an extracellular portion of a human CD47 polypeptide linked to an intracellular portion of an endogenous CD47 polypeptide; transplanting one or more human cells into said non-human animal; administering a drug candidate to said non-human animal; and monitoring the human cells in the non-human animal to determine the therapeutic efficacy of the drug candidate.

In some embodiments, human cells are cancer cells and the drug candidate is an anti-cancer drug candidate. In some certain embodiments, a drug candidate is an antibody.

In some embodiments, a non-human animal further comprises human immune cells. In some certain embodiments, a drug candidate is a bi-specific antibody that binds human CD47 and an antigen on transplanted human cancer cells.

In some embodiments, the present invention provides a method comprising providing one or more cells whose genome includes a CD47 gene that encodes an extracellular portion of a human CD47 polypeptide linked to an intracellular portion of an endogenous CD47 polypeptide; incubating the one or more cells with a labeled substrate; and measuring phagocytosis of the labeled substrate by the one or more cells. In some embodiments, the substrate is fluorescently labeled. In some embodiments, the substrate is labeled with an antibody. In some embodiments, the substrate is one or more red blood cells. In some embodiments, the substrate is one or more bacterial cells. In some embodiments, the substrate is one or more tumor cells.

In some embodiments, the present invention provides a method comprising providing a non-human animal whose genome includes a CD47 gene that encodes an extracellular portion of a human CD47 polypeptide linked to an intracellular portion of an endogenous CD47 polypeptide; exposing the non-human animal to an antigen; and measuring phagocytosis of the antigen by one or more cells of the non-human animal. In some embodiments, the step of exposing comprises exposing the non-human animal to an antigen that is fluorescently labeled. In some embodiments, the step of exposing comprises exposing the non-human animal to one or more cells that comprise the antigen. In some embodiments, the step of exposing comprises exposing the non-human animal to one or more human cells comprising the antigen or to one or more bacterial cells comprising the antigen. In some embodiments, the step of exposing comprises exposing the non-human animal to one or more cells that have been transformed with the antigen so that the antigen is expressed on the surface of the one or more transformed cells. In some embodiments, the step of exposing comprises exposing the non-human animal to one or more tumor cells that comprise the antigen.

In some embodiments, the present invention provides methods for identification or validation of a drug or vaccine, the method comprising the steps of delivering a drug or vaccine to a non-human animal whose genome includes a CD47 gene that encodes an extracellular portion of a human CD47 polypeptide linked to an intracellular portion of an endogenous CD47 polypeptide, and monitoring one or more of the immune response to the drug or vaccine, the safety profile of the drug or vaccine, or the effect on a disease or condition. In some embodiments, monitoring the safety profile includes determining if the non-human animal exhibits a side effect or adverse reaction as a result of delivering the drug or vaccine. In some embodiments, a side effect or adverse reaction is selected from morbidity, mortality, alteration in body weight, alteration of the level of one or more enzymes (e.g., liver), alteration in the weight of one or more organs, loss of function (e.g., sensory, motor, organ, etc.), increased susceptibility to one or more diseases, alterations to the genome of the non-human animal, increase or decrease in food consumption and complications of one or more diseases.

In some embodiments, the present invention provides use of a non-human animal as described herein in the development of a drug or vaccine for use in medicine, such as use as a medicament.

In some embodiments, the present invention provides use of a non-human animal as described herein in the manufacture of a medicament for the treatment of cancer or a neoplasm.

In some embodiments, the present invention provides use of a non-human animal as described herein to assess the efficacy of a therapeutic drug targeting human cells. In various embodiments, a non-human animal of the present invention is transplanted with human cells and a drug candidate targeting said human cells is administered to the animal. In some embodiments, efficacy of the drug is determined by monitoring the human cells in the non-human animal after the administration of the drug.

In some embodiments, the present invention provides a non-human animal or cell as described herein for use in the development and/or identification of a drug (e.g., an antibody) for therapy or diagnosis.

In some embodiments, the present invention provides a non-human animal or cell as described herein for use in the development and/or identification of a drug (e.g., an antibody) for the treatment, prevention or amelioration of cancer or a neoplasm.

In some embodiments, the present invention provides a method of assessing the pharmacokinetics of a drug targeting human CD47, the method comprising the steps of administering the drug to a non-human animal as described herein, and performing an assay to determine one or more pharmacokinetic properties of the drug targeting human CD47.

In some embodiments, the present invention provides a method of assessing the on-target toxicity of a drug targeting human CD47, the method comprising the steps of administering the drug to a non-human animal as described herein, and performing an assay for one or more parameters associated with on-target toxicity of a drug.

In some embodiments, the present invention provides a method of assessing the off-target toxicity of a drug targeting human CD47, the method comprising the steps of administering the drug to a non-human animal as described herein, and performing an assay for one or more parameters associated with off-target toxicity of a drug.

In many embodiments, a non-human animal as described herein is a rodent whose genome includes a CD47 gene that encodes an extracellular portion of a human CD47 polypeptide linked to an intracellular portion of an endogenous CD47 polypeptide; in some embodiments, a rodent is a mouse; in some embodiments, a rodent is a rat.

In some embodiments, a drug targeting human CD47 is a CD47 antagonist. In some certain embodiments, a CD47 antagonist is an anti-CD47 antibody. In some embodiments, a drug targeting human CD47 is a CD47 agonist.

In various embodiments, a CD47 gene of the present invention includes a CD47 gene as described herein. In various embodiments, a CD47 polypeptide of the present invention includes a CD47 polypeptide as described herein.

In various embodiments, a non-human animal of the present invention does not detectably express a full-length endogenous non-human CD47 polypeptide. In various embodiments, a non-human animal of the present invention does not detectably express an extracellular portion of an endogenous CD47 polypeptide. In various embodiments, a non-human animal of the present invention does not detectably express an extracellular portion of both an endogenous CD47 polypeptide and an endogenous SIRPα polypeptide.

In various embodiments, an extracellular portion of a human CD47 polypeptide comprises amino acids corresponding to residues 19-141 of a human CD47 polypeptide as described herein.

In various embodiments, an N-terminal immunoglobulin V domain of a human CD47 polypeptide comprises amino acids corresponding to residues 19-127 of a human CD47 polypeptide as described herein.

In various embodiments, non-human animals, cells, tissues, embryonic stem cells and/or embryos of the present invention have a genome that further comprises a SIRPα gene that encodes a SIRPα polypeptide comprising an extracellular portion of a human SIRPα polypeptide (e.g., amino acids corresponding to residues 28-362 of a human SIRPα polypeptide) and an intracellular portion of an endogenous SIRPα polypeptide.

In various embodiments, a non-human animal of the present invention is a rodent; in some embodiments, a mouse; in some embodiments, a rat.

As used in this application, the terms "about" and "approximately" are used as equivalents. Any numerals used in this application with or without about/approximately are meant to cover any normal fluctuations appreciated by one of ordinary skill in the relevant art.

Other features, objects, and advantages of the present invention are apparent in the detailed description that follows. It should be understood, however, that the detailed description, while indicating embodiments of the present invention, is given by way of illustration only, not limitation. Various changes and modifications within the scope of the invention will become apparent to those skilled in the art from the detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The Drawings included herein, which are composed of the following Figures, are for illustration purposes only and not for limitation.

DEFINITIONS

Figure 1:
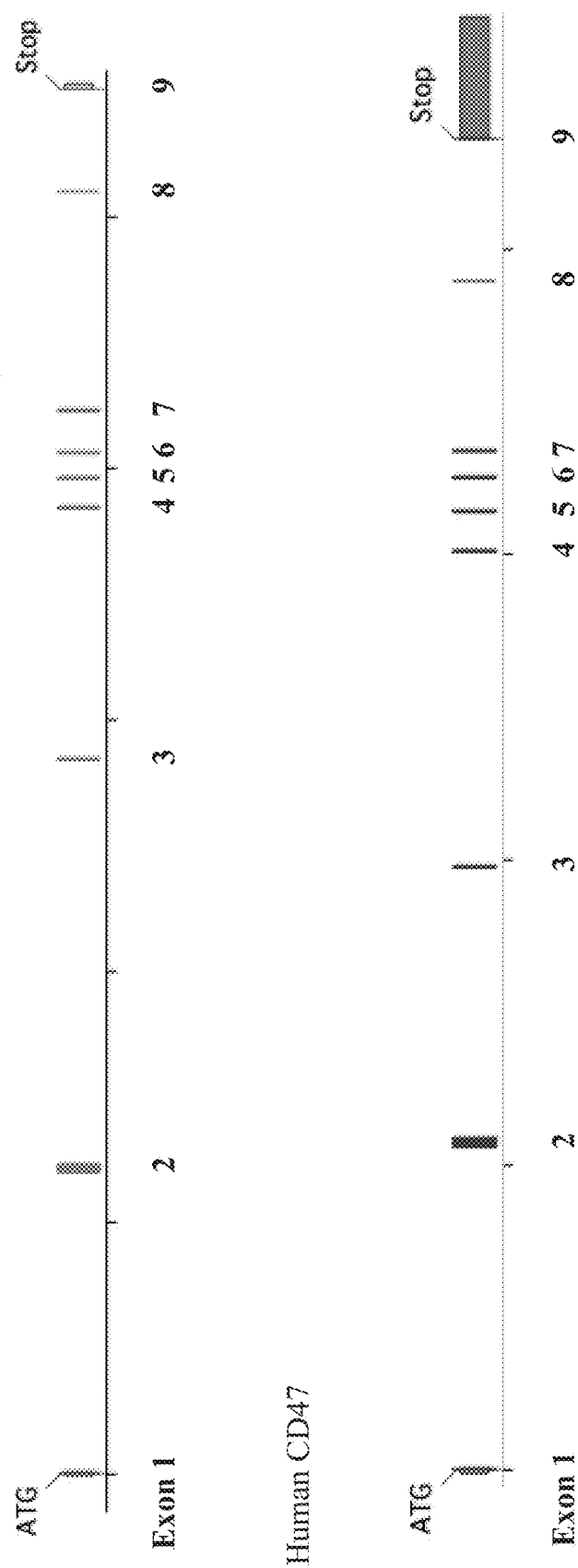
FIG. 1 shows a diagram, not to scale, of the genomic organization of a non-human (e.g., mouse) and human Cluster of Differentiation 47 (CD47) genes. Exons are numbered beneath each exon.

This invention is not limited to particular methods and experimental conditions described herein, as such methods and conditions may vary. It is also to be understood that the terminology used herein is for the purpose of describing particular embodiments only, and is not intended to be limiting, since the scope of the present invention is defined by the claims.

Unless defined otherwise, all terms and phrases used herein include the meanings that the terms and phrases have attained in the art, unless the contrary is clearly indicated or clearly apparent from the context in which the term or phrase is used. Although any methods and materials similar or equivalent to those described herein can be used in the practice or testing of the present invention, particular methods and materials are now described. All publications mentioned herein are hereby incorporated by reference.

The term "approximately", as applied herein to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

The term "biologically active", as used herein, refers to a characteristic of any agent that has activity in a biological system, in vitro or in vivo (e.g., in an organism). For instance, an agent that, when present in an organism, has a biological effect within that organism, is considered to be biologically active. In particular embodiments, where a protein or polypeptide is biologically active, a portion of that protein or polypeptide that shares at least one biological activity of the protein or polypeptide is typically referred to as a "biologically active" portion.

The term "comparable", as used herein, refers to two or more agents, entities, situations, sets of conditions, etc. that may not be identical to one another but that are sufficiently similar to permit comparison there between so that conclusions may reasonably be drawn based on differences or similarities observed. Those of ordinary skill in the art will understand, in context, what degree of identity is required in any given circumstance for two or more such agents, entities, situations, sets of conditions, etc. to be considered comparable.

The term "conservative", as used herein to describe a conservative amino acid substitution, refers to substitution of an amino acid residue by another amino acid residue having a side chain R group with similar chemical properties (e.g., charge or hydrophobicity). In general, a conservative amino acid substitution will not substantially change the functional properties of interest of a protein, for example, the ability of a receptor to bind to a ligand. Examples of groups of amino acids that have side chains with similar chemical properties include: aliphatic side chains such as glycine, alanine, valine, leucine, and isoleucine; aliphatic-hydroxyl side chains such as serine and threonine; amide-containing side chains such as asparagine and glutamine; aromatic side chains such as phenylalanine, tyrosine, and tryptophan; basic side chains such as lysine, arginine, and histidine; acidic side chains such as aspartic acid and glutamic acid; and, sulfur-containing side chains such as cysteine and methionine. Conservative amino acids substitution groups include, for example, valine/leucine/isoleucine, phenylalanine/tyrosine, lysine/arginine, alanine/valine, glutamate/aspartate, and asparagine/glutamine. In some embodiments, a conservative amino acid substitution can be a substitution of any native residue in a protein with alanine, as used in, for example, alanine scanning mutagenesis. In some embodiments, a conservative substitution is made that has a positive value in the PAM250 log-likelihood matrix disclosed in Gonnet et al. (1992) Exhaustive Matching of the Entire Protein Sequence Database, *Science* 256:1443-45, hereby incorporated by reference. In some embodiments, the substitution is a moderately conservative substitution wherein the substitution has a nonnegative value in the PAM250 log-likelihood matrix.

The term "control", as used herein, refers to the art-understood meaning of a "control" being a standard against which results are compared. Typically, controls are used to augment integrity in experiments by isolating variables in order to make a conclusion about such variables. In some embodiments, a control is a reaction or assay that is performed simultaneously with a test reaction or assay to provide a comparator. As used herein, a "control" may refer to a "control animal". A "control animal" may have a modification as described herein, a modification that is different as described herein, or no modification (i.e., a wild-type animal). In one experiment, the "test" (i.e., the variable being tested) is applied. In the second experiment, the "control," the variable being tested is not applied. In some embodiments, a control is a historical control (i.e., of a test or assay performed previously, or an amount or result that is previously known). In some embodiments, a control is or comprises a printed or otherwise saved record. A control may be a positive control or a negative control.

The term "disruption", as used herein, refers to the result of a homologous recombination event with a DNA molecule (e.g., with an endogenous homologous sequence such as a gene or gene locus. In some embodiments, a disruption may achieve or represent an insertion, deletion, substitution, replacement, missense mutation, or a frame-shift of a DNA sequence(s), or any combination thereof. Insertions may include the insertion of entire genes or fragments of genes, e.g., exons, which may be of an origin other than the endogenous sequence (e.g., a heterologous sequence). In some embodiments, a disruption may increase expression and/or activity of a gene or gene product (e.g., of a protein encoded by a gene). In some embodiments, a disruption may decrease expression and/or activity of a gene or gene product. In some embodiments, a disruption may alter sequence of a gene or an encoded gene product (e.g., an encoded protein). In some embodiments, a disruption may truncate or fragment a gene or an encoded gene product (e.g., an encoded protein). In some embodiments, a disruption may extend a gene or an encoded gene product; in some such embodiments, a disruption may achieve assembly of a fusion protein. In some embodiments, a disruption may affect level but not activity of a gene or gene product. In some embodiments, a disruption may affect activity but not level of a gene or gene product. In some embodiments, a disruption may have no significant effect on level of a gene or gene product. In some embodiments, a disruption may have no significant effect on activity of a gene or gene product. In some embodiments, a disruption may have no significant effect on either level or activity of a gene or gene product.

The terms "determining", "measuring", "evaluating", "assessing", "assaying" and "analyzing" are used interchangeably herein to refer to any form of measurement, and include determining if an element is present or not. These terms include both quantitative and/or qualitative determinations. Assaying may be relative or absolute. "Assaying for the presence of" can be determining the amount of something present and/or determining whether or not it is present or absent.

The phrase "endogenous locus" or "endogenous gene", as used herein, refers to a genetic locus found in a parent or reference organism prior to introduction of a disruption, deletion, replacement, alteration, or modification as described herein. In some embodiments, the endogenous locus has a sequence found in nature. In some embodiments, the endogenous locus is a wild type locus. In some embodiments, the reference organism is a wild-type organism. In some embodiments, the reference organism is an engineered organism. In some embodiments, the reference organism is a laboratory-bred organism (whether wild-type or engineered).

The phrase "endogenous promoter" refers to a promoter that is naturally associated, e.g., in a wild-type organism, with an endogenous gene.

The term "heterologous", as used herein, refers to an agent or entity from a different source. For example, when used in reference to a polypeptide, gene, or gene product or present in a particular cell or organism, the term clarifies that the relevant polypeptide, gene, or gene product: 1) was engineered by the hand of man; 2) was introduced into the cell or organism (or a precursor thereof) through the hand of man (e.g., via genetic engineering); and/or 3) is not naturally produced by or present in the relevant cell or organism (e.g., the relevant cell type or organism type).

The term "host cell", as used herein, refers to a cell into which a heterologous (e.g., exogenous) nucleic acid or protein has been introduced. Persons of skill upon reading this disclosure will understand that such terms refer not only to the particular subject cell, but also is used to refer to the progeny of such a cell. Because certain modifications may occur in succeeding generations due to either mutation or environmental influences, such progeny may not, in fact, be identical to the parent cell, but are still included within the scope of the term "host cell" as used herein. In some embodiments, a host cell is or comprises a prokaryotic or eukaryotic cell. In general, a host cell is any cell that is suitable for receiving and/or producing a heterologous nucleic acid or protein, regardless of the Kingdom of life to which the cell is designated. Exemplary cells include those of prokaryotes and eukaryotes (single-cell or multiple-cell), bacterial cells (e.g., strains of E. coli, Bacillus spp., Streptomyces spp., etc.), mycobacteria cells, fungal cells, yeast cells (e.g., S. cerevisiae, S. pombe, P. pastoris, P. methanolica, etc.), plant cells, insect cells (e.g., SF-9, SF-21, baculovirus-infected insect cells, Trichoplusia ni, etc.), non-human animal cells, human cells, or cell fusions such as, for example, hybridomas or quadromas. In some embodiments, the cell is a human, monkey, ape, hamster, rat, or mouse cell. In some embodiments, the cell is eukaryotic and is selected from the following cells: CHO (e.g., CHO KI, DXB-1 CHO, Veggie-CHO), COS (e.g., COS-7), retinal cell, Vero, CV1, kidney (e.g., HEK293, 293 EBNA, MSR 293, MDCK, HaK, BHK), HeLa, HepG2, W138, MRC 5, Colo205, HB 8065, HL-60, (e.g., BHK21), Jurkat, Daudi, A431 (epidermal), CV-1, U937, 3T3, L cell, C127 cell, SP2/0, NS-0, MMT 060562, Sertoli cell, BRL 3A cell, HT 1080 cell, myeloma cell, tumor cell, and a cell line derived from an aforementioned cell. In some embodiments, the cell comprises one or more viral genes, e.g., a retinal cell that expresses a viral gene (e.g., a PER.C6™ cell). In some embodiments, a host cell is or comprises an isolated cell. In some embodiments, a host cell is part of a tissue. In some embodiments, a host cell is part of an organism.

The term "humanized", is used herein in accordance with its art-understood meaning to refer to nucleic acids or proteins whose structures (i.e., nucleotide or amino acid sequences) include portions that correspond substantially or identically with structures of a particular gene or protein found in nature in a non-human animal, and also include portions that differ from that found in the relevant particular non-human gene or protein and instead correspond more closely with comparable structures found in a corresponding human gene or protein. In some embodiments, a "humanized" gene is one that encodes a polypeptide having substantially the amino acid sequence as that of a human polypeptide (e.g., a human protein or portion thereof—e.g., characteristic portion thereof). To give but one example, in the case of a membrane receptor, a "humanized" gene may encode a polypeptide having an extracellular portion having an amino acid sequence as that of a human extracellular portion and the remaining sequence as that of a non-human (e.g., mouse) polypeptide. In some embodiments, a humanized gene comprises at least a portion of a DNA sequence of a human gene. In some embodiment, a humanized gene comprises an entire DNA sequence of a human gene. In some embodiments, a humanized protein comprises a sequence having a portion that appears in a human protein. In some embodiments, a humanized protein comprises an entire sequence of a human protein and is expressed from an endogenous locus of a non-human animal that corresponds to the homolog or ortholog of the human gene.

The term "identity", as used herein in connection with a comparison of sequences, refers to identity as determined by a number of different algorithms known in the art that can be used to measure nucleotide and/or amino acid sequence identity. In some embodiments, identities as described herein are determined using a ClustalW v. 1.83 (slow) alignment employing an open gap penalty of 10.0, an extend gap penalty of 0.1, and using a Gonnet similarity matrix (MACVECTOR™ 10.0.2, MacVector Inc., 2008).

The term "isolated", as used herein, refers to a substance and/or entity that has been (1) separated from at least some of the components with which it was associated when initially produced (whether in nature and/or in an experimental setting), and/or (2) designed, produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99% o, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. In some embodiments, as will be understood by those skilled in the art, a substance may still be considered "isolated' or even'pure", after having been combined with certain other components such as, for example, one or more carriers or excipients (e.g., buffer, solvent, water, etc.); in such embodiments, percent isolation or purity of the substance is calculated without including such carriers or excipients. To give but one example, in some embodiments, a biological polymer such as a polypeptide or polynucleotide that occurs in nature is considered to be "isolated" when: a) by virtue of its origin or source of derivation is not associated with some or all of the components that accompany it in its native state in nature; b) it is substantially free of other polypeptides or nucleic acids of the same species from the species that produces it in nature; or c) is expressed by or is otherwise in association with components from a cell or other expression system that is not of the species that produces it in nature. Thus, for instance, in some embodiments, a polypeptide that is chemically synthesized or is synthesized in a cellular system different from that which produces it in nature is considered to be an "isolated" polypeptide. Alternatively or additionally, in some embodiments, a polypeptide that has been subjected to one or more purification techniques may be considered to be an "isolated" polypeptide to the extent that it has been separated from other components: a) with which it is associated in nature; and/or b) with which it was associated when initially produced.

The phrase "non-human animal", as used herein, refers to any vertebrate organism that is not a human. In some embodiments, a non-human animal is acyclostome, a bony fish, a cartilaginous fish (e.g., a shark or a ray), an amphibian, a reptile, a mammal, or a bird. In some embodiments, a non-human mammal is a primate, a goat, a sheep, a pig, a dog, a cow, or a rodent. In some embodiments, a non-human animal is a rodent such as a rat or a mouse.

The phrase "nucleic acid", as used herein, in its broadest sense, refers to any compound and/or substance that is or can be incorporated into an oligonucleotide chain. In some embodiments, a "nucleic acid" is a compound and/or substance that is or can be incorporated into an oligonucleotide chain via a phosphodiester linkage. As will be clear from context, in some embodiments, "nucleic acid" refers to individual nucleic acid residues (e.g., nucleotides and/or nucleosides); in some embodiments, "nucleic acid" refers to an oligonucleotide chain comprising individual nucleic acid residues. In some embodiments, a "nucleic acid" is or comprises RNA; in some embodiments, a "nucleic acid" is or comprises DNA. In some embodiments, a "nucleic acid" is, comprises, or consists of one or more natural nucleic acid residues. In some embodiments, a "nucleic acid" is, comprises, or consists of one or more nucleic acid analogs. In some embodiments, a nucleic acid analog differs from a "nucleic acid" in that it does not utilize a phosphodiester backbone. For example, in some embodiments, a "nucleic acid" is, comprises, or consists of one or more "peptide nucleic acids", which are known in the art and have peptide bonds instead of phosphodiester bonds in the backbone, are considered within the scope of the present invention. Alternatively or additionally, in some embodiments, a "nucleic acid" has one or more phosphorothioate and/or 5'-N-phosphoramidite linkages rather than phosphodiester bonds. In some embodiments, a "nucleic acid" is, comprises, or consists of one or more natural nucleosides (e.g., adenosine, thymidine, guanosine, cytidine, uridine, deoxyadenosine, deoxythymidine, deoxyguanosine, and deoxycytidine). In some embodiments, a "nucleic acid" is, comprises, or consists of one or more nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, 2-thiocytidine, methylated bases, intercalated bases, and combinations thereof). In some embodiments, a "nucleic acid" comprises one or more modified sugars (e.g., 2'-fluororibose, ribose, 2'-deoxyribose, arabinose, and hexose) as compared with those in natural nucleic acids. In some embodiments, a "nucleic acid" has a nucleotide sequence that encodes a functional gene product such as an RNA or protein. In some embodiments, a "nucleic acid" includes one or more introns. In some embodiments, a "nucleic acid" is prepared by one or more of isolation from a natural source, enzymatic synthesis by polymerization based on a complementary template (in vivo or in vitro), reproduction in a recombinant cell or system, and chemical synthesis. In some embodiments, a "nucleic acid" is at least 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000 or more residues long. In some embodiments, a "nucleic acid" is single stranded; in some embodiments, a "nucleic acid" is double stranded. In some embodiments, a "nucleic acid" has a nucleotide sequence comprising at least one element that encodes, or is the complement of a sequence that encodes, a polypeptide. In some embodiments, a "nucleic acid" has enzymatic activity.

The phrase "operably linked", as used herein, refers to a juxtaposition wherein the components described are in a relationship permitting them to function in their intended manner. A control sequence "operably linked" to a coding sequence is ligated in such a way that expression of the coding sequence is achieved under conditions compatible with the control sequences. "Operably linked" sequences include both expression control sequences that are contiguous with the gene of interest and expression control sequences that act in trans or at a distance to control the gene of interest. The term "expression control sequence", as used herein, refers to polynucleotide sequences, which are necessary to effect the expression and processing of coding sequences to which they are ligated. "Expression control sequences" include: appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism. For example, in prokaryotes, such control sequences generally include promoter, ribosomal binding site, and transcription termination sequence, while in eukaryotes, typically, such control sequences include promoters and transcription termination sequence. The term "control sequences" is intended to include components whose presence is essential for expression and processing, and can also include additional components whose presence is advantageous, for example, leader sequences and fusion partner sequences.

The term "polypeptide", as used herein, refers to any polymeric chain of amino acids. In some embodiments, a polypeptide has an amino acid sequence that occurs in nature. In some embodiments, a polypeptide has an amino acid sequence that does not occur in nature. In some embodiments, a polypeptide has an amino acid sequence that contains portions that occur in nature separately from one another (i.e., from two or more different organisms, for example, human and non-human portions). In some embodiments, a polypeptide has an amino acid sequence that is engineered in that it is designed and/or produced through action of the hand of man.

The term "recombinant", as used herein, is intended to refer to polypeptides (e.g., CD47polypeptides as described herein) that are designed, engineered, prepared, expressed, created or isolated by recombinant means, such as polypeptides expressed using a recombinant expression vector transfected into a host cell, polypeptides isolated from a recombinant, combinatorial human polypeptide library (Hoogenboom H. R., (1997) *TIB Tech.* 15:62-70; Azzazy H., and Highsmith W. E., (2002) *Clin. Biochem.* 35:425-445; Gavilondo J. V., and Larrick J. W. (2002) *BioTechniques* 29:128-145; Hoogenboom H., and Chames P. (2000) *Immunology Today* 21:371-378), antibodies isolated from an animal (e.g., a mouse) that is transgenic for human immunoglobulin genes (see e.g., Taylor, L. D., et al. (1992) *Nucl. Acids Res.* 20:6287-6295; Kellermann S-A., and Green L. L. (2002) *Current Opinion in Biotechnology* 13:593-597; Little M. et al. (2000) *Immunology Today* 21:364-370; Murphy, A. J., et al. (2014) *Proc. Natl. Acad. Sci. U.S.A* 111(14):5153-5158) or polypeptides prepared, expressed, created or isolated by any other means that involves splicing selected sequence elements to one another. In some embodiments, one or more of such selected sequence elements is found in nature. In some embodiments, one or more of such selected sequence elements is designed in silico. In some embodiments, one or more such selected sequence elements result from mutagenesis (e.g., in vivo or in vitro) of a known sequence element, e.g., from a natural or synthetic source. For example, in some embodiments, a recombinant polypeptide is comprised of sequences found in the genome of a source organism of interest (e.g., human, mouse, etc.). In some embodiments, a recombinant polypeptide has an amino acid sequence that resulted from mutagenesis (e.g., in vitro or in vivo, for example in a non-human animal), so that the amino acid sequences of the recombinant polypeptides are sequences that, while originating from and related to polypeptides sequences, may not naturally exist within the genome of a non-human animal in vivo.

The term "replacement" is used herein to refer to a process through which a "replaced" nucleic acid sequence (e.g., a gene) found in a host locus (e.g., in a genome) is removed from that locus, and a different, "replacement" nucleic acid is located in its place. In some embodiments, the replaced nucleic acid sequence and the replacement nucleic acid sequences are comparable to one another in that, for example, they are homologous to one another and/or contain corresponding elements (e.g., protein-coding elements, regulatory elements, etc.). In some embodiments, a replaced nucleic acid sequence includes one or more of a promoter, an enhancer, a splice donor site, a splice receiver site, an intron, an exon, an untranslated region (UTR); in some embodiments, a replacement nucleic acid sequence includes one or more coding sequences. In some embodiments, a replacement nucleic acid sequence is a homolog of the replaced nucleic acid sequence. In some embodiments, a replacement nucleic acid sequence is an ortholog of the replaced sequence. In some embodiments, a replacement nucleic acid sequence is or comprises a human nucleic acid sequence. In some embodiments, including where the replacement nucleic acid sequence is or comprises a human nucleic acid sequence, the replaced nucleic acid sequence is or comprises a rodent sequence (e.g., a mouse or rat sequence). The nucleic acid sequence so placed may include one or more regulatory sequences that are part of source nucleic acid sequence used to obtain the sequence so placed (e.g., promoters, enhancers, 5'- or 3'-untranslated regions, etc.). For example, in various embodiments, the replacement is a substitution of an endogenous sequence with a heterologous sequence that results in the production of a gene product from the nucleic acid sequence so placed (comprising the heterologous sequence), but not expression of the endogenous sequence; the replacement is of an endogenous genomic sequence with a nucleic acid sequence that encodes a protein that has a similar function as a protein encoded by the endogenous sequence (e.g., the endogenous genomic sequence encodes a CD47 protein, and the DNA fragment encodes one or more human CD47 proteins). In various embodiments, an endogenous gene or fragment thereof is replaced with a corresponding human gene or fragment thereof. A corresponding human gene or fragment thereof is a human gene or fragment that is an ortholog of, or is substantially similar or the same in structure and/or function, as the endogenous gene or fragment thereof that is replaced.

The phrase "cluster of differentiation 47protein" or "CD47 protein", as used herein, refers to a multi-pass transmembrane protein that belongs to the immunoglobulin superfamily and has an extracellular amino-terminal immunoglobulin V domain, five transmembrane domains and a short carboxyl-terminal intracellular tail. CD47 is expressed on the cell surface and is involved in interactions between membrane surface proteins such as, for example, integrins, SIRPα and thrombospondin-1 (TSP-1). CD47 is expressed in normal tissues and up-regulated in many human cancers. CD47 has been shown to be involved in several cellular processes such as, for example, apoptosis, proliferation, adhesion and migration. Several alternatively spliced CD47 isoforms have been identified between mouse and man. By way of illustration, nucleotide and amino acid sequences of mouse and human CD47 genes are provided in Table 3. Persons of skill upon reading this disclosure will recognize that one or more endogenous CD47 genes in a genome (or all) can be replaced by one or more heterologous CD47 genes (e.g., polymorphic variants, subtypes or mutants, genes from another species, humanized forms, etc.).

A "CD47-expressing cell", as used herein, refers to a cell that expresses a CD47 transmembrane protein. In some embodiments, a CD47-expressing cell expresses a CD47 transmembrane protein on its surface. In some embodiments, a CD47 protein expressed on the surface of the cell in an amount sufficient to mediate cell-to-cell interactions via the CD47 transmembrane protein expressed on the surface of the cell. Exemplary CD47-expressing cells include neurons, immune cells, keratinocytes, and circulating cells. CD47-expressing cells regulate the interaction of immune cells and circulating cells to regulate various cellular processes such as adhesion, cell proliferation and/or apoptosis, angiogenesis and inflammation. In some embodiments, non-human animals of the present invention demonstrate regulation of various cellular processes (as described herein) via humanized CD47 proteins expressed on the surface of one more cells of the non-human animal.

The term "reference" is used herein to describe a standard or control agent, cohort, individual, population, sample, sequence or value against which an agent, animal, cohort, individual, population, sample, sequence or value of interest is compared. In some embodiments, a reference agent, cohort, individual, population, sample, sequence or value is tested and/or determined substantially simultaneously with the testing or determination of the agent, cohort, individual, population, sample, sequence or value of interest. In some embodiments, a reference agent, cohort, individual, population, sample, sequence or value is a historical reference, optionally embodied in a tangible medium. In some embodiments, a reference may refer to a control. As used herein, a "reference" may refer to a "reference animal". A "reference animal" may have a modification as described herein, a modification that is different as described herein or no modification (i.e., a wild-type animal). Typically, as would be understood by those skilled in the art, a reference agent, animal, cohort, individual, population, sample, sequence or value is determined or characterized under conditions comparable to those utilized to determine or characterize the agent, animal (e.g., a mammal), cohort, individual, population, sample, sequence or value of interest.

The term "substantially", as used herein, refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

The phrase "substantial homology", as used herein, refers to a comparison between amino acid or nucleic acid sequences. As will be appreciated by those of ordinary skill in the art, two sequences are generally considered to be "substantially homologous" if they contain homologous residues in corresponding positions. Homologous residues may be identical residues. Alternatively, homologous residues may be non-identical residues will appropriately similar structural and/or functional characteristics. For example, as is well known by those of ordinary skill in the art, certain amino acids are typically classified as "hydrophobic" or "hydrophilic" amino acids, and/or as having "polar" or "non-polar" side chains. Substitution of one amino acid for another of the same type may often be considered a "homologous" substitution. Typical amino acid categorizations are summarized in Table I and 2.

TABLE 1

| Alanine | Ala | A | Nonpolar | Neutral | 1.8 |
| Arginine | Arg | R | Polar | Positive | −4.5 |
| Asparagine | Asn | N | Polar | Neutral | −3.5 |
| Aspartic acid | Asp | D | Polar | Negative | −3.5 |
| Cysteine | Cys | C | Nonpolar | Neutral | 2.5 |
| Glutamic acid | Glu | E | Polar | Negative | −3.5 |
| Glutamine | Gln | Q | Polar | Neutral | −3.5 |
| Glycine | Gly | G | Nonpolar | Neutral | −0.4 |
| Histidine | His | H | Polar | Positive | −3.2 |
| Isoleucine | Ile | I | Nonpolar | Neutral | 4.5 |
| Leucine | Leu | L | Nonpolar | Neutral | 3.8 |
| Lysine | Lys | K | Polar | Positive | −3.9 |
| Methionine | Met | M | Nonpolar | Neutral | 1.9 |
| Phenylalanine | Phe | F | Nonpolar | Neutral | 2.8 |
| Proline | Pro | P | Nonpolar | Neutral | −1.6 |
| Serine | Ser | S | Polar | Neutral | −0.8 |
| Threonine | Thr | T | Polar | Neutral | −0.7 |
| Tryptophan | Trp | W | Nonpolar | Neutral | −0.9 |
| Tyrosine | Tyr | Y | Polar | Neutral | −1.3 |
| Valine | Val | V | Nonpolar | Neutral | 4.2 |

TABLE 2

| Ambiguous Amino Acids | 3-Letter | 1-Letter |
| --- | --- | --- |
| Asparagine or aspartic acid | Asx | B |
| Glutamine or glutamic acid | Glx | Z |
| Leucine or Isoleucine | Xle | J |
| Unspecified or unknown amino acid | Xaa | X |

As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul et al. (1990) Basic local alignment search tool, *J. Mol. Biol.*, 215(3): 403-410; Altschul et al. (1997) Methods in Enzymology; Altschul et al., "Gapped BLAST and PSI-BLAST: a new generation of protein database search programs", *Nucleic Acids Res.* 25:3389-3402; Baxevanis et al. (1998) Bioinformatics: A Practical Guide to the Analysis of Genes and Proteins, Wiley: and Misener et al. (eds.) (1999) Bioinformatics Methods and Protocols (*AMethods in*

*Molecular Biology*, Vol. 132), Humana Press. In addition to identifying homologous sequences, the programs mentioned above typically provide an indication of the degree of homology. In some embodiments, two sequences are considered to be substantially homologous if at least 50%, 55%, 60%, 65%, 70%, 75%, 80%, 85%, 90%, 91%, 92%, 93%, 94%0, 95%, 96%, 97%, 98%, 99% or more of their corresponding residues are homologous over a relevant stretch of residues. In some embodiments, the relevant stretch is a complete sequence. In some embodiments, the relevant stretch is at least 9, 10, 11, 12, 13, 14, 15, 16, 17 or more residues. In some embodiments, the relevant stretch includes contiguous residues along a complete sequence. In some embodiments, the relevant stretch includes discontinuous residues along a complete sequence. In some embodiments, the relevant stretch is at least 10, 15, 20, 25, 30, 35, 40, 45, 50, or more residues.

The phrase "substantial identity", as used herein, refers to a comparison between amino acid or nucleic acid sequences. As will be appreciated by those of ordinary skill in the art, two sequences are generally considered to be "substantially identical" if they contain identical residues in corresponding positions. As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul et al. (1990) Basic local alignment search tool, *J. Mol. Biol.*, 215(3): 403-410; Altschul et al., Methods in Enzymology; Altschul et al. (1997) *Nucleic Acids Res.* 25:3389-3402; Baxevanis et al. (1998) Bioinformatics: A Practical Guide to the Analysis of Genes and Proteins, Wiley; and Misener et al., (eds.) (1999) Bioinformatics Methods and Protocols (*Methods in Molecular Biology*, Vol. 132), Humana Press. In addition to identifying identical sequences, the programs mentioned above typically provide an indication of the degree of identity. In some embodiments, two sequences are considered to be substantially identical if at least 50%, 55%, 60%, 65%, 70%, 75%, 80%, 85%, 90%, 91%, 92%, 93%, 94%, 95%, 96%, 97%, 98%, 99% or more of their corresponding residues are identical over a relevant stretch of residues. In some embodiments, the relevant stretch is a complete sequence. In some embodiments, the relevant stretch is at least 10, 15, 20, 25, 30, 35, 40, 45, 50, or more residues.

The phrase "targeting vector" or "targeting construct", as used herein, refers to a polynucleotide molecule that comprises a targeting region. A targeting region comprises a sequence that is identical or substantially identical to a sequence in a target cell, tissue or animal and provides for integration of the targeting construct into a position within the genome of the cell, tissue or animal via homologous recombination. Targeting regions that target using site-specific recombinase recognition sites (e.g., loxP or Frt sites) are also included. In some embodiments, a targeting construct of the present invention further comprises a nucleic acid sequence or gene of particular interest, a selectable marker, control and or regulatory sequences, and other nucleic acid sequences that allow for recombination mediated through exogenous addition of proteins that aid in or facilitate recombination involving such sequences. In some embodiments, a targeting construct of the present invention further comprises a gene of interest in whole or in part, wherein the gene of interest is a heterologous gene that encodes a protein, in whole or in part, that has a similar function as a protein encoded by an endogenous sequence.

In some embodiments, a targeting construct of the present invention further comprises a humanized gene of interest, in whole or in part, wherein the humanized gene of interest encodes a protein, in whole or in part, that has a similar function as a protein encoded by the endogenous sequence.

The term "variant", as used herein, refers to an entity that shows significant structural identity with a reference entity, but differs structurally from the reference entity in the presence or level of one or more chemical moieties as compared with the reference entity. In many embodiments, a "variant" also differs functionally from its reference entity. In general, whether a particular entity is properly considered to be a "variant" of a reference entity is based on its degree of structural identity with the reference entity. As will be appreciated by those skilled in the art, any biological or chemical reference entity has certain characteristic structural elements. A "variant", by definition, is a distinct chemical entity that shares one or more such characteristic structural elements. To give but a few examples, a small molecule may have a characteristic core structural element (e.g., a macrocycle core) and/or one or more characteristic pendent moieties so that a variant of the small molecule is one that shares the core structural element and the characteristic pendent moieties but differs in other pendent moieties and/or in types of bonds present (single vs. double, E vs. Z, etc.) within the core, a polypeptide may have a characteristic sequence element comprised of a plurality of amino acids having designated positions relative to one another in linear or three-dimensional space and/or contributing to a particular biological function, a nucleic acid may have a characteristic sequence element comprised of a plurality of nucleotide residues having designated positions relative to on another in linear or three-dimensional space. For example, a "variant polypeptide" may differ from a reference polypeptide as a result of one or more differences in amino acid sequence and/or one or more differences in chemical moieties (e.g., carbohydrates, lipids, etc.) covalently attached to the polypeptide backbone. In some embodiments, a "variant polypeptide" shows an overall sequence identity with a reference polypeptide that is at least 85%, 86%, 87%, 88%, 89%, 90%, 91%, 92%, 93%, 94%, 95%, 96%, 97%, or 99%. Alternatively or additionally, in some embodiments, a "variant polypeptide" does not share at least one characteristic sequence element with a reference polypeptide. In some embodiments, the reference polypeptide has one or more biological activities. In some embodiments, a "variant polypeptide" shares one or more of the biological activities of the reference polypeptide. In some embodiments, a "variant polypeptide" lacks one or more of the biological activities of the reference polypeptide. In some embodiments, a "variant polypeptide" shows a reduced level of one or more biological activities as compared with the reference polypeptide. In many embodiments, a polypeptide of interest is considered to be a "variant" of a parent or reference polypeptide if the polypeptide of interest has an amino acid sequence that is identical to that of the parent but for a small number of sequence alterations at particular positions. Typically, fewer than 20%, 15%, 10%, 9%, 8%, 7%, 6%, 5%, 4%, 3%, 2% of the residues in the variant are substituted as compared with the parent. In some embodiments, a "variant" has 10, 9, 8, 7, 6, 5, 4, 3, 2, or 1 substituted residue as compared with a parent. Often, a "variant" has a very small number (e.g., fewer than 5, 4, 3, 2, or 1) number of substituted functional residues (i.e., residues that participate in a particular biological activity). Furthermore, a "variant" typically has not more than 5, 4, 3, 2, or 1 additions or deletions, and often has no additions or deletions, as compared with the parent.

Moreover, any additions or deletions are typically fewer than about 25, about 20, about 19, about 18, about 17, about 16, about 15, about 14, about 13, about 10, about 9, about 8, about 7, about 6, and commonly are fewer than about 5, about 4, about 3, or about 2 residues. In some embodiments, the parent or reference polypeptide is one found in nature. As will be understood by those of ordinary skill in the art, a plurality of variants of a particular polypeptide of interest may commonly be found in nature, particularly when the polypeptide of interest is an infectious agent polypeptide.

The term "vector", as used herein, refers to a nucleic acid molecule capable of transporting another nucleic acid to which it is associated. In some embodiment, vectors are capable of extra-chromosomal replication and/or expression of nucleic acids to which they are linked in a host cell such as a eukaryotic and/or prokaryotic cell. Vectors capable of directing the expression of operatively linked genes are referred to herein as "expression vectors."

The term "wild-type", as used herein, has its art-understood meaning that refers to an entity having a structure and/or activity as found in nature in a "normal" (as contrasted with mutant, diseased, altered, etc.) state or context. Those of ordinary skill in the art will appreciate that wild-type genes and polypeptides often exist in multiple different forms (e.g., alleles).

DETAILED DESCRIPTION OF CERTAIN EMBODIMENTS

The present invention provides, among other things, improved and/or engineered non-human animals having humanized genetic material encoding a cluster of differentiation 47 (CD47) gene for determining the therapeutic efficacy of CD47 antagonists (e.g., an anti-CD47 antibody) for the treatment of cancer, and assays in transplant engraftment, activation and phagocytosis and signal transduction. It is contemplated that such non-human animals provide an improvement in determining the therapeutic efficacy of CD47 antagonists and their potential for CD47 blockade. It is also contemplated that such non-human animals provide an improvement in transplant engraftment of human cells. Therefore, the present invention is particularly useful for the development of anti-CD47 therapies for the treatment of various cancers, as well as for maintaining human hematopoietic cells in non-human animals. In particular, the present invention encompasses the humanization of a murine CD47 gene resulting in expression of a humanized CD47 protein on the surface of cells of the non-human animal. Such humanized CD47 proteins have the capacity to provide a source of human CD47$^+$ cells for determining the efficacy of anti-CD47 therapeutics to activate phagocytosis of tumor cells. Further, such humanized CD47 proteins have the capacity to recognize engrafted human cells via engagement of other cell surface proteins and ligands present on the surface of the engrafted human cells (e.g., SIRPα). In some embodiments, non-human animals of the present invention are capable of activating phagocytosis via blockade of CD47 signaling through the humanized CD47 protein expressed on the surface of cells of the non-human animal. In some embodiments, non-human animals of the present invention are capable of receiving transplanted human hematopoietic cells; in some embodiments, such non-human mammals develop and/or have an immune system comprising human cells. In some embodiments, humanized CD47 proteins have a sequence corresponding to the N-terminal immunoglobulin V domain of a human CD47 protein. In some embodiments, humanized CD47 proteins have a sequence corresponding to an N-terminal portion of a human CD47 protein that comprises an extracellular portion and a transmembrane portion of a human CD47 protein, wherein the extracellular portion includes the N-terminal immunoglobulin V domain of the human CD47 protein and the transmembrane portion includes the five transmembrane domains of the human CD47 protein. In some embodiments, humanized CD47 proteins have a sequence corresponding to the intracytoplasmic tail of a non-human (e.g., murine) CD47 protein. In some embodiments, humanized CD47 proteins have a sequence corresponding to amino acid residues 19-292 (or 19-141, or 19-127) of a human CD47 protein. In some embodiments, non-human animals of the present invention comprise an endogenous CD47 gene that contains genetic material from the non-human animal and a heterologous species (e.g., a human). In some embodiments, non-human animals of the present invention comprise a humanized CD47 gene, wherein the humanized CD47 gene comprises exons of a human CD47 gene that encode an extracellular portion including the N-terminal immunoglobulin V domain of a human CD47 gene. In some embodiments, the humanized CD47 gene comprises human CD47 exons, e.g., exons 2-7, encoding an N-terminal portion of a human CD47 protein that comprises an extracellular portion and a transmembrane portion of a human CD47 protein, wherein the extracellular portion includes the N-terminal immunoglobulin V domain of the human CD47 protein and the transmembrane portion includes the five transmembrane domains of the human CD47 protein. In some embodiments, the humanized CD47 gene comprises non-human CD47 exons that encode the signal peptide, in whole or in part, and the intracytoplasmic tail of a non-human CD47 protein. In some embodiments, the humanized CD47 gene comprises non-human CD47 exon 1 and exon(s) downstream of exon 7 that encode the intracytoplasmic tail and the 3' UTR. Depending on the isoforms, there may be one or more exons downstream of exon 7, with the stop codon and the 3' UTR being present in the last exon for all isoforms. For example, isoform 2 of both mouse and human CD47 shown in Table 3 have two exons downstream of exon 7, designated as exon 8 and 9.

Various aspects of the invention are described in detail in the following sections. The use of sections is not meant to limit the invention. Each section can apply to any aspect of the invention. In this application, the use of "or" means "and/or" unless stated otherwise.

Cluster of Differentiation 47 (CD47) Gene

CD47, originally named integrin-associated protein (IAP) for its role in signal transduction from integrins on immune cells, is a transmembrane protein that includes an N-terminal immunoglobulin V (IgV) domain, five transmembrane domains, and a short C-terminal intracytoplasmic tail. The intracytoplasmic tail differs in length according to four alternatively spliced isoforms that have been identified. CD47 (or IAP) was initially described as being expressed on all tissues (isoform 2), neurons (isoform 4) and keratinocytes and macrophages (isoform 1; see Reinhold et al. (1995)*J. Cell Sci.* 108:3419-3425). Little is known about isoform 3 despite this form having the second longest intracytoplasmic tail among the four isoforms. In addition to integrins, CD47 is known to interact with several other cell surface proteins such as, for example, thrombospondin and members of the SIRP family. Most notably, CD47 interacts with SIRPα and leads to bidirectional signaling that regulates a variety of cell-to-cell responses such as, for example, inhibition of phagocytosis and T cell activation. Indeed, CD47-SIRPα interaction has come into focus in recent years for its role in providing tumor cells with the capacity to evade immune surveillance. CD47 binding to SIRPα normally provides protection through anti-phagocytic signals ("don't eat me") for normal cells. However, it has been discovered that tumors also express anti-phagocytic signals, including CD47, to evade destruction by phagocytosis. Interestingly, CD47 is known to be upregulated in several hematologic cancers and contribute to both the growth and dissemination of tumors (Chao et al. (2012) *Curr Opin Immunol.* 24(2): 225-232).

The complete effects of targeting CD47 and the CD47-SIRP pathway as a new treatment for cancer are unknown and some possible toxicitites have been explored. A more thorough and detailed understanding of CD47 signaling and the CD47-SIRPα pathway is needed to develop better targeted therapies for cancer treatment of the future.

CD47 Sequences

Exemplary CD47 sequences for mouse and human are set forth in Table 3. For mRNA sequences, bold font indicates coding sequence, and consecutive exons, where indicated, are separated by alternating underlined text. For mouse and human protein sequences, signal peptides are underlined, extracellular sequences are bold font and intracytoplasmic sequences are italicized. For humanized protein sequences, non-human sequences are indicated in regular font, human sequences are indicated in bold font, and signal peptides are underlined. As shown, the isoforms differ in the number of exons. For example, isoforms 1-4 of the human CD47 gene have a total of 8, 9, 10 and 11 exons, respectively, with exons 2-7 of each isoform encoding the extracellular domain and the five transmembrane domains.

TABLE 3

```
Mouse CD47 mRNA isoform 1 (XM_006521810.1)
GCCTACACCGGGAGAGCAGGGAGGAGGAGTTGGACTGAGGTTGGGCGGCTC
CGAGGTCCAGGGCGAGCTTGGCCAGAGGGAGTAGAGAGCGCGGGGCTGC
GCAGGGACGCGTGCCGTGAGTTCCGGTGAGCGTGTGTGTCCCATGCTCCCGT
CTTTCAGGCCGGCCCAGGACACGAAGCCGGAAGAGAGCTGGCTGGAGGGAC
GGGGGCCGTGAGCAGAGAGTGCAACCCGCGCAGCCCCGGGGACAGGCTGA
TTCTTGGCGCTCTCCGCCGGAGCCTGCCCAGGGCTGGGTGTGAGGCTGGCGT
CACGTCAACGAGCAGAGGCGGCCAGGCGGGGCGGAGTGCGCGTGCGCGGG
GCGGCGAGCACGCGCGCGCGCGCACCCCCGGGCAGCCTGGGCGGCCGCTCC
TGCCTGTCACTGCTGCGGCGCTGCTGGTCGGTCGTTTCCCTTGAAGGCAGCA
GCGGAGGCGGCGGCTGCTCCAGACACCTGCGGCGGCGACCCCCCGGCGGCG
CGGAGATGTGGCCCTTGGCGGCGGCGCTGTTGCTGGGCTCCTGCTGCT
GCGGTTCAGCTCAACTACTGTTTAGTAACGTCCTCCATAGAGTTCAC
TTCATGCAATGAAACTGTGGTCATCCCTTGCATCGTCCGTAATGTGGAG
GCGCAAAGCACCGAAGAAATGTTTGTGAAGTGGAAGTTGAACAAATCG
TATATTTTCATCTATGATGGAAATAAAAATAGCACTACTACAGATCAAA
ACTTTACCAGTGCAAAAATCTCAGTCTCAGACTTAATCAATGGCATTGC
CTCTTTGAAAATGGATAAGCGCGATGCCATGGTGGGAAACTACACTTGC
GAAGTGACAGAGTTATCCAGAGAAGGCAAAACAGTTATAGAGCTGAAA
AACCGCACGGCCTTCAACACTGACCAAGGATCAGCCTGTTCTTACGAGG
AGGAGAAAGGAGGTTGCAAATTAGTTTCGTGGTTTTCTCCAAATGAAAA
GATCCTCATTGTTATTTTCCCAATTTTGGCTATACTCCTGTTCTGGGGAA
AGTTTGGTATTTTAACACTCAAATATAAATCCAGCCATACGAATAAGAG
AATCATTCTGCTGCTCGTTGCCGGGCTGGTGCTCACAGTCATCGTGGTT
GTTGGAGCCATCCTTCTCATCCCAGGAGAAAAGCCCGTGAAGAATGCTT
CTGGACTTGGCCTCATTTGTAATCTCTACGGGGATATTAATACTACTTCA
GTACAATGTGTTTATGACAGCTTTTGGAATGACCTCTTTCACCATTGCC
ATATTGATCACTCAAGTGCTGGGCTACGTCCTTGCTTTGGTCGGGCTGT
GTCTCTGCATCATGGCATGTGAGCCAGTGCACGGCCCCCTTTTGATTTC
AGGTTTGGGGATCATAGCTCTAGCAGAACTACTTGGATTAGTTTATATG
AAGTTTGTCGAATAGGTGAAGGGAAGTGACGGACTGTAACTTGGAAGTCA
GAAATGGAAGAATACAGTTGTCTAAGCACCAGGTCTTCACGACTCACAGCT
GGAAGGAACAGACAACAGTAACTGACTTCCATCCAGGAAAACATGTCACAT
AAATGATTACTAAGTTTATATTCAAAGCAGCTGTACTTTACATAATAAAAAA
AATATGATGTGCTGTGTAACCAATTGGAATCCCATTTTTCTATTGTTTCTACT
CAACTAGGGGCAAACGTTTCAGGGGCAACTTCCAAGAATGATGCTTGTTAG
ATCCTAGAGTCTCTGAACACTGAGTTTAAATTGATTCCGAGTGAGACTCGCC
AAGCACTAACCTGAGGGTTAGTTACCCAGAGATACCTATGAAAAACAGTGG
TATCCAGCAAGCCTTAGTAAACTCAGGTTGCCAGCAGCTTTGCCACTTCCGC
TGCTAGCTGAATAACAAGACTGCCACTTCTGGGTCATAGTGATAGAGACTG
AAGTAGAAAAACGAATGTGGTTGGGCAAATCCCGTGTGGCCCCTCTGTGTG
CTATGATATTGATGGCACTGGTGTCTTCATTCTTGGGGGTTGCCATCATTCAC
ACACACCCCTTTGACATACAGTGCACCCCAGTTTTGAATACATTTTTTTTGCA
CCCTGTCCCGTTCTGCTACTTTGATTTGCGTTATGATATATATATATATAT
AATACCTTTTCTCCTCTTTAAACATGGTCCTGTGACACAATAGTCAGTTGCA
GAAAGGAGCCAGACTTATTCGCAAAGCACTGTGCTCAAACTCTTCAGAAAA
AAAGGAAAAAAAAAAAAGCTATAGTTGTAACATATGTATTCCAGACCTCT
GGTTTAAAGGCAAAAGAAAAAAAATCTACAGTGTTTCTTCTCATGTTTTCTG
ATCGGAGGCATGACAAAGCAAGACTGAAATCTGAACTGTGTCTCCTGCATG
GCAACACGTGTCTCCGTCAGGCCCTCGCAAGGCCCGGGGAGGGGGTTCTAC
GCCTCTTGTCTCTTTGTTGCATGCTGAACACTCATCGCCTTCCTACTGTATCC
TGCCTCCTGCAGCCTCCCTCTTCCTCCTCCTCTTCCTCTTCCTCCTCTTCCTCC
TCCTCCTCCTCTTCCTCCAAGTTTGAAAGGTCAAACAAAACTACCACATTCC
CTACCCAGTTAGAAGAAAACCACCGTCCTGACAGTTGTGATCGCATGGAGT
ACTTTTAGATTATTAGCACCTGTTTTTACCTCGTTTGTGGGCGTGTTTGTATG
TGCACATGTATGAAGTCGGCACATGCACCTTCTGTATGGGCAGAGGCGTGG
CATCTACAGAAGAGCAGATGCCAACTTTGTCTTTTAGTGAATACATTAAAA
AAAAAAAACCAACGGTCCTTATTGAGTGGAATTCTATTTGATGCAAATATTT
GAGCTCTTTAAGACTTTAAAACTAGATAATGTGCCAAGCTTTTAGGACTGCT
```

TABLE 3-continued

```
CACCAGTGCCCTCTGAAGAAACACCAGTACTTTTTCCTGTTTGTGTAATAAA
GGCATATTTGTATTTGTGTTTGCATCACTAATGGTTATTTCTTCTTAGTCCAC
TGAATGTTTCCATGTGCCTCTCGTATGCCAAACTTTTTGTCATCTTTCATGTG
GGGACCAAATGGTTTGTCTGTGGCAAACCTAAACCTATGACCTGCTGAGGCC
TCTCAGAAAACTGACCACAGTACCAAGATAGTACTTCGCAAAGAAAAGTAG
GTTCCCTCCCTGGTTTTGTAGCTGTCGCCAATATTAGCGTAATTCCAAGGAG
CTGAACGCCTTTATATAAATCTGATGGCACCTGATGCTTTTAGTTCTGAAAA
TATTTACACTCGGATCATGTTGTTGATGACTTAAACAAAGTTTTGATGAAGA
GAGCAAAAAAAAAGCAGGTGGATTTGGAACAGTTTCAGGGTTTTTTTTGTTT
TTTGTTTTTGTTTTTGTTTTTTTTTTATTTTTGTTTTTCTGTTCTCTGTTAG
AAAAGTCAGGTGTTCTCTGTCAGGCTATCTTTATAGTCAATTTTTTTTACGAA
CTAAAGTAGTACCTTTTAATATGTAGTCAACGCCCCTCTGCTCGGGGTTCAG
TTTTGGGTCTTAACCAGCTGTCATGTTCTCTATGCTGCCTGCCACTTGAGGCA
CTGAGTGCCCTAGACAGTCCCATCGGTGGTAGCCAGGGAAACGAAAGACGA
ACTCAACTCTTGCTCCTAATAATCAACTCTCTGTATGAAGGATGGCAGCATT
AAGAGTCCTCCTGCCTGGGCATTATTGGGCCAGTTCACCCTCTTTAAATCAA
ACCCGCAGTGGCTCCCAGTTCTCGTCCCATCAGATTTAAATTGCTAACAGTA
TGGGGGGCACCACGCATCTGTTTTGTCCCACAATGCGCTTTTCTCTCCCAAA
TCCCGATTTCTGCTGTCATAGCCTCTATTCAATTTTTATTTATTGTCTGCCCTC
CACTTATACAATCGTAGAGAGCAATGCCATTTGTCACTTTCTGCAACAGTTT
TTTGAGCCTTTATGGCTGAATCCCATTTTTCTTCTCTTTCAAACTGTTTGCTCC
ATTGCTCCTCCCGCACGGCTGTCCGTACAGTCATCCCATCCATCTGGGGGCC
TCTTTCATCTCTCACCCTTCCTGGTGCTTCGTGGATCTCTGCTTACCTCTGTG
GGTTTTTTTTTTTTTTTGACTTATTCTTCTCACTGGACTTTAAGATTACTTC
CACAGCGAAAGTGCTGCCTCCCTTTTCTGCCCGCAGTGTTCTGCGTACTTTA
GATACTACTCAGTGCTGACATTTGATGGCAAAAGTTGCCTGCACTTAAATTT
CTCTTTTTAATAGGGTGAACTAGAGTTGGAGTTTTTTTCTCTTTTTTCTCTTTT
CTCTCTCTCTCTCTCTCTCTCTCTCTCTCTCTCTCTCCCTCCCTCCCTC
CCTCCCTCCCTCCCTCCCTCTCTCTCTTTTCTTTCTTTCTTTCTTTCT
TTCTTTCTTTCTTTCTTTCTTTCTTTTTTTGACAAATCTCACAGGCTTTGA
GAATTATAAAAGGTGACAGTTCACCTGAAAATCACAGGTCTGGTCTGTTTAA
ATTGTTGAGAAATATCCGATTAAAGTCTTGTGGCTGTGTCCTAATAGGCTC
TCTTTCAGGACGTTGTAGTCAATAGAGTGGCTGAACCATACTTGAGTTTATA
AAGCTCAAAAACTGATGCACCCACTCTGCTATTATCGTGTTAGTAAGAGTTC
AGCTGTATATCATTGTCTAGGTTTATCTTGTCCTACAGTGGGTATTCAAATAT
GGCCACCAGAGGATATGTGTAAATATAAGCACCTGTATTTGCCTGTTGTTGA
GAACTGGAGGGAAAACAAAAAATGTCTGGCAACCCTTTGCCTTFTTAACCGT
AATTAATTGACAGTTTATTTAGAGATAAGAGTTTTCAAAAATCTCTTAACTG
CCACAACCCACAGAGGGTCTTGTTTTGCCATCTTCAGTGGCTCACAGATATG
ATCCAAGTTAACTTGAAAGAGATGAGCAGTACCCAGGAAATTGTCCTGCCTT
TAACTCTGGCTGTCCTTAATTATGACTGTTTAATGCTGAATTTTCCATCCGTC
TAGTGTTTGAGGGTAAAGAAAAGCCTTTTTTTAAATAAGTATTTCTGTAAAAC
GGCATCGGTGGGATCTTCTGTGTTGCTATCACGGGTGAAAGAGGGAAACAT
TTCTTATTTTTATTAAGCAGAGCATTATTTACAGAAAGCCATTGTTGAGAATT
AGTTCCCACATCATATAAATATCCATTAACCATTCTAAATTGTAAGAGAACT
CCAGTGTTGCTATGCACAAGGAACTCTCCTGGGGGCCTTTTTTGCATAGCA
ATTAAAGGTATGCTATTTGTCAGTAGCCATTTTTTGCAGTGATTTAAAGACC
AAACTTCTTTTACAGCTGTGTTACCCTTAAAGGTTTTTTTTTTATGTATTAAA
TCAATTTATCACTGTTTGAAGCTTTGAATACCTGCAATCTTTGCCAAGATACT
TTTTTATTTAAAAAAAATAACTGTGTAAATATTACCCTGTAATATTATATATAC
TTAATAAAACATTTTAAGCTA (SEQ ID NO: 1)
```

Mouse CD47 amino acid isoform 1 (XP_006521873.1)
MWPLAAALLLGSCCCGSAQLLFSNVNSIEFTSCNETVVIPCIVRNVEAQSTEE
MFVKWKLNKSYIFIYDGNKNSTTTDQNFTSAKISVSDLINGIASLKMDKRDA
MVGNYTCEVTELSREGKTVIELKNRTAFNTDQGSACSYEEEKGGCKLVSW
FSPNEKILIVIFPILAILLFWGKFGILTLKYKSSHTNKRIILLLVAGLVLTVIVVG
AILLIPGEKPVKNASGLGLIVISTGILILLQYNVFMTAFGMTSFTIAILITQVLGYV
LALVGLCLCIMACEPVHGPLLISGLGIIALAELLGLVYMKFVE (SEQ ID NO: 2)

Mouse CD47 mRNA isoform 2 (XM_006521811.1)
```
GCCTACACCGGGAGAGCAGGGAGGAGGAGTTGGACTGAGGTTGGGCGGCTC
CGAGGTCCAGGGCGAGCTTGGCCAGAGGGAGTAGAGAGCAGCGGGGCTGC
GCAGGGACGCGTGCCGTGACTTCCGGTGAGCGTGTGTGTCCCATGCTCCCGT
CTTTCAGGCCGGCCCAGGACACGAAGCCGGAAGAGAGCTGGCTGGAGGGAC
GGGGGGCCGTGAGCAGAGAGTGCAACCCGCGCAGCCCCGGGGACAGGCTGA
TTCTTGGCGCTCTCCGCCGGAGCCTGCCCAGGGCTGGGTGTGAGCTGGCGT
CACGTCAACGAGCAGAGGCGGCCAGGCGGGGCGGAGTGCGCGTGCGCGGG
GCGGCGAGCACGCGCGCGCGCACCCCCGGGCAGCCTGGGCGGCCGCTCC
TGCCTGTCACTGCTGCGGCGCTGCTGGTCGGTCGTTTCCCTTGAAGGCAGCA
GCGGAGGCGGCGGCTGCTCCAGACACCTGCGGCGGCGACCCCCCGGCGGCG
CGGAG**ATGTGGCCCTTGGCGGCGGCGCTGTTGCTGGGCTCCTGCTGCT
GCGGTTCAGCTCAACTACTGTTTAGTAACGTCAACTCCATAGAGTTCAC
TTCATGCAATGAAACTGTGGTCATCCCTTGCATCGTCCGTAATGTGGAG
GCGCAAAGCACCGAAGAAATGTTTGTGAAGTGGAAGTTGAACAAATCG
TATATTTTTCATCTATGATGGAAATAAAAATAGCACTACTACAGATCAAA
ACTTTACCAGTGCAAAAATCTCAGTCTCAGACTTAATCAATGGCATTGC
CTCTTTGAAAATGGATAAGCGCGATGCCATGGTGGGAAACTACACTTGC
GAAGTGACAGAGTTATCCAGAGAAGGCAAAACAGTTATAGAGCTGAAA
AACCGCACGGTTTCGTGGTTTTCTCCAAATGAAAAGATCCTCATTGTTA**
```

TABLE 3-continued

```
TTTTCCCAATTTTGGCTATACTCCTGTTCTGGGGAAAGTTTGGTATTTTA
ACACTCAAATATAAATCCAGCCATACGAATAAGAGAATCATTCTGCTGC
TCGTTGCCGGGCTGGTGCTCACAGTCATCGTGGTTGTTGGAGCCATCCT
TCTCATCCCAGGAGAAAAGCCCGTGAAGAATGCTTCTGGACTTGGCCTC
ATTGTAATCTCTACGGGGATATTAATACTACTTCAGTACAATGTGTTTAT
GACAGCTTTTGGAATGACCTCTTTCACCATTGCCATATTGATCACTCAA
GTGCTGGGCTACGTCCTTGCTTTGGTCGGGCTGTGTCTCTGCATCATGG
CATGTGAGCCAGTGCACGGCCCCCTTTTGATTTCAGGTTTGGGGATCAT
AGCTCTAGCAGAACTACTTGGATTAGTTTATATGAAGTTTGTCGCTTCC
AACCAGAGGACTATCCAACCTCCTAGGAATAGGTGAAGGGAAGTGACGG
ACTGTAACTTGGAAGTCAGAAATGGAAGAATACAGTTGTCTAAGCACCAGG
TCTTCACGACTCACAGCTGGAAGGAACAGACAACAGTAACTGACTTCCATC
CAGGAAAACATGTCACATAAATGATTACTAAGTTTATATTCAAAGCAGCTGT
ACTTTACATAATAAAAAAAATATGATGTGCTGTGTAACCAATTGGAATCCCA
TTTTTCTATTGTTTCTACTCAACTAGGGGCAAACGTTTCAGGGGCAACTTCCA
AGAATGATGCTTGTTAGATCCTAGAGTCTCTGAACACTGAGTTTAAATTGAT
TCCGAGTGAGACTCGCCAAGCACTAACCTGAGGGTTAGTTACCCAGAGATA
CCTATGAAAACAGTGGTATCCAGCAAGCCTTAGTAAACTCAGGTTGCCAG
CAGCTTTGCCACTTCCGCTGCTAGCTGAATAACAAGACTGCCACTTCTGGGT
CATAGTGATAGAGACTGAAGTAGAAAAACGAATGTGGTTGGGCAAATCCCG
TGTGGCCCCTCTGTGTGCTATGATATTGATGGCACTGGTGTCTTCATTCTTGG
GGGTTGCCATCATTCACACACACCCCTTTGACATACAGTGCACCCCAGTTTT
GAATACATTTTTTTTGCACCCTGTCCCGTTCTGCTACTTTGATTTGCGTTATG
ATATATATATATATATAATACCTTTTCTCCTCTTTAAACATGGTCCTGTGA
CACAATAGTCAGTTGCAGAAAGGAGCCAGACTTATTCGCAAAGCACTGTGC
TCAAACTCTTCAGAAAAAAAGGAAAAAAAAAAAAAGCTATAGTTGTAACAT
ATGTATTCCAGACCTCTGGTTTAAAGGCAAAAGAAAAAAAATCTACAGTGT
TTCTTCTCATGTTTTCTGATCGGAGGCATGACAAAGCAAGACTGAAATCTGA
ACTGTGTCTCCTGCATGGCAACACGTGTCTCCGTCAGGCCCTCGCAAGGCCC
GGGGAGGGGGTTCTACGCCTCTTGTCTCTTTGTTGCATGCTGAACACTCATC
GCCTTCCTACTGTATCCTGCCTCCTGCAGCCTCCCTCTTCCTCCTCCTCTTCCT
CTTCCTCCTCTTCCTCCTCCTCCTCCTCTTCCTCCAAGTTTGAAAGGTCAAAC
AAAACTACCACATTCCCTACCCAGTTAGAAGAAAACCACCGTCCTGACAGTT
GTGATCGCATGGAGTACTTTTAGATTATTAGCACCTGTTTTTACCTCGTTTGT
GGGCGTGTTTGTATGTGCACATGTATGAAGTCGGCACATGCACCTTCTGTAT
GGGCAGAGGCGTGGCATCTACAGAAGAGCAGATGCCAACTTTGTGCTTTTA
GTGAATACATTAAAAAAAAAAAAACCAACGGTCCTTATTGAGTGGAATTCTA
TTTGATGCAAATATTTGAGCTCTTTAAGACTTTAAAACTAGATAATGTGCCA
AGCTTTTAGGACTGCTCACCAGTGCCCTCTGAAGAAACACCAGTACTTTTTC
CTGTTTGTGTAATAAAGGCATATTTGTATTTGTGTTTGCATCACTAATGGTTA
TTTCTTCTTAGTCCACTGAATGTTTCCATGTGCCTCTCGTATGCCAAACTTTT
TGTCATCTTTCATGTGGGGACCAAATGGTTTGTCTGTGGCAAACCTAAACCT
ATGACCTGCTGAGGCCTCTCAGAAAACTGACCACAGTACCAAGATAGTACT
TCGCAAAGAAAAGTAGGTTCCCTCCCTGGTTTTGTAGCTGTCGCCAATATTA
GCGTAATTCCAAGGAGCTGAACGCCTTTATATAAATCTGATGGCACCTGATG
CTTTTAGTTCTGAAAATATTTACACTCGGATCATGTTGTTGATGACTTAAACA
AAGTTTTGATGAAGAGAGCAAAAAAAAAGCAGGTGGATTTGGAACAGTTTC
AGGGTTTTTTTGTTTTTTGTTTTTTGTTTTTGTTTTTTTTTTTATTTTTGTTT
TTCTGTTCTCTGTTAGAAAAGTCAGGTGTTCTCTGTCAGGCTATCTTTATAGT
CAATTTTTTTTTACGAACTAAAGTAGTACCTTTTAATATGTAGTCAACGCCCCT
CTGCTCGGGGTTCAGTTTTGGGTCTTAACCAGCTGTCATGTTCTCTATGCTGC
CTGCCACTTGAGGCACTGAGTGCCCTAGACAGTCCCATCGGTGGTAGCCAG
GGAAACGAAAGACGAACTCAACTCTTGCTCCTAATAATCAACTCTCTGTATG
AAGGATGGCAGCATTAAGAGTCCTCCTGCCTGGGCATTATTGGGCCAGTTCA
CCCTCTTTAAATCAAACCCGCAGTGGCTCCCAGTTCTCGTCCCATCAGATTT
AAATTGCTAACAGTATGGGGGGCACCACGCATCTGTTTTGTCCCACAATGCG
CTTTTCTCTCCCAAATCCCGATTTCTGCTGTCATAGCCTCTATTCAATTTTTAT
TTATTGTCTGCCCTCCACTTATACAATCGTAGAGAGCAATGCCATTTGTCACT
TTCTGCAACAGTTTTTTGAGCCTTTATGGCTGAATCCCATTTTTCTTCTCTTTC
AAACTGTTTGCTCCATTGCTCCTCCCGCACGGCTGTCCGTACAGTCATCCCAT
CCATCTGGGGGCCTCmCATCTCTCACCCTTCCTGGTGCTTCGTGGATCTCT
GCTTACCTCTGTGGGTTTTTTTTTTTTTTTGACTTATTCTTCTCACTGGACT
TTAAGATTACTTCCACAGCGAAAGTGCTGCCTCCCTTTTCTGCCCGCAGTGTT
CTGCGTACTTTAGATACTACTCAGTGCTGACATTTGATGGCAAAAGTTGCCT
GCACTTAAATTTCTCTTTTTAATAGGGTGAACTAGAGTTGGAGTTTTTTTCTC
TTTTTTCTCTTTTCTCTCTCTCTCTCTCTCTCTCTCTCTCTCTCTCTCTCT
CCCTCCCTCCCTCCCTCCCTCCCTCCCTCCCTCTCTCTCTTTTCTTTCTTTC
TTTCTTTCTTTCTTTCTTTCTTTCTTTCTTTCTTTCTTTTTTTGACAAATCT
CACAGGCTTTGAGAATTATAAAGGTGACAGTTCACCTGAAAATCACAGGT
CTGGTCTGTTTAAATTGTTGAGAAATATCCGATTAAAAGTCTTGTGGCTGTG
TCCTAATAGGCTCTCTTTCAGGACGTTGTAGTCAATAGAGTGGCTGAACCAT
ACTTGAGTTTATAAAGCTCAAAAACTGATGCACCCACTCTGCTATTATCGTG
TTAGTAAGAGTTCAGCTGTATATCATTGTCTAGGTTTATCTTGTCCTACAGTG
GGTATTCAAATATGGCCACCAGAGGATATGTGTAAATATAAGCACCTGTATT
TGCCTGTTGTTGAGAACTGGAGGGAAAACAAAAAATGTCTGGCAACCCTTT
GCCTTTTTAACCGTAATTAATTGACAGTTTATTTAGAGATAAGAGTTTTCAA
AAATCTCTTAACTGCCACAACCCACAGAGGGTCTTGTTTTGCCATCTTCAGT
GGCTCACAGATATGATCCAAGTTAACTTGAAAGAGATGAGCAGTACCCAGG
AAATTGTCCTGCCTTTAACTCTGGCTGTCCTTAATTATGACTGTTTAATGCTG
AATTTTCCATCCGTCTAGTGTTTGAGGGTAAAGAAAAGCCTTTTTTAAATAA
```

TABLE 3-continued

```
GTATTTCTGTAAAACGGCATCGGTGGGATCTTCTGTGTTGCTATCACGGGTG
AAAGAGGGAAACATTTCTTATTTTTATTAAGCAGAGCATTATTTACAGAAAG
CCATTGTTGAGAATTAGTTCCCACATCATATAAATATCCATTAACCATTCTA
AATTGTAAGAGAACTCCAGTGTTGCTATGCACAAGGAACTCTCCTGGGGGC
CTTTTTTTGCATAGCAATTAAAGGTATGCTATTTGTCAGTAGCCATTTTTTGC
AGTGATTTAAAGACCAAAGTTGTTTTACAGCTGTGTTACCCTTAAAGGTTTT
TTTTTTATGTATTAAATCAATTTATCACTGTTTGAAGCTTTGAATACCTGCAA
TCTTTGCCAAGATACTTTTTTATTTAAAAAAATAACTGTGTAAATATTACCCT
GTAATATTATATATACTTAATAAAACATTTTAAGCTA (SEQ ID NO: 3)

Mouse CD47 amino acid isoform 2 (XP_006521874.1)
MWPLAAALLLGSCCCGSAQLLFSNVNSIEFTSCNETVVIPCIVRNVEAQSTEE
MFVKWKLNKSYIFIYDGNKNSTTTDQNFTSAKISVSDLINGIASLKMDKRDA
MVGNYTCEVTELSREGKTVIELKNRTVSWFSPNEKILIVIFPILAILLFWGKFG
ILTLKYKSSHTNKRIILLLVAGLVLTVIVVVGAILLIPGEKPVKNASGLGLIVISTG
ILILLQYNVFMTAFGMTSFTIAILITQVLGYVLALVGLCLCIMACEPVHGPLLISG
LGIIALAELLGLVYMKFVASNQRTIQPPRNR (SEQ ID NO: 4)

Mouse CD47 mRNA isoform 3 (XM_006521807.1)
GCCTACACCGGGAGAGCAGGGAGGAGGAGTTGGACTGAGGTTGGGCGGCTC
CGAGGTCCAGGGCGAGCTTGGCCAGAGGGAGTAGAGAGCAGCGGGGCTGC
GCAGGGACGCGTGCCGTGAGTTCCGGTGAGCGTGTGTGTCCCATGCTCCCGT
CTTTCAGGCCGGCCCAGGACACGAAGCCGGAAGAGAGCTGGCTGGAGGGAC
GGGGGCCGTGAGCAGAGAGTGCAACCCGCGCAGCCCCGGGGACAGGCTGA
TTCTTGGCGCTCTCCGCCGGAGCCTGCCCAGGGCTGGGTGTGAGGCTGGCGT
CACGTCAACGAGCAGAGGCGGCCAGGCGGGGCGGAGTGCGCGTGCGCGGG
GCGGCGAGCACGCGCGCGCGCACCCCCGGGCAGCCTGGGCGGCCGCTCC
TGCCTGTCACTGCTGCGGCGCTGCTGGTCGGTCGTTTCCCTTGAAGGCAGCA
GCGGAGGCGGCGGCTGCTCCAGACACCTGCGGCGGCGACCCCCCGGCGGCG
CGGAGATGTGGCCCTTGGCGGCGGCGCTGTTGCTGGGCTCCTGCTGCT
GCGGTTCAGCTCAACTACTGTTTAGTAACGTCAACTCCATAGAGTTCAC
TTCATGCAATGAAACTGTGGTCATCCCTTGCATCGTCCGTAATGTGGAG
GCGCAAAGCACCGAAGAAATGTTTGTGAAGTGGAAGTTGAACAAATCG
TATATTTTCATCTATGATGGAAATAAAAATAGCACTACTACAGATCAAA
ACTTTACCAGTGCAAAAATCTCAGTCTCAGACTTAATCAATGGCATTGC
CTCTTTGAAAATGGATAAGCGCGATGCCATGGTGGGAAACTACACTTGC
GAAGTGACAGAGTTATCCAGAGAAGGCAAAACAGTTATAGAGCTGAAA
AACCGCACGGCCTTCAACACTGACCAAGGATCAGCCTGTTCTTACGAGG
AGGAGAAAGGAGGTTGCAAATTAGTTTCCTGGTTTTCTCCAAATGAAAA
GATCCTCATTGTTATTTTCCCAATTTTGGCTATACTCCTGTTCTGGGGAA
AGTTTGGTATTTTAACACTCAAATATAAATCCAGCCATACGAATAAGAG
AATCATTCTGCTGCTCGTTGCCGGGCTGGTGCTCACAGTCATCGTGGTT
GTTGGAGCCATCCTTCTCATCCCAGGAGAAAAGCCCGTGAAGAATGCTT
CTGGACTTGGCCTCATTGTAATCTCTACGGGGATATTAATACTACTTCA
GTACAATGTGTTTATGACAGCTTTTGGAATGACCTCTTTCACCATTGCC
ATATTGATCACTCAAGTGCTGGGCTACGTCCTTGCTTTGGTCGGGCTGT
GTCTCTGCATCATGGCATGTGAGCCAGTGCACGGCCCCCTTTTGATTTC
AGGTTTGGGGATCATAGCTCTAGCAGAACTACTTGGATTAGTTTATATG
AAGTTTGTCGCTTCCAACCAGAGGACTATCCAACCTCCTAGGAAAGCTG
TAGAGGAACCCCTTAACGAATAGGTGAAGGGAAGTGACGGACTGTAACTT
GGAAGTCAGAAATGGAAGAATACAGTTGTCTAAGCACCAGGTCTTCACGAC
TCACAGCTGGAAGGAACAGACAACAGTAACTGACTTCCATCCAGGAAAACA
TGTCACATAAATGATTACTAAGTTTATATTCAAAGCAGCTGTACTTTACATA
ATAAAAAAAATATGATGTGCTGTGTAACCAATTGGAATCCCATTTTTCTATT
GTTTCTACTCAACTAGGGGCAAACGTTTCAGGGGCAACTTCCAAGAATGATG
CTTGTTAGATCCTAGAGTCTCTGAACACTGAGTTTAAATTGATTCCGAGTGA
GACTCGCCAAGCACTAACCTGAGGGTTAGTTACCCAGAGATACGTATGAAA
AACAGTGGTATCCAGCAAGCCTTAGTAAACTCAGGTTGCCAGCAGCTTTGCC
ACTTCCGCTGCTAGCTGAATAACAAGACTGCCACTTCTGGGTCATAGTGATA
GAGACTGAAGTAGAAAACGAATGTGGTTGGGCAAATCCCGTGTGGCCCCT
CTGTGTGCTATGATATTGATGGCACTGGTGTCTTCATTCTTGGGGGTTGCCAT
CATTCACACACACCCCTTTGACATACAGTGCACCCCAGTTTTGAATACATTT
TTTTTGCACCCTGTCCCGTTCTGCTACTTTGATTTGCGTTATGATATATATAT
ATATATATAATACCTTTTCTCCTCTTTAAACATGGTCCTGTGACACAATAGTC
AGTTGCAGAAAGGAGCCAGACTTATTCGCAAAGCACTGTGCTCAAACTCTTC
AGAAAAAAGGAAAAAAAAAAAAAGCTATAGTTGTAACATATGTATTCCAG
ACCTCTGGTTTAAAGGCAAAAGAAAAAAAAATCTACAGTGTTTCTTCTCATGT
TTTCTGATCGGAGGCATGACAAAGCAAGACTGAAATCTGAACTGTGTCTCCT
GCATGGCAACACGTGTCTCCGTCAGGCCCTCGCAAGGCCCGGGGAGGGGT
TCTACGCCTCTTGTCTCTTTGTTGCATGCTGAACACTCATCGCCTTCCTACTG
TATCCTGCCTCCTGCAGCCTCCCTCTTCCTCCTCCTCTTCCTCTTCCTCCTCTT
CCTCCTCCTCCTCCTCTTCCTCCAAGTTTGAAAGGTCAAACAAAACTACCAC
ATTCCCTACCCAGTTAGAAGAAAACCACCGTCCTGACAGTTGTGATCGCATG
GAGTACTTTTAGATTATTAGCACCTGTTTTTACCTCGTTTGTGGGCGTGTTTG
TATGTGCACATGTATGAAGTCGGCACATGCACCTTCTGTATGGGCAGAGGCG
TGGCATCTACGAAGAGCAGATGCCAACTTTGTGCTTTTAGTGAATACATTA
AAAAAAAAAAACCAACGGTCCTTATTGAGTGGAATTCTATTTGATGCAAAT
ATTTGAGCTCTTTAAGACTTTAAAACTAGATAATGTGCCAAGCTTTTAGGAC
TGCTCACCAGTGCCCTCTGAAGAAACACCAGTACTTTTTCCTGTTTGTGTAAT
AAAGGCATATTTGTATTTGTGTTTGCATCACTAATGGTTATTTCTTCTTAGTC
```

TABLE 3-continued

```
CACTGAATGTTTCCATGTGCCTCTCGTATGCCAAACTTTTTGTCATCTTTCAT
GTGGGGACCAAATGGTTTGTCTGTGGCAAACCTAAACCTATGACCTGCTGAG
GCCTCTCAGAAAACTGACCACAGTACCAAGATAGTACTTCGCAAAGAAAAG
TAGGTTCCCTCCCTGGTTTTGTAGCTGTCGCCAATATTAGCGTAATTCCAAG
GAGCTGAACGCCTTTATATAAATCTGATGGCACCTGATGCTTTTAGTTCTGA
AAATATTTACACTCGGATCATGTTGTTGATGACTTAAACAAAGTTTTGATGA
AGAGAGCAAAAAAAAAGCAGGTGGATTTGGAACAGTTTCAGGGTTTTTTTT
GTTTTTTGTTTTTTGTTTTTGTTTTTTTTTTTATTTTTGTTTTTCTGTTCTCTG
TTAGAAAAGTCAGGTGTTCTCTGTCAGGCTATCTTTATAGTCAATTTTTTTA
CGAACTAAAGTAGTACCTTTTAATATGTAGTCAACGCCCCTCTGCTCGGGGT
TCAGTTTTGGGTCTTAACCAGCTGTCATGTTCTCTATGCTGCCTGCCACTTGA
GGCACTGAGTGCCCTAGACAGTCCCATCGGTGGTAGCCAGGGAAACCAAAG
ACGAACTCAACTCTTGCTCCTAATAATCAACTCTCTGTATGAAGGATGGCAG
CATTAAGAGTCCTCCTGCCTGGGCATTATTGGGCAGTTCACCCTCTTTAAA
TCAAACCCGCAGTGGCTCCCAGTTCTCGTCCCATCAGATTTAAATTGCTAAC
AGTATGGGGGGCACCACGCATCTGTTTTGTCCCACAATGCGCTTTTCTCTCC
CAAATCCCGATTTCTGCTGTCATAGCCTCTATTCAATTTTTATTTATTGCTG
CCCTCCACTTATACAATCGTAGAGAGCAATGCCATTTGTCACTTTCTGCAAC
AGTTTTTTGAGCCTTTATGGCTGAATCCCATTTTTCTTCTCTTTCAAACTGTTT
GCTCCATTGCTCCTCCCGCACGGCTGTCCGTACAGTCATCCCATCCATCTGG
GGGCCTCTTTCATCTCTCACCCTTCCTGGTGCTTCGTGGATCTCTGCTTACCT
CTGTGGGTTTTTTTTTTTTTTTTTTGACTTATTCTTCTCACTGGACTTTAAGATT
ACTTCCACAGCGAAAGTGCTGCCTCCCTTTTCTGCCCGCAGTGTTCTGCGTA
CTTTAGATACTACTCAGTGCTGACATTTGATGGCAAAAGTTGCCTGCACTTA
AATTTCTCTTTTTAATAGGGTGAACTAGAGTTGGAGTTTTTTCTCTTTTTTGT
CTTTTCTCTCTCTCTCTCTCTCTCTCTCTCTCTCTCTCTCTCTCTCCCTCCCT
CCCTCCCTCCCTCCCTCCCTCCCTCTCTCTCTCTTTTTCTTTCTTTCTTTCTTTC
TTTCTTTCTTTCTTTCTTTCTTTCTTTCTTTTTTGACAAATCTCACAGGC
TTTGAGAATTATAAAAGGTGACAGTTCACCTGAAAATCACAGGTCTGGTCTG
TTTAAATTGTTGAGAAATATCCGATTAAAAGTCTTGTGGCTGTGTCCTAATA
GGCTCTCTTTCAGGACGTTGTAGTCAATAGAGTGGCTGAACCATACTTGAGT
TTATAAAGCTCAAAAACTGATGCACCCACTCTGCTATTATCGTGTTAGTAAG
AGTTCAGCTGTATATCATTGTCTAGGTTTATCTTGTCCTACAGTGGGTATTCA
AATATGGCCACCAGAGGATATGTGTAAATATAAGCACCTGTATTTGCCTGTT
GTTGAGAACTGGAGGGAAAACAAAAAATGTCTGGCAACCCTTTGCCTTTTA
ACCGTAATTAATTGACAGTTTATTTAGAGATAAGAGTTTTCAAAAATCTCTT
AACTGCCACAACCCACAGAGGGTCTTGTTTTGCCATCTTCAGTGGCTCACAG
ATATGATCAAGTTAACTTGAAAGAGATGAGCAGTACCCAGGAAATTGTCC
TGCCTTTAACTCTGGCTGTCCTTAATTATGACTGTTTAATGCTGAATTTTCCA
TCCGTCTAGTGTTTGAGGGTAAAGAAAAGCCTTTTTTAAATAAGTATTTCTG
TAAAACGGCATCGGTGGGATCTTCTGTGTTGCTATCACGGGTGAAAGAGGG
AAACATTTCTTATTTTTATTAAGCAGAGCATTATTTACAGAAAGCCATTGTT
GAGAATTAGTTCCCACATCATATAAATATCCATTAACCATTCTAAATTGTAA
GAGAACTCCAGTGTTGCTATGCACAAGGAACTCTCCTGGGGGCCTTTTTTTG
CATAGCAATTAAAGGTATGCTATTTGTCAGTAGCCATTTTTTGCAGTGATTT
AAAGACCAAAGTTGTTTTACAGCTGTGTTACCCTTAAAGGTTTTTTTTTATG
TATTAAATCAATTTATCACTGTTTGAAGCTTTGAATACCTGCAATCTTTGCCA
AGATACTTTTTTATTTAAAAAAATAACTGTGTAAATATTACCCTGTAATATTA
TATATACTTAATAAAACATTTTAAGCTA (SEQ ID NO: 5)
```

Mouse CD47 amino acid isoform 3 (XP_006521870.1)
<u>MWPLAAALLLGSCCCGSA</u>**QLLFSNVNSIEFTSCNETVVIPCIVRNVEAQSTEE
MFVKWKLNKSYIFIYDGNKNSTTTDQNFTSAKISVSDLINGIASLKMDKRDA
MVGNYTCEVTELSREGKTVIELKNRTAFNTDQGSACSYEEEKGGCKLVSYV
FSPNEK**ILIVIFPILAILLFWGKFGILTLKYKSSHTNKRIILLLVAGLVLTVIVVVG
AILLIPGEKPVKNASGLGLIVISTGILILLQYNVFMTAFGMTSFTIAILITQVLGYV
LALVGLCLCIMACEPVHGPLLISGLGIIALAELLGLVYMKF*VASNQRTIQPPRKAV
EEPLNE* (SEQ ID NO: 6)

Mouse CD47 mRNA isoform 4 (XM_006521808.1)
```
GCCTACACCGGGAGAGCAGGGAGGAGGAGTTGGACTGAGGTTGGGCGGCTC
CGAGGTCCAGGGCGAGCTTGGCCAGAGGGAGTAGAGAGCAGCGGGGCTGC
GCAGGGACGCGTGCCGTGAGTTCCGGTGAGCGTGTGTGTCCCATGCTCCCGT
CTTTCAGGCCGGCCCAGGACACGAAGCCGGAAGAGAGCTGGCTGGAGGGAC
GGGGGCCGTGAGCAGAGAGTGCAACCCGCGCAGCCCCGGGGACAGGCTGA
TTCTTGGCGCTCTCCGCCGGAGCCTGCCCAGGGCTGGGTGTGAGGCTGGCGT
CACGTCAACGAGCAGAGGCGGCCAGGCGGGGCGGAGTGCGCGTGCGCGGG
GCGGCGAGCACGCGCGCGCGCGCACCCCCGGGCAGCCTGGGCGGCCGCTCC
TGCCTGTCACTGCTGCGGCGCTGCTGGTCGGTCGTTTCCCTTGAAGGCAGCA
GCGGAGGCGGCGGCTGCTCCAGACACCTGCGCGGCGACCCCCCGGCGGCG
CGGAG
```
**ATGTGGCCCTTGGCGGCGGCGCTGTTGCTGGGCTCCTGCTGCT
GCGGTTCAGCTCAACTACTGTTTAGTAACGTCAACTCCATAGAGTTCAC
TTCATGCAATGAAACTGTGGTCATCCCTTGCATCGTCCGTAATGTGGAG
GCGCAAAGCACCGAAGAAATGTTTGTGAAGTGGAAGTTAACAAATCG
TATATTTTCATCTATGATGGAAATAAAAATAGCACTACTACAGATCAAA
ACTTTACCAGTGCAAAAATCTCAGTCTCAGACTTAATCAATGGCATTGC
CTCTTTGAAAATGGATAAGCGCGATGCCATGGTGGGAAACTACACTTGC
GAAGTGACAGAGTTATCCAGAGAAGGCAAAACAGTTATAGAGCTGAAA
AACCGCACGGTTTCGTGGTTTTCTCCAAATGAAAAGATCCTCATTGTTA
TTTTCCCAATTTTGGCTATACTCCTGTTCTGGGGAAAGTTTGGTATTTA**

TABLE 3-continued

```
ACACTCAAATATAAATCCAGCCATACGAATAAGAGAATCATTCTGCTGC
TCGTTGCCGGGCTGGTGCTCACAGTCATCGTGGTTGTTGGAGCCATCCT
TCTCATCCCAGGAGAAAAGCCCGTGAAGAATGCTTCTGGACTTGGCCTC
ATTGTAATCTCTACGGGGATATTAATACTACTTCAGTACAATGTGTTTAT
GACAGCTTTTGGAATGACCTCTTTCACCATTGCCATATTGATCACTGAA
GTGCTGGGCTACGTCCTTGCTTTGGTCGGGCTGTGTCTCTGCATCATGG
CATGTGAGCCAGTGCACGGCCCCCTTTTGATTTCAGGTTTGGGGATCAT
AGCTCTAGGAGAACTACTTGGATTAGTTTATATGAAGTTTGTCGCTTCC
AACCAGAGGACTATCCAACCTCCTAGGAAAGCTGTAGAGGAACCCCTTA
ACGCATTTAAAGAGTCAAAAGGAATGATGAATGACGAATAGGTGAAGGG
AAGTGACGGACTGTAACTTGGAAGTCAGAAATGGAAGAATACAGTTGTCTA
AGCACCAGGTCTTCACGACTCACAGCTGGAAGGAACAGACAACAGTAACTG
ACTTCCATCCAGGAAAACATGTCACATAAATGATTACTAAGTTTATATTCAA
AGCAGCTGTACTTTACATAATAAAAAAAATATGATGTGCTGTGTAACCAATT
GGAATCCCATTTTCTATTGTTTCTACTCAACTAGGGGCAAACGTTTCAGGG
GCAACTTCCAAGAATGATGCTTGTTAGATCCTAGAGTCTCTGAACACTGAGT
TTAAATTGATTCCGAGTGAGACTCGCCAAGCACTAACCTGAGGGTTAGTTAC
CCAGAGATACCTATGAAAAACAGTGGTATCCAGCAAGCCTTAGTAAACTCA
GGTTGCCAGCAGCTTTGCCACTTCCGCTGCTAGCTGAATAACAAGACTGCCA
CTTCTGGGTCATAGTGATAGAGACTGAAGTAGAAAAACGAATGTGGTTGGG
CAAATCCCGTGTGGCCCCTCTGTGTGCTATGATATTGATGGCACTGGTGTCT
TCATTCTTGGGGGTTGCCATCATTCACACACACCCCTTTGACATACAGTGCA
CCCCAGTTTTGAATACATTTTTTTTGCACCCTGTCCCGTTCTGCTACTTTGATT
TGCGTTATGATATATATATATATATAATACCTTTTCTCCTCTTTAAACATG
GTCCTGTGACACAATAGTCAGTTGCAGAAAGGAGCCAGACTTATTCGCAAA
GCACTGTGCTCAAACTCTTCAGAAAAAAAGGAAAAAAAAAAAAAGCTATAG
TTGTAACATATGTATTCCAGACCTCTGGTTTAAAGGCAAAAGAAAAAAAAT
CTACAGTGTTTCTTCTCATGTTTTCTGATCGGAGGCATGACAAAGCAAGACT
GAAATCTGAACTGTGTCTCCTGCATGGCAACACGTGTCTCCGTCAGGCCCTC
GCAAGGCCCGGGGAGGGGGTTCTACGCCTCTTGTCTCTTTGTTGCATGCTGA
ACACTCATCGCCTTCCTACTGTATCCTGCCTCCTGCAGCCTCCCTCTTCCTCC
TCCTCTTCCTCTTCCTCCTCTTCCTCCTCCTCCTCCTCTTCCTCCAAGTTTGAA
AGGTCAAACAAAACTACCACATTCCCTACCCAGTTAGAAGAAAACCACCGT
CCTGACAGTTGTGATCGCATGGAGTACTTTTAGATTATTAGCACCTGTTTTTA
CCTCGTTTGTGGGCGTGTTTGTATGTGCACATGTATGAAGTCGGCACATGCA
CCTTCTGTATGGGCAGAGGCGTGGCATCTACAGAAGAGCAGATGCCAACTT
TGTGCTTTTAGTGAATACATTAAAAAAAAAAAAACCAACGGTCCTTATTGAGT
GGAATTCTATTTGATGCAAATATTTGAGCTCTTTAAGACTTTAAAACTAGAT
AATGTGCCAAGCTTTTAGGACTGCTCACCAGTGCCCTCTGAAGAAACACCAG
TACTTTTTCCTGTTTGTGTAATAAAGGCATATTTGTATTTGTGTTTGCATCAC
TAATGGTTATTTCTTCTTAGTCCACTGAATGTTTCCATGTGCCTCTCGTATGC
CAAACTTTTTGTCATCTTTCATGTGGGGACCAAATGGTTTGTCTGTGGCAAA
CCTAAACCTATGACCTGCTGAGGCCTCTCAGAAAACTGACCACAGTACCAA
GATAGTACTTCGCAAAGAAAAGTAGGTTCCCTCCCTGGTTTTGTAGCTGTCG
CCAATATTAGCGTAATTCCAAGGAGCTGAACGCCTTTATATAAATCTGATGG
CACCTGATGCTTTTAGTTCTGAAAATATTTACACTCGGATCATGTTGTTGATG
ACTTAAACAAAGTTTTGATGAAGAGAGCAAAAAAAAAGCAGGTGGATTTGG
AACAGTTTCAGGGTTTTTTTTGTTTTTTGTTTTTGTTTTTGTTTTTTTTTTTTT
ATTTTTGTTTTTCTGTTCTCTGTTAGAAAAGTCAGGTGTTCTCTGTCAGGCTA
TCTTTATAGTCAATTTTTTTTACGAACTAAAGTAGTACCTTTTAATATGTAGT
CAACGCCCCTCTGCTCGGGGTTCAGTTTTGGGTCTTAACCAGCTGTCATGTTC
TCTATGCTGCCTGCCACTTGAGGCACTGAGTGCCCTAGACAGTCCCATCGGT
GGTAGCCAGGGAAACGAAAGACGAACTCAACTCTTGCTCCTAATAATCAAC
TCTCTGTATGAAGGATGGCAGCATTAAGAGTCCTCCTGCCTGGGCATTATTG
GGCCAGTTCACCCTCTTTAAATCAAACCCGCAGTGGCTCCCAGTTCTCGTCC
CATCAGATTTAAATTGCTAACAGTATGGGGGGCACCACGCATCTGTTTTGTC
CCACAATGCGCTTTTCTCTCCCAAATCCCGATTTCTGCTGTCATAGCCTCTAT
TCAATTTTTATTTATTGTCTGCCCTCCACTTATACAATCGTAGAGAGCAATGC
CATTTGTCACTTTCTGCAACAGTTTTTTGAGCCTTTATGGCTGAATCCCATTT
TTCTTCTCTTTCAAACTGTTTGCTCCATTGCTCCTCCCGCACGGCTGTCCGTA
CAGTCATCCCATCCATCTGGGGGCCTCTTTCATCTCTCACCCTTCCTGGTGCT
TCGTGGATCTCTGCTTACCTCTGTGGGTTTTTTTTTTTTTTTGACTTATTCTT
CTCACTGGACTTTAAGATTACTTCCACAGCGAAAGTGCTGCCTCCCTTTTCTG
CCCGCAGTGTTCTGCGTACTTTAGATACTACTCAGTGCTGACATTTGATGGC
AAAAGTTGCCTGCACTTAAATTTCTCTTTTAATAGGGTGAACTAGAGTTGG
AGTTTTTTTCTCTTTTTTCTCTTTTCTCTCTCTCTCTCTCTCTCTCTCTCTCTCT
CTCTCTCTCTCTCCCTCCCTCCCTCCCTCCCTCCCTCCCTCCCTCTCTCTCTCT
TTTTCTTTCTTTCTTTCTTTCTTTCTTTCTTTCTTTCTTTCTTTCTTTCTTTT
TTTGACAAATCTCACAGGCTTTGAGAATTATAAAAGGTGACAGTTCACCTGA
AAATCACAGGTCTGGTCTGTTTAAATTGTTGAGAAATATCCGATTAAAAGTC
TTGTGGCTGTGTCCTAATAGGCTCTCTTTCAGGACGTTGTAGTCAATAGAGT
GGCTGAACCATACTTGAGTTTATAAAGCTCAAAAACTGATGCACCCACTCTG
CTATTATCGTGTTAGTAAGAGTTCAGCTGTATATCATTGTCTAGGTTTATCTT
GTCCTACAGTGGGTATTCAAATATGGCCACCAGAGGATATGTGTAAATATA
AGCACCTGTATTTGCCTGTTGTTGAGAACTGGAGGGAAAACAAAAAAGTC
TGGCAACCCTTTGCCTTTTAACCGTAATTAATTGACAGTTTATTTAGAGATA
AGAGTTTTCAAAAATCTCTTAACTGCCACAACCCACAGAGGGTCTTGTTTTG
CCATCTTCAGTGGCTCACAGATATGATCCAAGTTAACTTGAAAGAGATGAGC
AGTACCCAGGAAATTGTCCTGCCTTTAACTCTGGCTGTCCTTAATTATGACT
GTTTAATGCTGAATTTTCCATCCGTCTAGTGTTTGAGGGTAAAGAAAAGCCT
```

TABLE 3-continued

```
TTTTTAAATAAGTATTTCTGTAAAACGGCATCGGTGGGATCTTCTGTGTTGCT
ATCACGGGTGAAAGAGGGAAACATTTCTTATTTTTATTAAGCAGAGCATTAT
TTACAGAAAGCCATTGTTGAGAATTAGTTCCCACATCATATAAATATCCATT
AACCATTCTAAATTGTAAGAGAACTCCAGTGTTGCTATGCACAAGGAACTCT
CCTGGGGGCCTTTTTTTGCATAGCAATTAAAGGTATGCTATTTGTCAGTAGC
CATTTTTTGCAGTGATTTAAAGACCAAAGTTGTTTTACAGCTGTGTTACCCTT
AAAGGTTTTTTTTTATGTATTAAATCAATTTATCACTGTTTGAAGCTTTGAA
TACCTGCAATCTTTGCCAAGATACTTTTTTATTTAAAAAAATAACTGTGTAA
ATATTACCCTGTAATATTATATATACTTAATAAAACATTTTAAGCTA (SEQ ID
NO: 7)

Mouse CD47 amino acid isoform 4 (XP_006521871.1)
MWPLAAALLLGSCCCGSAQLLFSKVNSIEFTSCNETVVIPCIVRNVEAQSTEE
MFVKWKLNKSYIFIYDGNKNSTTTDQNFTSAKISVSDLINGIASLKMDKRDA
MVGNYTCEVTELSREGKTVIELKNRTVSWFSPNEKILIVIFPILAILLFWGKFG
ILTLKYKSSHTNKRIILLLVAGLVLTVIVVVGAILLIPGEKPVKNASGLGLIVISTG
ILILLQYNVFMTAFGMTSFTIAILITQVLGYVLALVGLCLCIMACEPVHGPLLISG
LGIIALAELLGLVYMKFVASNQRTIQPPRKAVEEPLNAFKESKGMMNDE (SEQ ID
NO: 8)

Human CD47 mRNA isoform 1 (XM_005247909.1)
AGTGGGAGCGCGCGTGCGCGCGGCCGTGCAGCCTGGGCAGTGGGTCCTGCC
TGTGACGCGCGGCGGCGGTCGGTCCTGCCTGTAACGGCGGCGGCGGCTGCT
GCTCCGGACACCTGCGGCGGCGGCGGCGACCCCGCGGCGGGCGCGGAGAT
GTGGCCCCTGGTAGCGGCGCTGTTGCTGGGCTCGGCGTGCTGCGGATC
ACCTCAGCTACTATTTAATAAAACAAAATCTGTAGAATTCACCTTTTGTA
ATGACACTGTCGTCATTCCATGCTTTGTTACTAATATGGAGGCACAAAA
CACTACTGAAGTATACGTAAAGTGGAAATTTAAAGGAAGAGATATTTAC
ACCTTTGATGGAGCTCTAAACAAGTCCACTGTCCCCACTGACTTTAGTA
GTGCAAAAATTGAAGTCTCACAATTACTAAAAGGAGATGCCTCTTTGAA
GATGGATAAGAGTGATGCTGTCTCACACACAGGGAAACTACACTTGTGAA
GTAACAGAATTAACCAGAGAAGGTGAAACGATCATCGAGCTAAAATATC
GTGTTGTTTCATGGTTTTCTCCAAATGAAAATATTCTTATTGTTATTTTC
CCAATTTTTGCTATACTCCTGTTCTGGGGACAGTTTGGTATTAAAACAC
TTAAATATAGATCCGGTGGTATGGATGAGAAAACAATTGCTTTACTTGT
TGCTGGACTAGTGATCACTGTCATTGTCATTGTTGGAGCCATTCTTTTC
GTCCCAGGTGAATATTCATTAAAGAATGCTACTGGCCTTGGTTTAATTG
TGACTTCTACAGGGATATTAATATTACTTCACTACTATGTGTTTAGTACA
GCGATTGGATTAACCTCCTTCGTCATTGCCATATTGGTTATTCAGGTGA
TAGCCTATATCCTCGCTGTGGTTGGACTGAGTCTCTGTATTGCGGCGTG
TATACCAATGCATGGCCCTCTTCTGATTTCAGGTTTGAGTATCTTAGCT
CTAGCACAATTACTTGGACTAGTTTATATGAAATTTGTGAATAACTGAA
GTGAAGTGATGGACTCCGATTTGGAGAGTAGTAAGACGTGAAAGGAATACA
CTTGTGTTTAAGCACCATGGCCTTGATGATTCACTGTTGGGGAGAAGAAACA
AGAAAAGTAACTGGTTGTCACCTATGAGACCCTTACGTGATTGTTAGTTAAG
TTTTTATTCAAAGCAGCTGTAATTTAGTTAATAAAATAATTATGATCTATGTT
GTTTGCCCAATTGAGATCCAGTTTTTTGTTGTTATTTTTAATCAATTAGGGGC
AATAGTAGAATGGACAATTTCCAAGAATGATGCCTTTCAGGTCCTAGGGCCT
CTGGCCTCTAGGTAACCAGTTTAAATTGGTTCAGGGTGATAACTACTTAGCA
CTGCCCTGGTGATTACCCAGAGATATCTATGAAAACCAGTGCCTTCCATCAA
ACCTTTGCCAACTCAGGTTCACAGCAGCTTTGGGCAGTTATGGCAGTATGGC
ATTAGCTGAGAGGTGTCTGCCACTTCTGGGTCAATGGAATAATAAATTAAGT
ACAGGCAGGAATTTGGTTGGGAGCATCTTGTATGATCTCCGTATGATGTGAT
ATTGATGGAGATAGTGGTCCTCATTCTTGGGGGTTGCCATTCCCACATTCCC
CCTTCAACAAACAGTGTAACAGGTCCTTCCCAGATTTAGGGTACTTTTATTG
ATGGATATGTTTTCCTTTTATTCACATAACCCCTTGAAACCCTGTCTTGTCCT
CCTGTTACTTGCTTTTTGCTGTACAAGATGTAGCACCTTTTCTCCTCTTTGAAC
ATGGTCTAGTGACACGGTAGCACCAGTTGCAGGAAGGAGCCAGACTTGTTC
TCAGAGCACTGTGTTCACACTTTTCAGCAAAAATAGCTATGGTTGTAACATA
TGTATTCCCTTCCTCTGATTTGAAGGCAAAAATCTACAGTGTTTCTTCACTTC
TTTTCTGATCTGGGGCATGAAAAAAGCAAGATTGAAATTTGAACTATGAGTC
TCCTGCATGGCAACAAAATGTGTGTCACCATCAGGCCAACAGGCCAGCCCTT
GAATGGGGATTTATTACTGTTGTATCTATGTTGCATGATAAACATTCATGAC
CTTCCTCCTGTAGTCCTGCCTCGTACTCCCCTTCCCCTATGATTGAAAAGTAA
ACAAAACCCACATTTCCTATCCTGGTTAGAAGAAAATTAATGTTCTGACAGT
TGTGATCGCCTGGAGTACTTTTAGACTTTTAGCATTCGTTTTTTACCTGTTTG
TGGATGTGTGTTTGTATGTGCATACGTATGAGATAGGCACATGCATCTTCTG
TATGGACAAAGGTGGGGTACCTACAGGAGAGCAAAGGTTAATTTTGTGCTT
TTAGTAAAAACATTTAAATACAAAGTTCTTTATTGGGTGGAATTATATTTGA
TGCAAATATTTGATCACTTAAAACTTTTAAAACTTCTAGGTAATTTGCCACG
CTTTTTGACTGCTCACCAATACCCTGTAAAAATACGTAATTCTTCCTGTTTGT
GTAATAAGATATTCATATTTGTAGTTGCATTAATAATAGTTATTTCTTAGTCC
ATCAGATGTTCCCGTGTGCCTCTTTTATGCCAAATTGATTGTCATATTTCATG
TTGGGACCAAGTAGTTTGCCCATGGCAAACCTAAATTTATGACCTGCTGAGG
CCTCTCAGAAAACTGAGCATACTAGCAAGACAGCTCTTCTTGAAAAAAAAA
ATATGTATACACAAATATATACGTATATCTATATATACGTATGTATATACAC
ACATGTATATTCTTCCTTGATTGTGTAGCTGTCCAAAATAATAACATATATA
GAGGGAGCTGTATTCCTTTATACAAATCTGATGGCTCCTGCAGCACTTTTTC
CTTCTGAAAATATTTACATTTTGCTAACCTAGTTTGTTACTTTAAAAATCAGT
TTTGATGAAAGGAGGGAAAAGCAGATGGACTTGAAAAAGATCCAAGCTCCT
```

TABLE 3-continued

ATTAGAAAAGGTATGAAAATCTTTATAGTAAAATTTTTTATAAACTAAAGTT
GTACCTTTTAATATGTAGTAAAACTCTCATTTATTTGGGGTTCGCTCTTGGATC
TCATCCATCCATTGTGTTCTCTTTAATGCTGCCTGCCTTTTGAGGCATTCACT
GCCCTAGACAATGCCACCAGAGATAGTGGGGGAAATGCCAGATGAAACCAA
CTCTTGCTCTCACTAGTTGTCAGCTTCTCTGGATAAGTGACCACAGAAGCAG
GAGTCCTCCTGCTTGGGCATCATTGGGCCAGTTCCTTCTCTTTAAATCAGATT
TGTAATGGCTCCCAAATTCCATCACATCACATTTAAATTGCAGACAGTGTTT
TGCACATCATGTATCTGTTTTGTCCCATAATATGCTTTTTACTCCCTGATCCC
AGTTTCTGCTGTTGACTCTTCCATTCAGTTTTATTTATTGTGTGTTCTCACAGT
GACACCATTTCTCCTTTTCTGCAACAACCTTTCCAGCTACTTTTGCCAAATTC
TATTTGTCTTCTCCTTCAAAACATTCTCCTTTGCAGTTCCTCTTCATCTGTGTA
GCTGCTCTTTTGTCTCTTAACTTACCATTCCTATAGTACTTTATGCATCTCTGC
TTAGTTCTATTAGTTTTTTGGCCTTGCTCTTCTCCTTGATTTTAAAATTCCTTC
TATAGCTAGAGCTTTTCTTTCTTTCATTCTCTCTTCCTGCAGTGTTTTGCATAC
ATCAGAAGCTAGGTACATAAGTTAAATGATTGAGAGTTGGCTGTATTTAGAT
TTATCACTTTTAATAGGGTGAGCTTGAGAGTTTTGTTTCTTTCTGTTTTTTTT
TTTTGTTTTTTTTTTTTTTTTTTTTTTTTTTTTGACTAATTTCACATGCTCT
AAAAACCTTCAAAGGTGATTATTTTTCTCCTGGAAACTCCAGGTCCATTCTG
TTTAAATCCCTAAGAATGTCAGAATTAAAATAACAGGGCTATCCCGTAATTG
GAAATATTTCTTTTTTCAGGATGCTATAGTCAATTTAGTAAGTGACCACCAA
ATTGTTATTTGCACTAACAAAGCTCAAAACACGATAAGTTTACTCCTCCATC
TCAGTAATAAAAATTAAGCTGTAATCAACCTTCTAGGTTTCTCTTGTCTTAA
AATGGGTATTCAAAAATGGGGATCTGTGGTGTATGTATGGAAAGACATACT
CCTTAATTTACCTGTTGTTGGAAACTGGAGAAATGATTGTCGGGCAACCGTT
TATTTTTTATTGTATTTTATTTGGTTGAGGGATTTTTTATAAACAGTTTTACT
TGTGTCATATTTTAAATTACTAACTGCCATCACCTGCTGGGGTCCTTTGTTA
GGTCATTTTCAGTGACTAATAGGGATAATCCAGGTAACTTTGAAGAGATGA
GCAGTGAGTGACCAGGCAGTTTTTCTGCCTTTAGCTTTGACAGTTCTTAATTA
AGATCATTGAAGACCAGCTTTCTCATAAATTTCTCTTTTTGAAAAAAAGAAA
GCATTTGTACTAAGCTCCTCTGTAAGACAACATCTTAAATCTTAAAAGTGTT
GTTATCATGACTGGTGAGAGAAGAAAACATTTTGTTTTTATTAAATGGAGGA
TTATTTACAAAAAGCCATTGTTGAGAATTAGATCCCACATCGTATAAATATC
TATTAACCATTCTAAATAAAGAGAACTCCAGTGTTGCTATGTGCAAGATCCT
CTCTTGGAGCTTTTTTGCATAGCAATTAAAGGTGTGCTATTTGTCAGTAGCC
ATTTTTTTGCAGTGATTTGAAGACCAAAGTTGTTTTACAGCTGTGTTACCGTT
AAAGGTTTTTTTTTTATATGTATTAAATCAATTTATCACTGTTTAAAGCTTT
GAATATCTGCAATCTTTGCCAAGGTACTTTTTTATTTAAAAAAAAACATAAC
TTTGTAAATATTACCCTGTAATATTATATATACTTAATAAAACATTTTAAGCT
A (SEQ ID NO: 9)

Human CD47 amino acid isoform 1 (XP_005247966.1)
MWPLVAALLLGSACCGSAQLLFNKTKSVEFTFCNDTVVIPCFVTNMEAQNT
TEVYVKWKFKGRDIYTFDGALNKSTVPTDFSSAKIEVSQLLKGDASLKMDK
SDAVSHTGNYTCEVTELTREGETIIELKYRVVSWFSPNENILIVIFPIFAILLFW
GQFGIKTLKYRSGGMDEKTIALLVAGLVITVIVIVGAILFVPGEYSLKNATGLGLI
VTSTGILILLHYYVFSTAIGLTSFVIAILVIQVIAYILAVVGLSLCIAACIPMHGPLLI
SGLSILALAQLLGLVYMKFVE
(SEQ ID NO: 10)

Human CD47 mRNA isoform 2 (NM_198703.2)
GGGGAGCAGGCGGGGGAGCGGGCGGGAAGCAGTGGGAGCGCGCGTGCGCG
CGGCCGTGCAGCCTGGGCAGTGGGTCCTGCCTGTGACGCGCGGCGGCGGTC
GGTCCTGCCTGTAACGGCGGCGGCGGCTGCTGCTCCAGACACCTGCGGCGG
CGGCGGCGACCCCGCGGCGGGCGCGGA**ATGTGGCCCCTGGTAGCGGCG
CTGTTGCTGGGCTCGGCGTGCTGCCGATCAGCTCAGCTACTATTTAATA
AAACAAAATCTGTACAATTCACGTTTTGTAATGACACTGTCGTCATTCC
ATGGTTTGTTACTAATATGGAGGTACAAAACACTATTGAAGTATACGTA
AAGTGGAAATTTAAAGGAAGAGATATTTACACCTTTGATGGAGCTCTAA
ACAAGTCCACTGTCCCCACTGACTTTAGTAGTGCAAAAATTGAAGTCTC
ACAATTACTAAAAGGAGATGCCTCTTTGAAGATGGATAAGAGTGATGCT
GTCTCACACACAGGAAACTACACTTGTGAAGTAACAGAATTAACCAGAG
AAGGTGAAACGATCATCGAGCTAAAATATCGTGTTGTTTCATGGTTTTC
TCCAAATGAAAATATTCTTATTGTTATTTTCCCAATTTTTGCTATACTCC
TGTTCTGGGGACAGTTTGGTATTAAAACACTTAAATATAGATCCGGTGG
TATGGATGAGAAAACAATTGCTTTACTTGTTGCTGGACTAGTGATCACT
GTCATTGTTATTGTTGGAGCCATTCTTTTCGTCCCAGGTGAATATTCATT
AAAGAATGCTACTGGCCTTGGTTTAATTGTGACTTCTACAGGGATATTA
ATATTACTTCACTACTATGTGTTTAGTACAGCGATTGGATTAACCTCCTT
CGTCATTGCCATATTGGTTATTCAGGTGATAGCCTATATCCTCGCTGTG
GTTGGACTGAGTCTCTGTATTGCGGCGTGTATACCAATGCATGGCCCTC
TTCTGATTTCAGGTTTGAGTATCTTAGCTCTAGCACAATTACTTGGACTA
GTTTATATGAAATTTGTGGCTTCCAATCAGAAGACTATACAACCTCCTA
GGAATAACTGA**AGTGAAGTGATGGACTCCGATTTGGAGAGTAGTAAGACG
TGAAAGGAATACACTTGTGTTTAAGCACCATGGCCTTGATGATTCACTGTTG
GGGAGAAGAAACAAGAAAAGTAACTGGTTGTCACCTATGAGACCCTTACGT
GATTGTTAGTTAAGTTTTTATTCAAAGCAGCTGTAATTTAGTAATAAAATA
ATTATGATCTATGTTGTTTGCCCAATTGAGATCCAGTTTTTTGTTGTTATTTTT
AATCAATTAGGGGCAATAGTAGAATGGACAATTTCCAAGAATGATGCCTTT
CAGGTCCTAGGGCCTCTGGCCTCTAGGTAACCAGTTTAAATTGGTTCAGGGT
GATAACTACTTAGCACTGCCCTGGTGATTACCCAGAGATATCTATGAAAACC TABLE 3-continued

```
AGTGGCTTCCATCAAACCTTTGCCAACTCAGGTTCACAGCAGCTTTGGGCAG
TTATGGCAGTATGGCATTAGCTGAGAGGTGTCTGCCACTTCTGGGTCAATGG
AATAATAAATTAAGTACAGGCAGGAATTTGGTTGGGAGCATCTTGTATGATC
TCCGTATGATGTGATATTGATGGAGATAGTGGTCCTCATTCTTGGGGGTTGC
CATTCCCACATTCCCCCTTCAACAAACAGTGTAACAGGTCCTTCCCAGATTT
AGGGTACTTTTATTGATGGATATGTTTTCCTTTTATTCACATAACCCCTTGAA
ACCCTGTCTTGTCCTCCTGTTACTTGCTTCTGCTGTACAAGATGTAGCACCTT
TTCTCCTCTTTGAACATGGTCTAGTGACACGGTAGCACCAGTTGCAGGAAGG
AGCCAGACTTGTTCTCAGAGCACTGTGTTCACACTTTTCAGCAAAAATAGCT
ATGGTTGTAACATATGTATTCCCTTCCTCTGATTTGAAGGCAAAAATCTACA
GTGTTTCTTCACTTCTTTTCTGATCTGGGGCATGAAAAAAGCAAGATTGAAA
TTTGAACTATGAGTCTCCTGCATGGCAACAAAATGTGTGTCACCATCAGGCC
AACAGGCCAGCCCTTGAATGGGGATTTATTACTGTTGTATCTATGTTGCATG
ATAAACATTCATCACCTTCCTCCTGTAGTCCTGCCTCGTACTCCCCTTCCCCT
ATGATTGAAAAGTAAACAAAACCCACATTTCCTATCCTGGTTAGAAGAAAA
TTAATGTTCTGACAGTTGTGATCGCCTGGAGTACTTTTAGACTTTTAGCATTC
GTTTTTTACCTGTTTGTGGATGTGTGTTTGTATGTGCATACGTATGAGATAGG
CACATGCATCTTCTGTATGGACAAAGGTGGGGTACCTACAGGAGAGCAAAG
GTTAATTTTGTGCTTTTAGTAAAAACATTTAAATACAAAGTTCTTTATTGGGT
GGAATTATATTTGATGCAAATATTTGATCACTTAAAACTTTTAAAACTTCTA
GGTAATTTGCCACGCTTTTTGACTGCTCACCAATACCCTGTAAAAATACGTA
ATTCTTCCTGTTTGTGTAATAAGATATTCATATTTGTAGTTGCATTAATAATA
GTTATTTCTTAGTCCATCAGATGTTCCCGTGTGCCTCTTTTATGCCAAATTGA
TTGTCATATTTCATGTTGGGACCAAGTAGTTTGCCCATGGCAAACCTAAATT
TATGACCTGCTGAGGCCTCTCAGAAAACTGAGCATACTAGCAAGACAGCTC
TTCTTGAAAAAAAAAATATGTATACACAAATATATACGTATATCTATATATA
CGTATGTATATACACACATGTATATTCTTCCTTGATTGTGTAGCTGTCCAAAA
TAATAACATATATAGAGGGAGCTGTATTCCTTTATACAAATCTGATGGCTCC
TGCAGCACTTTTCCTTCTGAAAATATTTACATTTTGCTAACCTAGTTTGTTA
CTTTAAAAATCAGTTTTGATGAAAGGAGGGAAAAGCAGATGGACTTGAAAA
AGATCCAAGCTCCTATTAGAAAAGGTATGAAAATCTTTATAGTAAAATTTTT
TATAAACTAAAGTTGTACCTTTTAATATGTAGTAAACTCTCATTTATTTGGGG
TTCGCTCTTGGATCTCATCCATCCATTGTGTTCTCTTTAATGCTGCCTGCCTTT
TGAGGCATTCACTGCCCTAGACAATGCCACCAGAGATAGTGGGGGAAATGC
CAGATGAAACCAACTCTTGCTCTCACTAGTTGTCAGCTTCTCTGGATAAGTG
ACCACAGAAGCAGGAGTCCTCCTGCTTGGGCATCATTGGGCCAGTTCCTTCT
CTTTAAATCAGATTTGTAATGGCTCCCAAATTCCATCACATCACATTTAAATT
GCAGACAGTGTTTTGCACATCATGTATCTGTTTTGTCCCATAATATGCTTTTT
ACTCCCTGATCCCAGTTTCTGCTGTTGACTCTTCCATTCAGTTTTATTTATTGT
GTGTTCTCACAGTGACACCATTTGTCCTTTTCTGCAACAACCTTTCCAGCTAC
TTTTGCCAAATTCTATTTGTCTTCTCCTTCAAAACATTCTCCTTTGCAGTTCCT
CTTCATCTGTGTAGCTGCTCTTTTGTCTCTTAACTTACCATTCCTATAGTACTT
TATGCATCTCTGCTTAGTTCTATTAGTTTTTTGGCCTTGCTCTTCTCCTTGATT
TTAAAATTCCTTCTATAGCTAGAGCTTTTCTTTCTTTCATTCTCTCTTCCTGCA
GTGTTTTGCATACATCAGAAGCTAGGTACATAAGTTAAATGATTGAGAGTTG
GCTGTATTTAGATTTATCACTTTTTAATAGGGTGAGCTTGAGAGTTTTCTTTC
TTTCTGTTTTTTTTTTTGTTTTTTTTTTTTTTTTTTTTTTTTTTTTTGACTA
ATTTCACATGCTCTAAAAACCTTCAAAGGTGATTATTTTTCTCCTGGAAACTC
CAGGTCCATTCTGTTTAAATCCCTAAGAATGTCAGAATTAAAATAACAGGGC
TATCCCGTAATTGGAAATATTTCTTTTTTCAGGATGCTATAGTCAATTTAGTA
AGTGACCACCAAATTGTTATTTGCACTAACAAAGCTCAAAACACGATAAGTT
TACTCCTCCATCTCAGTAATAAAAATTAAGCTGTAATCAACCTTCTAGGTTT
CTCTTGTCTTAAATGGGTATTCAAAAATGGGGATCTGTGGTGTATGTATGG
AAACACATACTCCTTAATTTACCTGTTGTTGGAAACTGGAGAAATGATTGTC
GGGCAACCGTTTATTTTTTATTGTATTTTATTTGGTTGAGGGATTTTTTATA
AACAGTTTTACTTGTGTCATATTTTAAAATTACTAACTGCCATCACCTGCTGG
GGTCCTTTGTTAGGTCATTTTCAGTGACTAATAGGGATAATCCAGGTAACTT
TGAAGAGATGAGCAGTGAGTGACCAGGCAGTTTTTCTGCCTTTAGCTTTGAC
AGTTCTTAATTAAGATCATTGAAGACCAGCTTTCTCATAAATTTCTCTTTTG
AAAAAAAGAAAGCATTTGTACTAAGCTCCTCTGTAAGACAACATCTTAAAT
CTTAAAAGTGTTGTTATCATGACTGGTGAGAGAAGAAAACATTTGTTTTTA
TTAAATGGAGCATTATTTACAAAAAGCCATTGTTGAGAATTAGATCCCACAT
CGTATAAATATCTATTAACCATTCTAAATAAAGAGAACTCCAGTGTTGCTAT
GTGCAAGATCCTCTCTTGGAGCTTTTTGCATAGCAATTAAAGGTGTGCTAT
TTGTCAGTAGCCATTTTnTGCAGTGATTTGAAGACCAAAGTTGTTTTACAGC
TGTGTTACCGTTAAAGGTTTTTTTTTTATATGTATTAAATCAATTTATCACT
GTTTAAAGCTTTGAATATCTGCAATCTTTGCCAAGGTACTTTTTTATTTAAAA
AAAAACATAACTTTGTAAATATTACCCTGTAATATTATATATACTTAATAAA
ACATTTTAAGCTATTTTGTTGGGCTATTTCTATTGCTGCTACAGCAGACCACA
AGCACATTTCTGAAAAATTTAATTTATTAATGTATTTTTAAGTTGCTTATATT
CTAGGTAACAATGTAAAGAATGATTTAAAATATTAATTATGAATTTTTTGAG
TATAATACCCAATAAGCTTTTAATTAGAGCAGAGTTTTAATTAAAAGTTTTA
AATCAGTC
```
(SEQ ID NO: 11)

Human CD47 amino acid isoform 2 (NP_942088.1)
MWPLVAALLLGSACCGSAQLLFNKTKSVEFTFCNPTVVIPCFVTNMEAQNT
TEVYVKWKFKGRDIYTFDGALNKSTVPTDFSSAKIEVSQLLKGDASLKMDK
SDAVSHTGNYTCEVTELTREGETIIELKYRVVSWFSPNENILIVIFPIFAILLFW
GQFGIKTLKYRSGGMDEKTIALLVAGLVITVIVIVGAILFVPGEYSLKNATGLGLI TABLE 3-continued VTSTGILILLHYYVFSTAIGLTSFVIAILVIQVIAYILAVVGLSLCIAACIPMHGPLLI
SGLSILALAQLLGLVYMKFV*ASNQKTIQPPRNN* (SEQ ID NO: 12)

Human CD47 mRNA isoform 3 (XM_005247908.1)
AGTGGGAGCGCGCGTGCGCGCGGCCGTGCAGCCTGGGCAGTGGGTCCTGCC
TGTGACGCGCGGCGGCGGTCGGTCCTGCCTGTAACGGCGGCGGCGGCTGCT
GCTCCGGACACCTGCGGCGGCGGCGGCGACCCCGCGGCGGGCGCGGAG**AT
GTGGCCCCTGGTAGCGGCGCTGTTGCTGGGCTCGGCGTGCTGCGG**ATC
AGCTCAGCTACTATTTAATAAAACAAAATCTGTAGAATTCACGTTTTGTA
ATGACACTGTCGTCATTCCATGCTTTGTTACTAATATGGAGGCACAAAA
CACTACTGAAGTATACGTAAAGTGGAAATTTAAAGGAAGAGATATTTAC
ACCTTTGATGGAGCTCTAAACAAGTCCACTGTCCCCACTGACTTTAGTA
GTGCAAAAATTGAAGTCTCACAATTACTAAAAGGAGATGCCTCTTTGAA
GATGGATAAGAGTGATGCTGTCTCACACACAGGAAACTACACTTGTGAA
GTAACAGAATTAACCAGAGAAGGTGAAACGATCATCGAGCTAAAATATC
GTGTTGTTTCATGGTTTTCTCCAAATGAAAATATTCTTATTGTTATTTTC
CCAATTTTTGCTATACTCCTGTTCTGGGGACAGTTTGGTATTAAAACAC
TTAAATATAGATCCGGTGGTATGGATGAGAAAACAATTGCTTTACTTGT
TGCTGGACTAGTGATCACTGTCATTGTCATTGTTGGAGCCATTCTTTTC
GTCCCAGGTGAATATTCATTAAAGAATGCTACTGGCCTTGGTTTAATTG
TGACTTCTACAGGGATATTAATATTCTTCACTACTATGTGTTTAGTACA
GCGATTGGATTAACCTCCTTCGTCATTGCCATATTGGTTATTCAGGTGA
TAGCCTATATCCTCGCTGTGGTTGGACTGAGTCTCTGTATTGCGGCGTG
TATACCAATGCATGGCCCTCnCTGATTTCAGGTTTGAGTATCTTAGCT
CTAGCACAATTACTTGGACTAGTTTATATGAAATTTGTGGCTTCCAATC
AGAAGACTATACAACCTCCTAGGAAAGCTGTAGAGGAACCCCTTAATGAATAA
CTGAAGTGAAGTGATGGACTCCGATTTGGAGAGTAGTAAGACGTGAA
AGGAATACACTTGTGTTTAAGCACCATGGCCTTGATGATTCACTGTTGGGGA
GAAGAAACAAGAAAAGTAACTGGTTGTCACCTATGAGACCCTTACGTGATT
GTTAGTTAAGTTTTTATTCAAAGCAGCTGTAATTTAGTTAATAAAATAATTAT
GATCTATGTTGTTTGCCCAATTGAGATCCAGTTTTTTGTTGTTATTTTTAATC
AATTAGGGGCAATAGTAGAATGGACAATTTCCAAGAATGATGCCTTTCAGG
TCCTAGGGGCTCTGGCCTCTAGGTAACCAGTTTAAATTGGTTCAGGGTGATA
ACTACTTAGCACTGCCCTGGTGATTACCCAGAGATATCTATGAAAACCAGTG
GCTTCCATCAAACCTTTGCCAACTCAGGTTCACAGCAGCTTTGGGCAGTTAT
GGCAGTATGGCATTAGCTGAGAGGTGTCTGCCACTTCTGGGTCAATGGAATA
ATAAATTAAGTACAGGCAGGAATTTGGTTGGGAGCATCTTGTATGATCTCCG
TATGATGTGATATTGATGGAGATAGTGGTCCTCATTCTTGGGGGTTGCCATT
CCCACATTCCCCCTTCAACAAACAGTGTAACAGGTCCTTCCCAGATTTAGGG
TACTTTTATTGATGGATATGTTTTCCTTTTATTCACATAACCCCTTGAAACCC
TGTCTTGTCCTCCTGTTACTTGCTTCCTGCTGTACAAGATGTAGCACCTTTTCT
CCTCTTTGAACATGGTCTAGTGACACGGTAGCACCAGTTGCAGGAAGGAGC
CAGACTTGTTCTCAGAGCACTGTGTTCACACTTTTCAGCAAAAATAGCTATG
GTTGTAACATATGTATTCCCCTTCCTCTGATTTGAAGGCAAAATCTACAGTG
TTTCTTCACTTCTTTTCTGATCTGGGGCATGAAAAAAGCAAGATTGAAATTT
GAACTATGAGTCTCCTGCATGGCAACAAAATGTGTGTCACCATCAGGCCAA
CAGGCCAGCCCTTGAATGGGGATTATTACTGTTGTATCTATGTTGCATGAT
AAACATTCATCACCTTCCTCCTGTAGTCCTGCCTCGTACTCCCCTTCCCCTAT
GATTGAAAAGTAAACAAAACCCACATTTCCTATCCTGGTTAGAAGAAAATT
AATGTTCTGACAGTTGTGATCGCCTGGAGTACTTTTAGACTTTTAGCATTCGT
TTTTTACCTGTTTGTGGATGTGTGTTTGTATGTGCATACGTATGAGATAGGCA
CATGCATCTTCTGTATGGACAAAGGTGGGGTACCTACAGGAGAGCAAGGT
TAATTTTGTGCTTTTAGTAAAAACATTTAAATACAAAGTTCTTTATTGGGTGG
AATTATATTTGATGCAAATATTTGATCACTTAAAACTTTTAAAACTTCTAGGT
AATTTGCCACGCTTTTTGACTGCTCACCAATACCCTGTAAAAATACGTAATT
CTTCCTGTTTGTGTAATAAGATATTCATATTTGTAGTTGCATTAATAATAGTT
ATTTCTTAGTCCATCAGATCTTCCCGTCTGCCTCTTTTATGCCAAATTGATTG
TCATATTTCATGTTGGGACCAAGTAGTTTGCCCATGGCAAACCTAAATTTAT
GACCTGCTGAGGCCTCTCAGAAAACTGAGCATACTAGCAAGACAGCTCTTCT
TGAAAAAAAAAATATGTATACACAAATATATACGTATATCTATATATACGTA
TGTATATACACACATGTATATTCTTCCTTGATTGTGTAGCTGTCCAAAATAAT
AACATATATAGAGGGAGCTGTATTCCTTTATACAAATCTGATGGCTCCTGCA
GCACTTTTTCCTTCTGAAAATATTTACATTTTGCTAACCTAGTTTGTTACTTT
AAAAATCAGTTTTGATGAAAGGAGGGAAAAGCAGATGGACTTGAAAAAGA
TCCAAGCTCCTATTAGAAAAGGTATGAAAATCTTTATAGTAAAATTTTTTAT
AAACTAAAGTTGTACCTTTTAAATATGTAGTAAAACTCTCATTTATTTGGGGTTC
GCTCTTGGATCTCATCCATCCATTGTGTTCTCTTTAATGCTGCCTGCCTTTTG
AGGCATTCACTGCCCTAGACAATGCCACCAGAGATAGTGGGGGAAATGCCA
GATGAAACCAACTCTTGCTCTCACTAGTTGTCAGCTTCTCTGGATAAGTGAC
CACAGAAGCAGGACTCCTCCTGCTTGGGCATCATTGGGCCAGTTCCTTCTCT
TTAAATCAGATTTGTAATGGCTCCCAAATTCCATCACATCACATTTAAATTG
CAGACAGTGTTTTGCACATCATGTATCTGTTTTGTCCCATAATATGCTTTTTA
CTCCCTGATCCCAGTTTCTGCTGTTGACTCTTCCATTCAGTTTTATTTATTGTG
TGTTCTCACAGTGACACCATTTGTCCTTTTCTGCAACAACCTTTCCAGCTACT
TTTGCCAAATTCTATTTGTCTTCTCCTTCAAAACATTCTCCTTTGGAGTTCCTC
TTCATCTGTGTAGCTGCTCTTTTGTCTCTTAACTTACCATTCCTATAGTACTTT
ATGCATCTTCTGCTTAGTTCTATTAGTTTTTTGGCCTTGCTCTTCTCCTTGATTT
TAAAATTCCTTCTATAGCTAGAGCTTTTCTTTCTTTCATTCTCTCTTCCTGCAG
TGTTTTGCATACATCAGAAGCTAGGTACATAAGTTAAATGATTGAGAGTTGG
CTGTATTTAGATTTATCACTTTTTAATAGGGTGAGCTTGAGAGTTTTCTTTCT TABLE 3-continued TTCTGTTTTTTTTTTTGTTTTTTTTTTTTTTTTTTTTTTTTTTTTTGACTAA
TTTCACATGCTCTAAAAACCTTCAAAGGTGATTATTTTTCTCCTGGAAACTCC
AGGTCCATTCTGTTTAAATCCCTAAGAATGTCAGAATTAAAATAACAGGGCT
ATCCCGTAATTGGAAATATTTCTTTTTTCAGGATGCTATAGTCAATTTAGTAA
GTGACCACCAAATTGTTATTTGCACTAACAAAGCTCAAAACACGATAAGTTT
AGTCCTCCATCTCAGTAATAAAAATTAAGCTGTAATCAAGCTTCTAGGTTTC
TCTTGTCTTAAAATGGGTATTCAAAAATGGGGATCTGTGGTGTATGTATGGA
AACACATACTCCTTAATTTACCTGTTGTTGGAAACTGGAGAAATGATTGTCG
GGCAACCGTTTATTTTTTATTGTATTTTATTTGGTTGAGGGATTTTTTTATAA
ACAGTTTTACTTGTGTCATATTTTAAAATTACTAACTGCCATCACCTGCTGGG
GTCCTTTGTTAGGTCATTTTCAGTGACTAATAGGGATAATCCAGGTAACTTT
GAAGAGATGAGCAGTGAGTGACCAGGCAGTTTTTCTGCCTTTAGCTTTGACA
GTTCTTAATTAAGATCATTGAAGACCAGCTTTCTCATAAATTTCTCTTTTTGA
AAAAAAGAAAGCATTTGTACTAAGCTCCTCTGTAAGACAACATCTTAAATCT
TAAAAGTGTTGTTATCATGACTGGTGAGAGAAGAAAACATTTTGTTTTTATT
AAATGGAGCATTATTTACAAAAAGCCATTGTTGAGAATTAGATCCCACATCG
TATAAATATCTATTAACCATTCTAAATAAAGAGAACTCCAGTGTTGCTATGT
GCAAGATCCTCTCTTGGAGCTTTTTTGCATAGCAATTAAAGGTGTGCTATTT
GTCAGTAGCCATTTTTTTGCAGTGATTTGAAGACCAAAGTTGTTTTACAGCT
GTGTTACCGTTAAAGGTTTTTTTTTTATATGTATTAAATCAATTTATCACTG
TTTAAAGCTTTCAATATCTGCAATCTTTGCCAAGGTACTTTTTTATTTAAAAA
AAAACATAACTTTGTAAATATTACCCTGTAATATTATATATACTTAATAAAA
CATTTTAAGCTA (SEP ID NO: 13)

Human CD47 amino acid isoforrn 3 (XP_005247965.1)
MWPLVAALLLGSACCGSAQLLFNKTKSVEFTFCNDTVVIPCFVTNMEAQNT
TEVYVKWKFKGRDIYTFDGALNKSTVPTDFSSAKIEVSQLLKGDASLKMDK
SDAVSHTGNYTCEVTELTREGETIIELKYRVVSWFSPNENILIVIFPIFAILLFW
GQFGIKTLKYRSGGMDEKTIALLVAGLVITVIVIVGAILFVPGEYSLKNATGLGLI
VTSTGILILLHYYVFSTAIGLTSFVIAILVIQVIAYILAVVGLSLCIAACIPMHGPLLI
SGLSILALAQLLGLVYMKFVASNQKTIQPPKKAVEEPLNE (SEQ ID NO: 14)

Human CD47 mRNA isoform 4 (NM_001777.3)
GGGGAGCAGGCGGGGGAGCGGGCGGGAAGCAGTGGGAGCGCGCGTGCGCG
CGGCCGTGCAGCCTGGGCAGTGGGTCCTGCCTGTGACGCGCGGCGGCGGTC
GGTCCTGCCTGTAACGGCGGCGGCGGCTGCTGCTCCAGACACCTGCGGCGG
CGGCGGCGACCCCGCGGCGGGCGCGGAGATGTGGCCCCTGGTAGCGGCG
CTGTTGCTGGGCTCGGCGTGCTGCGGATCAGCTCAGCTACTATTTAATA
AAACAAAATCTGTAGAATTCACGTTTTGTAATGACACTGTCGTCATTCC
ATGCTTTGTTACTAATATGGAGGCACAAAACACTACTGAAGTATACGTA
AAGTGGAAATTTAAAGGAAGAGATATTTACACCTTTGATGGAGCTCTAA
ACAAGTCCACTGTCCCCACTGACTTTAGTAGTGCAAAAATTGAAGTCTC
ACAATTACTAAAAGGAGATGCCTCTTTGAAGATGGATAAGAGTGATGCT
GTCTCACAGACAGGAAACTACACTTGTGAAGTAACAGAATTAACCAGAG
AAGGTGAAACGATCATCGAGCTAAAATATCGTGTTGTTTCATGGTTTTC
TCCAAATGAAAATATTCTTATTGTTATTTTCCCAATTTTTGCTATACTCC
TGTTCTGGGGACAGTTTGGTATTAAAACACTTAAATATAGATCCGGTGG
TATGGATGAGAAAACAATTGCTTTACTTGTTGCTGGACTAGTGATCACT
GTCATTGTCATTGTTGGAGCCATTCTTTTCGTCCCAGGTGAATATTCATT
AAAGAATGCTACTGGCCTTGGTTTAATTGTGACTTCTACAGGGATATTA
ATATTACTTCACTACTATGTGTTTAGTACAGCGATTGGATTAACCTCCTTT
CGTCATTGCCATATTGGTTATTCAGGTGATAGCCTATATCCTCGCTGTG
GTTGGACTGAGTCTCTGTATTGCGGCGTGTATACCAATGCATGGCCCTC
TTCTGATTTCAGGTTTGAGTATCTTAGCTCTAGCACAATTACTTGGACTA
GTTTATATGAAATTTGTGGCTTCCAATCAGAAGACTATACAACCTCCTA
GGAAAGCTGTAGAGGAACCCCTTAATGCATTCAAAGAATCAAAAGGAAT
GATGAATGATGAATAACTGAAGTGAAGTGATGGACTCCGATTTGGAGAGT
AGTAAGACGTGAAAGGAATACACTTGTGTTTAAGCACCCATGGCCTTGATGA
TTCACTGTTGGGGAGAAGAAACAAGAAAAGTAACTGGTTGTCACCTATGAG
ACCCTTACGTGATTGTTAGTTAAGTTTTTATTCAAAGCAGCTGTAATTTAGTT
AATAAAATAATTATGATCTATGTTGTTTGCCCAATTGAGATCCAGTTTTTTGT
TGTTATTTTTAATCAATTAGGGGCAATAGTAGAATGGACAATTTCCAAGAAT
GATGCCTTTCAGGTCCTAGGGCCTCTGGCCTCTAGGTAACCAGTTTAAATTG
GTTCAGGGTGATAACTACTTAGCACTGCCCTGGTGATTACCCAGAGATATCT
ATGAAAACCAGTGGCTTCCATCAAACCTTTGCCAACTCAGGTTCACAGCAGC
TTTGGGCAGTTATGGCAGTATGGCATTAGCTGAGAGGTGTCTGCCACTTCTG
GGTCAATGGAATAAATTAAGTACAGGCAGGAATTTGGTTGGGAGCATC
TTGTATGATCTCCGTATGATGTGATATTGATGGAGATAGTGGTCCTCATTCTT
GGGGGTTGCCATTCCCACATTCCCCCTTCAACAAACAGTGTAACAGGTCCTT
CCCAGATTTAGGGTACTTTTATTGATGGATATGTTTTCCTTTTATTCACATAA
CCCCTTGAAACCCTGTCTTGTCCTCCTGTTACTTGCTTCTGCTGTACAAGATG
TAGCACCTTTTCTCCTCTTTGAACATGGTCTAGTGACACGGTAGCACCAGTT
GCAGGAAGGAGCCAGACTTGTTCTCAGAGCACTGTGTTCACACTTTTCAGCA
AAAATAGCTATGGTTGTAACATATGTATTCCCTTCCTCTGATTTGAAGGCAA
AAATCTACAGTGTTTCTTCACTTCTTTTCTGATCTGGGGCATGAAAAAAGCA
AGATTGAAATTTGAACTATGAGTCTCCTGCATGGCAACAAAATGTGTGTCAC
CATCAGGCCAACAGGCCAGCCCTTGAATGGGGATTTATTACTGTTGTATCTA
TGTTGCATGATAAACATTCATCACCTTCCTCCTGTAGTCCTGCCTCGTACTCC
CCTTCCCCTATGATTGAAAAGTAAACAAAACCCACATTTCCTATCCTGGTTA
GAAGAAAATTAATGTTCTGACAGTTGTGATCGCCTGGAGTACTTTTAGACTT TABLE 3-continued

```
TTAGCATTCGTTTTTTACCTGTTTGTGGATGTGTGTTTGTATGTGCATACGTA
TGAGATAGGCACATGCATCTTCTGTATGGACAAAGGTGGGGTACCTACAGG
AGAGCAAAGGTTAATTTTGTGCTTTTAGTAAAAACATTTAAATACAAAGTTC
TTTATTGGGTGGAATTATATTTGATGCAAATATTTGATCACTTAAAACTTTTA
AAACTTCTAGGTAATTTGCCACGCTTTTTGACTGCTCACCAATACCCTGTAA
AAATACGTAATTCTTCCTGTTTGTGTAATAAGATATTCATATTTGTAGTTGCA
TTAATAATAGTTATTTCTTAGTCCATCAGATGTTCCCGTGTGCCTCTTTTATG
CCAAATTGATTGTCATATTTCATGTTGGGACCAAGTAGTTTGCCCATGGCAA
ACCTAAATTTATGACCTGCTGAGGCCTCTCAGAAAACTGAGCATACTAGCAA
GACAGCTCTTCTTGAAAAAAAAAATATGTATACACAAATATATACGTATATC
TATATATACGTATGTATATACACACATGTATATTCTTCCTTGATTGTGTAGCT
GTCCAAATAATAACATATATAGAGGGAGCTGTATTCCTTTATACAAATCTG
ATGGCTCCTGCAGCACTTTTTCCTTCTGAAAATATTTACATTTTGCTAACCTA
GTTTGTTACTTTAAAAATCAGTTTTGATGAAAGGAGGGAAAAGCAGATGGA
CTTGAAAAGATCCAAGCTCCTATTAGAAAAGGTATGAAAATCTTTATAGTA
AAATTTTTTATAAACTAAAGTTGTACCTTTTAATATGTAGTAAACTCTCATTT
ATTTGGGGTTGGCTCTTGGATCTCATCCATCCATTGTGTTCTCTTTAATGCTG
CCTGCCTTTTGAGGCATTCACTGCCCTAGACAATGCCACCAGAGATAGTGGG
GGAAATGCCAGATGAAACCAACTCTTGCTCTCACTAGTTGTCAGCTTCTCTG
GATAAGTGACCACAGAAGCAGGAGTCCTCCTGCTTGGGCATCATTGGGCCA
GTTCCTTCTCTTTAAATCAGATTTGTAATGGCTCCCAAATTCCATCACATCAC
ATTTAAATTGCAGACAGTGTTTTGCACATCATGTATCTGTTTTGTCCCATAAT
ATGCTTTTTACTCCCTGATCCCAGTTTCTGCTGTTGACTCTTCCATTCAGTTTT
ATTTATTGTGTGTTCTCACAGTGACACCATTTGTCCTTTTCTGCAACAACCTT
TCCAGCTACTTTTGCCAAATTCTATTTGTCTTCTCCTTCAAAACATTCTCCTTT
GCAGTTCCTCTTCATCTGTGTAGCTGCTCTTTTGTCTCTTAACTTACCATTCCT
ATAGTACTTTATGCATCTCTGCTTAGTTCTATTAGTTTTTTGGCCTTGCTCTTC
TCCTTGATTTTAAAATTCCTTCTATAGCTAGAGCTTTTCTTTCTTTCATTCTCT
CTTCCTGCAGTGTTTTGCATACATCAGAAGCTAGGTACATAAGTTAAATGAT
TGAGAGTTGGCTGTATTTAGATTTATCACTTTTTAATAGGGTGAGCTTGAGA
GTTTTCTTTCTTTCTGTTTTTTTTTTGTTTTTTTTTTTTTTTTTTTTTTTTTTT
TTTTGACTAATTTCACATGCTCTAAAAACCTTCAAAGGTGATTATTTTCTCC
TGGAAACTCCAGGTCCATTCTGTTTAAATCCCTAAGAATGTCAGAATTAAAA
TAACAGGGCTATCCCGTAATTGGAAATATTTCTTTTTTCAGGATGCTATAGT
CAATTTAGTAAGTGACCACCAAATTGTTATTTGCACTAACAAAGCTCAAAAC
ACGATAAGTTTACTCCTCCATCTCAGTAATAAAAATTAAGCTGTAATCAACC
TTCTAGGTTTCTCTTGTCTTAAAATGGGTATTCAAAAATGGGGATCTGTGGT
GTATGTATGGAAACACATACTCCTTAATTTACCTGTTGTTGGAAACTGGAGA
AATGATTGTCGGGCAACCGTTTATTTTTATTGTATTTTATTTGGTTGAGGGA
TTTTTTTATAAACAGTTTTACTTGTGTCATATTTAAAATTACTAACTGCCAT
CACCTGCTGGGGTCCTTTGTTAGGTCATTTTCAGTGACTAATAGGGATAATC
CAGGTAACTTTGAAGAGATGAGCAGTGAGTGACCAGGCAGTTTTTCTGCCTT
TAGCTTTGACAGTTCTTAATTAAGATCATTGAAGACCAGCTTTCTCATAAAT
TTCTCTTTTTGAAAAAAAGAAAGCATTTGTACTAAGCTCCTCTGTAAGACAA
CATCTTAAATCTTAAAAGTGTTGTTATCATGACTGGTGAGAGAAGAAAACAT
TTTGTTTTTATTAAATGGAGCATTATTTACAAAAAGCCATTGTTGAGAATTA
GATCCCACATCGTATAAATATCTATTAACCATTCTAAATAAAGAGAACTCCA
GTGTTGCTATGTGCAAGATCCTCTCTTGGAGCTTTTTTGCATAGCAATTAAA
GGTGTGCTATTTGTCAGTAGCCATTTTTTTGCAGTGATTTGAAGACCAAAGT
TGTTTTACAGCTGTGTTACCGTTAAAGGTTTTTTTTTTATATGTATTAAATC
AATTTATCACTGTTTAAAGCTTTGAATATCTGCAATCTTTGCCAAGGTACTTT
TTTATTTAAAAAAAAAACATAACTTTGTAAATATTACCCTGTAATATTATATAT
ACTTAATAAAACATTTTAAGCTATTTTGTTGGGCTATTTCTATTGCTGCTACA
GCAGACCACAAGCACATTTCTGAAAAATTTAATTTATTAATGTATTTTTAAG
TTGCTTATATTCTAGGTAACAATGTAAAGAATGATTTAAAATATTAATTATG
AATTTTTTGAGTATAATACCCAATAAGCTTTTAATTAGAGCAGAGTTTTAATT
AAAAGTTTTAAATCAGTC (SEQ ID NO: 15)
```

Human CD47 amino acid isoform 4 (NP_001768.1)
MWPLVAALLLGSACCGSAQLLFNKTKSVEFTPCNPTVVIPCFVTNMEAQNT
TEVYVKWKFKGRDIYTFDGALNKSTVPTDFSSAKIEVSQLLKGDASLKMDK
SDAVSHTGNYTCEVTELTREGETIIELKYRVVSWFSPNENILIVIFPIFAILLFW
GQFGIKTLKYRSGGMDEKTIALLVAGLVITVIVIVGAILFVPGEYSLKNATGLGLI
VTSTGILILLHYYVFSTAIGLTSFVIAILVIQVIAYILAVVGLSLCIAACIPMHGPLLI
SGLSILALAQLLGLVYMKFVASNQKTIQPPRKAVEEPLNAFKESKGMMNDE (SEQ
ID NO: 16)

Humanized CD47 amino acid isoform 1
MWPLAAALLLGSCCCGSAQLLFNKTKSVFFTFCNDTVVIPCFVTNMEAQNT
TEVYVKWKFKGRDIYTFDGALNKSTVPTDFSSAKIEVSQLLKGDASLKMDK
SDAVSHTGNYTCEVTELTREGETIIELKYRVVSVVFSPNENILIVIFPIFAILLF
WGQFGIKTLKYRSGGMDEKTIALLVAGLVITVIVIVGAILFVPGEYSLKNAT
GLGLIVTSTGILILLHYYVFSTAIGLTSFVIAILVIQVIAYILAVVGLSLCIAACI
PMHGPLLISGLSILALAQLLGLVYMKFVE (SEQ ID NO 17)

Humanized CD47 amino acid isoform 2
MWPLAAALLLGSCCCGSAQLLFNKTKSVEFTPCNPTVVIPCFVTNMEAQNT
TEVYVKWKFKGRDIYTFDGALNKSTVPTDFSSAKIEVSQLLKGDASLKMDK
SDAVSHTGNYTCEVTELTREGETIIELKYRVVSWFSPNENILIVIFPIFAILLF
WGQFGIKTLKYRSGGMDEKTIALLVAGLVITVIVIVGAILFVPGEYSLKNAT

TABLE 3-continued

```
GLGLIVTSTGILILLHYYVFSTAIGLTSFVIAILVIQVIAYILAVVGLSLCIAACI
PMHGPLLISGLSILALAQLLGLVYMKFVASNQRTIQPPRNR (SEQ ID NO: 18)

Humanized CD47 amino acid isoform 3
MWPLAAALLLGSCCCGSAQLLFNKTKSVEFTFCMDTVVIPCFVTMMEAQNT
TEVYVKWKFKGRDIYTFDGALNKSTVPTDFSSAKIEVSQLLKGDASLKMDK
SDAVSHTGNYTCEVTELTREGETHELKYRVVSWFSPNENILIVIFPIFAILLF
WGQFGIKTLKYRSGGMDEKTIALLVAGLVITVIVIVGAILFVPGEYSLKNAT
GLGLIVTSTGILILLIIYYVFSTAIGLTSFVIAILVIQVIAYILAVVGLSLCIAACI
PMHGPLLISGLSILALAQLLGLVYMKFVASNQRTIQPPRKAVEEPLNE (SEQ ID
NO: 19)

Humanized CD47 amino acid isoform 4
MWPLAAALLLGSCCCGSAQLLFNKTKSVEFrFCNPTVVIPCFVTNMEAQMT
TEVYVKWKFKGRDIYTFDGALNKSTVPTDFSSAKIEVSQLLKGDASLKMDK
SDAVSHIGNYICEVTELIREGETIIELKYRWSWFSPNENILIVIFPIFAILLF
WGQFGIKTLKYRSGGMDEKTIALLVAGLVITVIVIVGAILFVPGEYSLKNAT
GLGLIVTSTGILILLHYYVFSTAIGLTSFVIAILVIQVIAYILAVVGLSLCIAACI
PMHGPLLISGLSILALAQLLGLVYMKFVASNQRTIQPPRKAVEEPLNAFKESKG
MMNDE (SEQ ID NO: 20)
```

Humanized CD47 Non-Human Animals

Non-human animals are provided that express humanized CD47 proteins on the surface of cells of the non-human animals resulting from a genetic modification of an endogenous locus of the non-human animal that encodes a CD47 protein. Suitable examples described herein include rodents, in particular, mice.

A humanized CD47 gene, in some embodiments, comprises genetic material from a heterologous species (e.g., humans), wherein the humanized CD47 gene encodes a CD47 protein that comprises the encoded portion of the genetic material from the heterologous species. In some embodiments, a humanized CD47 gene of the present invention comprises genomic DNA of a heterologous species that encodes the extracellular portion of a CD47 protein that is expressed on the plasma membrane of a cell. In some embodiments, a humanized CD47 gene of the present invention comprises genomic DNA of a heterologous species that encodes the extracellular portion and the transmembrane portion of a CD47 protein that is expressed on the plasma membrane of a cell. Non-human animals, embryos, cells and targeting constructs for making non-human animals, non-human embryos, and cells containing said humanized CD47 gene are also provided.

In some embodiments, an endogenous CD47 gene is deleted. In some embodiments, an endogenous CD47 gene is altered, wherein a portion of the endogenous CD47 gene is replaced with a heterologous sequence (e.g., a human CD47 sequence, in whole or in part). In some embodiments, all or substantially all of an endogenous CD47 gene is replaced with a heterologous gene (e.g., a human CD47 gene). In some embodiments, a portion of a heterologous CD47 gene is inserted into an endogenous non-human CD47 gene at an endogenous CD47 locus. In some embodiments, the heterologous gene is a human gene. In some embodiments, the modification or humanization is made to one of the two copies of the endogenous CD47 gene, giving rise to a non-human animal that is heterozygous with respect to the humanized CD47 gene. In other embodiments, a non-human animal is provided that is homozygous for a humanized CD47 gene.

A non-human animal of the present invention contains a human CD47 gene, in whole or in part, at an endogenous non-human CD47 locus. Thus, such non-human animals can be described as having a heterologous CD47 gene. The replaced, inserted, modified or altered CD47 gene at the endogenous CD47 locus can be detected using a variety of methods including, for example, PCR, Western blot, Southern blot, restriction fragment length polymorphism (RFLP), or a gain or loss of allele assay. In some embodiments, the non-human animal is heterozygous with respect to the humanized CD47 gene. In some embodiments, the non-human animal is homozygous for the humanized CD47 gene.

In various embodiments, a humanized CD47 gene according to the present invention includes a CD47 gene that has a second, third, fourth, fifth, sixth and seventh exon each having a sequence at least 50% (e.g., 50%, 55%, 60%, 65%, 70%, 75%, 80%, 85%, 90%, 91%, 92%, 93%, 94%, 95%, 96%, 97%, 98%, 99% or more) identical to a second, third, fourth, fifth, sixth and seventh exon that appear in a human CD47 gene of Table 3.

In various embodiments, a humanized CD47 gene according to the present invention includes a CD47 gene that has a first exon and exon(s) downstream of exon 7 (e.g., eighth and ninth exons of isoform 2) each having a sequence at least 50% (e.g., 50%, 55%, 60%, 65%, 70%, 75%, 80%, 85%, 90%, 91%, 92%, 93%, 94%, 95%, 96%, 97%, 98%, 99% or more) identical to a respective exon that appears in a mouse CD47 gene of Table 3.

In various embodiments, a humanized CD47 gene according to the present invention includes a CD47 gene that has a 5' untranslated region and a 3' untranslated region each having a sequence at least 50% (e.g., 50%, 55%, 60%, 65%, 70%, 75%, 80%, 85%, 90%, 91%, 92%, 93%, 94%, 95%, 96%, 97%, 98%, 99% or more) identical to a 5' untranslated region and a 3' untranslated region that appear in a mouse CD47 gene of Table 3.

In various embodiments, a humanized CD47 gene according to the present invention includes a CD47 gene that has a nucleotide coding sequence (e.g., a cDNA sequence) at least 50% (e.g., 50%, 55%, 60%, 65%, 70%, 75%, 80%, 85%, 90%, 91%, 92%, 93%, 94%, 95%, 96%, 97%, 98%, 99% or more) identical to a nucleotide coding sequence that appears in a human CD47 nucleotide coding sequence of Table 3.

In various embodiments, a humanized CD47 protein produced by a non-human animal of the present invention has an extracellular portion having an amino acid sequence that is at least 50% (e.g., 50%, 55%, 60%, 65%, 70%, 75%, 80%, 85%, 90%, 91%, 92%, 93%, 94%, 95%, 96%, 97%, 98%, 99% or more) identical to an extracellular portion of a human CD47 protein that appears in Table 3.

In various embodiments, a humanized CD47 protein produced by a non-human animal of the present invention has an extracellular portion having an amino acid sequence that is identical to amino acid residues 19-141 that appear in a human CD47 protein of Table 3.

In various embodiments, a humanized CD47 protein produced by a non-human animal of the present invention has an N-terminal immunoglobulin V domain having an amino acid sequence that is at least 50% (e.g., 50%, 55%, 60%, 65%, 70%, 75%, 80%, 85%, 90%, 91%, 92%, 93%, 94%, 95%, 96%, 97%, 98%, 99% or more) identical to an N-terminal immunoglobulin V domain of a human CD47 protein that appears in Table 3.

In various embodiments, a humanized CD47 protein produced by a non-human animal of the present invention has an N-terminal immunoglobulin V domain having an amino acid sequence that is identical to amino acid residues 19-127 that appear in a human CD47 protein of Table 3.

In various embodiments, a humanized CD47 protein produced by a non-human animal of the present invention has an N-terminal immunoglobulin V domain and five transmembrane domains each having a sequence that is at least 50% (e.g., 50%, 55%, 60%, 65%, 70%, 75%, 80%, 85%, 90%, 91%, 92%, 93%, 94%, 95%, 96%, 97%, 98%, 99% or more) identical to an N-terminal immunoglobulin V domain and five transmembrane domains of a human CD47 protein that appears in Table 3.

In various embodiments, a humanized CD47 protein produced by a non-human animal of the present invention has an intracytoplasmic tail having a sequence that is at least 50% (e.g., 50%, 55%, 60%, 65%, 700%, 75%, 80%, 85%, 90%, 91%, 92%, 93%, 94%, 95%, 96%, 97%, 98%, 99% or more) identical to an intracytoplasmic tail of a mouse CD47 protein that appears in Table 3.

In various embodiments, a humanized CD47 protein produced by a non-human animal of the present invention has an amino acid sequence that is at least 50% (e.g., 50%, 55%, 60%, 65%, 70%, 75%, 80%, 85%, 90%, 91%, 92%, 93%, 94%, 95%, 96%, 97%, 98%, 99% or more) identical to amino acid residues 16-292 that appear in a human CD47 protein of Table 3.

In various embodiments, a humanized CD47 protein produced by a non-human animal of the present invention has an amino acid sequence that is at least 50% (e.g., 50%, 55%, 60%, 65%, 70, 75%, 80%, 85%, 90%, 91%, 92%, 93%, 94%, 95%, 96%, 97%, 98%, 99% or more) identical to amino acid residues 19-292 that appear in a human CD47 protein of Table 3.

In various embodiments, a humanized CD47 protein produced by a non-human animal of the present invention has an amino acid sequence that is identical to amino acid residues 19-292 (or 16-292) that appear in a human CD47 protein of Table 3.

In various embodiments, a humanized CD47 protein produced by a non-human animal of the present invention has an amino acid sequence that is at least 500/0 (e.g., 50%, 55%, 60%, 65%, 70%, 75%, 80%, 85%, 90%, 91%, 92%, 93%, 94%, 95%, 96%, 97%, 98%, 99% or more) identical to an amino acid sequence of a humanized CD47 protein that appears in Table 3.

In various embodiments, a humanized CD47 protein produced by a non-human animal of the present invention has an amino acid sequence that is identical to an amino acid sequence of a humanized CD47 protein that appears in Table 3.

Compositions and methods for making non-human animals that express a humanized CD47 protein, including specific polymorphic forms, allelic variants (e.g., single amino acid differences) or alternatively spliced isoforms, are provided, including compositions and methods for making non-human animals that express such proteins from a human promoter and a human regulatory sequence. In some embodiments, compositions and methods for making non-human animals that express such proteins from an endogenous promoter and an endogenous regulatory sequence are also provided. The methods include inserting the genetic material encoding a human CD47 protein in whole or in part at a precise location in the genome of a non-human animal that corresponds to an endogenous CD47 gene thereby creating a humanized CD47 gene that expresses a CD47 protein that is human in whole or in part. In some embodiments, the methods include inserting genomic DNA corresponding to exons 2-7 of a human CD47 gene into an endogenous CD47 gene of the non-human animal thereby creating a humanized gene that encodes a CD47 protein that contains a human portion containing amino acids encoded by the inserted exons.

Where appropriate, the coding region of the genetic material or polynucleotide sequence(s) encoding a human CD47 protein in whole or in part may be modified to include codons that are optimized for expression in the non-human animal (e.g., see U.S. Pat. Nos. 5,670,356 and 5,874,304). Codon optimized sequences are synthetic sequences, and preferably encode the identical polypeptide (or a biologically active fragment of a full length polypeptide which has substantially the same activity as the full length polypeptide) encoded by the non-codon optimized parent polynucleotide. In some embodiments, the coding region of the genetic material encoding a human CD47 protein, in whole or in part, may include an altered sequence to optimize codon usage for a particular cell type (e.g., a rodent cell). For example, the codons of the genomic DNA corresponding to exons 2-7 of a human CD47 gene to be inserted into an endogenous CD47 gene of a non-human animal (e.g., a rodent) may be optimized for expression in a cell of the non-human animal. Such a sequence may be described as a codon-optimized sequence.

A humanized CD47 gene approach employs a relatively minimal modification of the endogenous gene and results in natural CD47-mediated signal transduction in the non-human animal, in various embodiments, because the genomic sequence of the CD47 sequences are modified in a single fragment and therefore retain normal functionality by including necessary regulatory sequences. Thus, in such embodiments, the CD47 gene modification does not affect other surrounding genes or other endogenous CD47-interacting genes (e.g., thrombospondin, SIRPs, integrins, etc.). Further, in various embodiments, the modification does not affect the assembly of a functional CD47 transmembrane protein on the plasma membrane and maintains normal effector functions via binding and subsequent signal transduction through the cytoplasmic portion of the protein which is unaffected by the modification.

A schematic illustration (not to scale) of the genomic organization of an endogenous murine CD47 gene and a human CD47 gene is provided in FIG. 1. An exemplary method for humanizing an endogenous murine CD47 gene using a genomic fragment containing exons 2-7 of a human CD47 gene is provided in FIG. 2. As illustrated, genomic DNA containing exons 2-7 of a human CD47 gene is inserted into an endogenous murine CD47 gene locus by a targeting construct. This genomic DNA includes the portion of the gene that encodes an extracellular portion and transmembrane domains (e.g., amino acid resides 16-292) of a human CD47 protein responsible for ligand binding.

Figure 2:
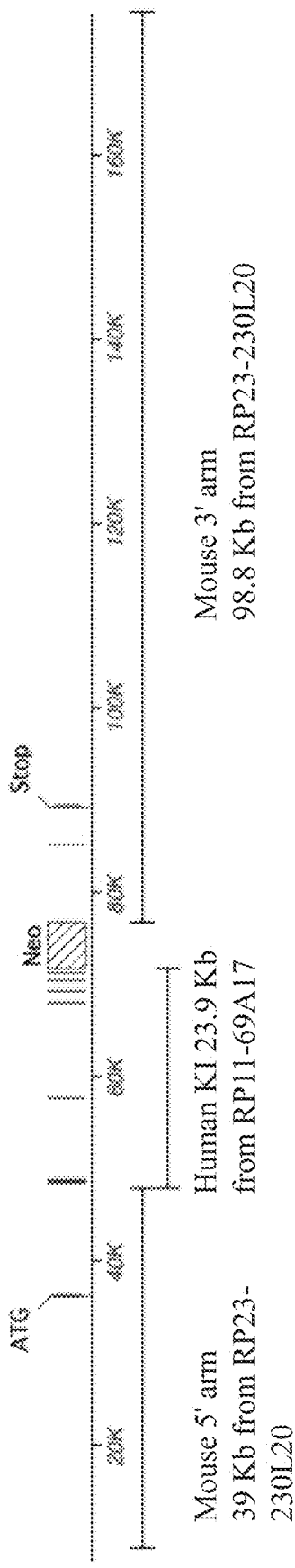
FIG. 2 shows a diagram, not to scale, of an exemplary method for humanization of a non-human Cluster of Differentiation 47 (CD47) gene.
Figure 2:
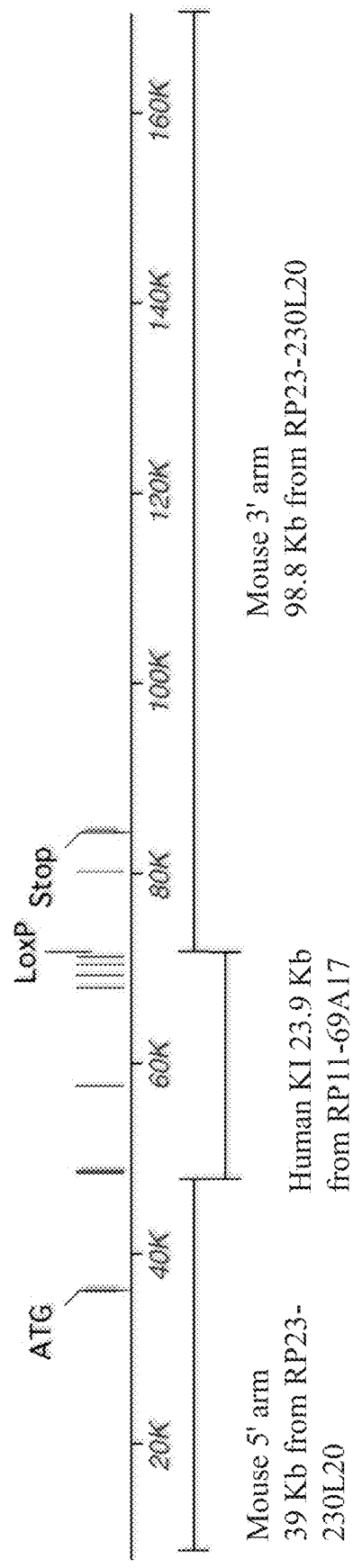

A non-human animal (e.g., a mouse) having a humanized CD47 gene at the endogenous CD47 locus can be made by any method known in the art. For example, a targeting vector can be made that introduces a human CD47 gene in whole or in part with a selectable marker gene. FIG. 2 illustrates an endogenous CD47 locus of a mouse genome comprising an insertion of exons 2-7 of a human CD47 gene. As illustrated, the targeting construct contains a 5' homology arm containing sequence upstream of exon 2 of an endogenous murine CD47 gene (~39 Kb), followed by a genomic DNA fragment containing exons 2-7 of a human CD47 gene (~23.9 Kb), a drug selection cassette (e.g., a neomycin resistance gene flanked on both sides by loxP sequences; ~5 Kb), and a 3' homology arm containing sequence downstream of exon7 of an endogenous murine CD47 gene (~99 Kb). The targeting construct contains a self-deleting drug selection cassette (e.g., a neomycin resistance gene flanked by loxP sequences, see U.S. Pat. Nos. 8,697,851, 8,518,392 and 8,354,389, all of which are incorporated herein by reference). Upon homologous recombination, exons 2-7 of an endogenous murine CD47 gene are replaced by the sequence contained in the targeting vector (i.e., exons 2-7 of a human CD47 gene). A humanized CD47 gene is created resulting in a cell or non-human animal that expresses a humanized CD47 protein that contains amino acids encoded by exons 2-7 of a human CD47 gene. The drug selection cassette is removed in a development-dependent manner, i.e., progeny derived from mice whose germ line cells containing the humanized CD47 gene described above will shed the selectable marker from differentiated cells during development.

The non-human animals of the present invention may be prepared as described above, or using methods known in the art, to comprise additional human or humanized genes, oftentimes depending on the intended use of the non-human animal. Genetic material of such additional human or humanized genes may be introduced through the further alteration of the genome of cells (e.g., embryonic stem cells) having the genetic modifications as described above or through breeding techniques known in the art with other genetically modified strains as desired. In some embodiments, non-human animals of the present invention are prepared to further comprise one or more human or humanized genes selected from SIRPα (CD172a), IL-3, M-CSF, GM-CSF and TPO. In some embodiments, non-human animals of the present invention may be prepared by introducing a targeting vector, as described herein, into a cell from a modified strain. To give but one example, a targeting vector, as described above, may be introduced into a mouse that is Rag2-deficient and IL-2Rγ-deficient and include four human cytokines (Rag2$^{-/-}$IL2Rγc$^{-/-}$; M-CSF$^{Hu}$; IL-3/GM-CSF$^{Hu}$; hSIRPα$^{tg}$; TPO$^{Hu}$). In some embodiments, non-human animals of the present invention are prepared to further comprise a human or humanized signal-regulatory protein alpha (SIRPα) gene. In some embodiments, non-human animals of the present invention comprise a humanized CD47 gene, as described herein, and genetic material from a heterologous species (e.g., humans), wherein the genetic material encodes, in whole or in part, one or more heterologous proteins selected from SIRPα (CD172a), IL-3, M-CSF, GM-CSF and TPO. In some certain embodiments, non-human animals of the present invention comprise a humanized CD47 gene as described herein and genetic material from a heterologous species (e.g., humans), wherein the genetic material encodes, in whole or in part, a heterologous (e.g., human) SIRPα (CD172a) protein. In some certain embodiments, non-human animals of the present invention further comprise a SIRPα gene that comprises an endogenous portion and a human portion (e.g., exons 2-4 of a human SIRPα gene), wherein the human portion encodes the extracellular domain of a SIRPα protein (e.g., amino acids corresponding to residues 28-362 of a human SIRPα protein) and the endogenous portion encodes the intracellular domain of an endogenous SIRPα protein; in some embodiments, the human portion and the endogenous portion are operably linked to an endogenous SIRPα promoter.

For example, as described herein, non-human animals comprising a humanized CD47 gene may further comprise (e.g., via cross-breeding or multiple gene targeting strategies) one or more modifications as described in PCT/US2010/051339, filed Oct. 4, 2010; PCT/US2013/058448, filed Sep. 6, 2013; PCT/US2013/045788, filed Jun. 14, 2013; PCT/US2014/056910, filed Sep. 23, 2014; PCT/US2014/060568, filed Oct. 15, 2014; the PCT/US2012/025040, filed Feb. 14, 2014; PCT/US2012/062,379, filed Oct. 29, 2012; PCT/US2014/064806, filed Nov. 10, 2014; and PCT/US2014/064810, filed Nov. 10, 2014; these applications are incorporated herein by reference in their entirety. In certain embodiments, a rodent comprising a humanized CD47 gene (i.e., exons 2-7 of a human CD47 gene operably linked to exon 1 and exon 8 (and hence any downstream exons) of an endogenous rodent CD47 gene so that the humanized CD47 gene encodes a CD47 polypeptide having an extracellular portion from a human CD47 protein and an intracellular portion from a rodent CD47 protein) is crossed to a rodent comprising a humanized SIRPα gene (e.g., exons 2-4 of a human SIRPα gene operably linked to exons 1 and 5-8 of an endogenous rodent SIRPα gene so that the humanized SIRPα gene encodes a SIRPα polypeptide having an extracellular portion from a human SIRPα protein (e.g., amino acids corresponding to residues 28-362) and an intracellular portion from a rodent SIRPα protein; see, e.g., PCT/US2014/056910, filed Sep. 23, 2014, incorporated herein by reference).

Although embodiments employing a humanized CD47 gene in a mouse (i.e., a mouse with a CD47 gene that encodes a CD47 protein that includes a human portion and a mouse portion) are extensively discussed herein, other non-human animals that comprise a humanized CD47 gene are also provided. In some embodiments, such non-human animals comprise a humanized CD47 gene operably linked to an endogenous CD47 promoter. In some embodiments, such non-human animals express a humanized CD47 protein from an endogenous locus, wherein the humanized CD47 protein comprises amino acid residues 16-292 (or 19-141 or 19-127) of a human CD47 protein. Such non-human animals include any of those which can be genetically modified to express a CD47 protein as disclosed herein, including, e.g., mammals, e.g., mouse, rat, rabbit, pig, bovine (e.g., cow, bull, buffalo), deer, sheep, goat, chicken, cat, dog, ferret, primate (e.g., marmoset, rhesus monkey), etc. For example, for those non-human animals for which suitable genetically modifiable ES cells are not readily available, other methods are employed to make a non-human animal comprising the genetic modification. Such methods include, e.g., modifying a non-ES cell genome (e.g., a fibroblast or an induced pluripotent cell) and employing somatic cell nuclear transfer (SCNT) to transfer the genetically modified genome to a suitable cell, e.g., an enucleated oocyte, and gestating the modified cell (e.g., the modified oocyte) in a non-human animal under suitable conditions to form an embryo.

Methods for modifying a non-human animal genome (e.g., a pig, cow, rodent, chicken, etc. genome) include, e.g., employing a zinc finger nuclease (ZFN) or a transcription activator-like effector nuclease (TALEN) to modify a genome to include a humanized CD47 gene.

In some embodiments, a non-human animal of the present invention is a mammal. In some embodiments, a non-human animal of the present invention is a small mammal, e.g., of the superfamily Dipodoidea or Muroidea. In some embodiments, a genetically modified animal of the present invention is a rodent. In some embodiments, a rodent of the present invention is selected from a mouse, a rat, and a hamster. In some embodiments, a rodent of the present invention is selected from the superfamily Muroidea. In some embodiments, a genetically modified animal of the present invention is from a family selected from Calomyscidae (e.g., mouse-like hamsters), Cricetidae (e.g., hamster, New World rats and mice, voles), Muridae (true mice and rats, gerbils, spiny mice, crested rats), Nesomyidae (climbing mice, rock mice, with-tailed rats, Malagasy rats and mice), Platacanthomyidae (e.g., spiny dormice), and Spalacidae (e.g., mole rats, bamboo rats, and zokors). In some certain embodiments, a genetically modified rodent of the present invention is selected from a true mouse or rat (family Muridae), a gerbil, a spiny mouse, and a crested rat. In some certain embodiments, a genetically modified mouse of the present invention is from a member of the family Muridae. In some embodiment, a non-human animal of the present invention is a rodent. In some certain embodiments, a rodent of the present invention is selected from a mouse and a rat. In some embodiments, a non-human animal of the present invention is a mouse.

In some embodiments, a non-human animal of the present invention is a rodent that is a mouse of a C57BL strain selected from C57BL/A, C57BL/An, C57BL/GrFa, C57BL/KaLwN, C57BL/6, C57BL/6J, C57BL/6ByJ, C57BL/6NJ, C57BL/10, C57BL/10ScSn, C57BL/10Cr, and C57BL/Ola. In some certain embodiments, a mouse of the present invention is a 129 strain selected from the group consisting of a strain that is 129P1, 129P2, 129P3, 129X1, 129S1 (e.g., 129S1/SV, 129S1/SvIm), 129S2, 129S4, 129S5, 129S9/SvEvH, 129/SvJae, 129S6 (129/SvEvTac), 129S7, 129S8, 129T1, 129T2 (see, e.g., Festing et al., 1999, *Mammalian Genome* 10:836; Auerbach, W. et al., 2000, *Biotechniques* 29(5):1024-1028, 1030, 1032). In some certain embodiments, a genetically modified mouse of the present invention is a mix of an aforementioned 129 strain and an aforementioned C57BL/6 strain. In some certain embodiments, a mouse of the present invention is a mix of aforementioned 129 strains, or a mix of aforementioned BL/6 strains. In some certain embodiments, a 129 strain of the mix as described herein is a 129S6 (129/SvEvTac) strain. In some embodiments, a mouse of the present invention is a BALB strain, e.g., BALB/c strain. In some embodiments, a mouse of the present invention is a mix of a BALB strain and another aforementioned strain.

In some embodiments, a non-human animal of the present invention is a rat. In some certain embodiments, a rat of the present invention is selected from a Wistar rat, an LEA strain, a Sprague Dawley strain, a Fischer strain, F344, F6, and Dark Agouti. In some certain embodiments, a rat strain as described herein is a mix of two or more strains selected from the group consisting of Wistar, LEA, Sprague Dawley, Fischer, F344, F6, and Dark Agouti.

Methods Employing Non-Human Animals Having Humanized CD47 Genes

CD47 mutant and transgenic non-human animals (e.g., miniature swine) and cells have been reported (Koshimizu H. et al. (2014) *PLoS One*, 9(2):e89584; Lavender, K. J. et al. (2014) *J. Immunol. Methods*, 407:127-134; Tena, A. et al. (2014) *Am. J. Transplant*.doi: 10.1111/ajt.12918; Lavender K. J. et al. (2013) *Blood*, 122(25):4013-4020; Tena, A. et al. (2012) *Transplantation* 94(10S):776; Wang, C. et al. (2011) *Cell Transplant.* 20(11-12): 1915-1920; Johansen, M. L. and Brown, E. J. (2007) *J. Biol. Chem.* 282:24219-24230; Wang, H. et al. (2007) *Proc. Nat. Acad. Sci. U.S.A.* 104:13744-13749; Tulasne D. et al. (2001) *Blood*, 98(12):3346-52; Oldenborg, P. et al. (2000) *Science* 288:2051-2054; Verdrengh, M. et al. (1999) *Microbes Infect.* 1(10):745-751; Chang, H. P. et al. (1999) *Learn Afem.* 6(5):448-457; Wang, X. Q. et al. (1999) *J. Cell Biol.* 147(2):389-400; Lindberg, F. P. et al. (1996) *Science* 274(5288):795-798). Such animals have been employed in a variety of assays to determine, for example, the molecular aspects of CD47 expression, function and regulation. Considerable species differences have been discovered. Indeed, nonobese diabetic/severe combined immunodeficient (NOD/SCID) mice express a SIRPα protein that is capable of interacting with human CD47 and, therefore, have been used extensively for the development of mouse models with components of the human immune system (e.g., see Takenaka, K. et al. (2007) *Nat. Immunol.* 8(120:1313-1323). The SIRPα allele present in these mice is not representative of the SIRPα allele present in other mouse strains and, generally, there is little cross-reaction between CD47 and SIRPα between species. Also, CD47 on mouse cells has been reported to have a near-complete mobility, while CD47 on human cells demonstrate only about 30-40/o (Bruce, L. et al. (2003) *Blood* 101:4180-4188; Mouro-Chanteloup, L. et al. (2000) *VoxSanguinis* 78:P030; Mouro-Chanteloup, L. et al. (2003) *Blood* 101:338-344). Thus, NOD/SCID mice are not without limitation. For example, although multi-lineage human hematopoietic development can be supported in some genetic backgrounds (e.g., BALB/c Rag2$^{-/-}$IL-2Rγc$^{-/-}$), homeostasis of other cell types remains inefficient (e.g., T and NK cells; see e.g., Gimeno, R. et al. (2004) *Blood* 104:3886-3893; Traggiai, E. et al. (2004) *Science* 304:104-107; Legrand, N. et al. (2006) *Blood* 108:238-245). Further, CD47 is also known to interact with other cell surface proteins and provide bidirectional signaling. Thus, existing mice represent an inefficient in vivo system for elucidation of CD47-dependent functions in various biological processes such as, for example, engraftment and phagocytosis. Further, existing mice represent a suboptimal in vivo system for development of CD47 targeted therapies.

Non-human animals of the present invention provide an improved in vivo system and source of biological materials (e.g., cells) expressing human CD47 that are useful for a variety of assays. In various embodiments, non-human animals of the present invention are used to develop therapeutics that target CD47 and/or modulate CD47-SIRPα signaling. In various embodiments, non-human animals of the present invention are used to screen and develop candidate therapeutics (e.g., antibodies) that bind human CD47. In various embodiments, non-human animals of the present invention are used to screen and develop candidate therapeutics (e.g., antibodies) that block interaction of human CD47 with human SIRPα. In various embodiments, non-human animals of the present invention are used to determine the binding profile of antagonists and/or agonists of a humanized CD47 on the surface of a cell of a non-human animal as described herein. In some embodiments, non-human animals of the present invention are used to determine the epitope or epitopes of one or more candidate therapeutic antibodies that bind human CD47.

In various embodiments, non-human animals of the present invention are used to determine the pharmacokinetic profiles of anti-CD47 antibodies. In various embodiments, one or more non-human animals of the present invention and one or more control or reference non-human animals are each exposed to one or more candidate therapeutic anti-CD47 antibody at various doses (e.g., 0.1 mg/kg, 0.2 mg/kg, 0.3 mg/kg, 0.4 mg/kg, 0.5 mg/kg, 1 mg/kg, 2 mg/kg, 3 mg/kg, 4 mg/kg, 5 mg/mg, 7.5 mg/kg, 10 mg/kg, 15 mg/kg, 20 mg/kg, 25 mg/kg, 30 mg/kg, 40 mg/kg, or 50 mg/kg or more). Candidate therapeutic antibodies may be dosed via any desired route of administration (e.g., subcutaneously, intravenously, intramuscular, intraperitoneal, etc.). Blood is isolated from non-human animals (humanized and control) at various time points (e.g., 0 hr, 6 hr, 1 day, 2 days, 3 days, 4 days, 5 days, 6 days, 7 days, 8 days, 9 days, 10 days, 11 days, or up to 30 or more days). Various assays may be performed to determine the pharmacokinetic profiles of administered candidate therapeutic antibodies using samples obtained from non-human animals as described herein including, but not limited to, total IgG, anti-therapeutic antibody response, agglutination, etc.

In various embodiments, non-human animals of the present invention are used to measure the therapeutic effect of blocking or modulating CD47 signaling and the effect on gene expression as a result of cellular changes. In various embodiments, a non-human animal of the present invention or cells isolated therefrom are exposed to a candidate therapeutic that binds to a humanized CD47 protein (or a human portion of a CD47 protein) on the surface of a cell of the non-human animal and, after a subsequent period of time, analyzed for effects on CD47-dependent processes, for example, adhesion, angiogenesis, apoptosis, inflammation, migration, phagocytosis, proliferation and clearance of tumors (or tumor cells).

Non-human animals of the present invention express humanized CD47 protein, thus cells, cell lines, and cell cultures can be generated to serve as a source of humanized CD47 for use in binding and functional assays, e.g., to assay for binding or function of a CD47 antagonist or agonist, particularly where the antagonist or agonist is specific for a human SIRPα sequence or epitope. In various embodiments, CD47 epitopes bound by candidate therapeutic antibodies can be determined using cells isolated from non-human animals of the present invention.

Cells from non-human animals of the present invention can be isolated and used on an ad hoc basis, or can be maintained in culture for many generations. In various embodiments, cells from a non-human animal of the present invention are immortalized and maintained in culture indefinitely (e.g., in serial cultures).

In various embodiments, cells and/or non-human animals of the present invention are used in a survival and/or proliferation assay (e.g., employing B or T cells) to screen and develop candidate therapeutics that modulate human CD47 signaling. Activation or loss of CD47 can play an important role in the regulation of cell proliferation, and induction of apoptosis by CD47 may result from the activation of specific epitopes of the extracellular domain of CD47, therefore, candidate CD47 modulators (e.g., antagonists or agonists) may be identified, characterized and developed using cells of non-human animals of the present invention and/or a non-human animal as described herein. In some embodiments, cells and/or non-human animals of the present invention are used in survival or death assay(s) to determine the effect on proliferation or apoptosis of a specific cell(s) (e.g., cancer cells) in the presence and absence of CD47.

In various embodiments, cells and/or non-human animals of the present invention are used in xenotransplantation of heterologous (e.g., human) cells to determine the CD47-mediated functions in the physiological (e.g., immune) response to the transplanted human cells. In some embodiments, candidate therapeutics that bind, or block one or more functions of, human CD47 are characterized in a non-human animal of the present invention. Suitable measurements include various cellular assays, proliferation assays, serum immunoglobulin analysis (e.g., antibody titer), cytotoxicity assays, and characterization of ligand-receptor interactions (immunoprecipitation assays). In some embodiments, non-human animals of the present invention are used to characterize the CD47-mediated functions regulating an immune response to an antigen. In some embodiments, the antigen is associated with a neoplasm. In some embodiments, the antigen is associated with an autoimmune disease or condition. In some embodiments, the antigen is a target associated with a disease or condition suffered by one or more human patients in need of treatment.

In various embodiments, non-human animals of the present invention are used in transplantation or adoptive transfer experiments to determine the therapeutic potential of compounds or biological agents to modulate CD47-dependent regulation of new lymphocytes and their immune function. In various embodiments, non-human animals of the present invention are transplanted with human B cells.

In various embodiments, cells of non-human animals of the present invention are used in a cell migration or spreading assay to screen and develop candidate therapeutics that modulate human CD47. Such processes are necessary for many cellular processes including wound healing, differentiation, proliferation and survival.

In various embodiments, cells of non-human animals of the present invention are used in phagocytosis assays to determine the therapeutic potential of compounds or biological agents to modulate CD47-dependent regulation of phagocytosis.

In various embodiments, cells of non-human animals of the present invention are used in tumor cell growth (or proliferation) assays to determine the therapeutic potential of compounds or biological agents to modulate CD47-dependent regulation and/or apoptosis of tumor cells.

In various embodiments, an inflammatory disease or condition is induced in one or more non-human animals of the present invention to provide an in vivo system for determining the therapeutic potential of compounds or biological agents to modulate CD47-dependent regulation of one or more functions of the inflammatory disease or condition. In some embodiments, the inflammatory disease or condition is associated with a neoplasm.

In various embodiments, an anti-angiogenic condition is induced in one or more non-human animals of the present invention to provide an in vivo system for determining the therapeutic potential of compounds or biological agents to modulate CD47-dependent regulation of one or more functions of the anti-angiogenic condition. Exemplary functions that can be evaluated to determine therapeutic efficacy include chemokine expression, nitric oxide (NO)-stimulated responses and blood flow recovery.

Non-human animals of the present invention provide an in vivo system for the analysis and testing of a drug or vaccine. In various embodiments, a candidate drug or vaccine may be delivered to one or more non-human animals of the present invention, followed by monitoring of the non-human animals to determine one or more of the immune response to the drug or vaccine, the safety profile of the drug or vaccine, or the effect on a disease or condition. Exemplary methods used to determine the safety profile include measurements of toxicity, optimal dose concentration, efficacy of the drug or vaccine, and possible risk factors. Such drugs or vaccines may be improved and/or developed in such non-human animals.

Non-human animals of the present invention provide an in vivo system for assessing the pharmacokinetic properties of a drug targeting CD47. In various embodiments, a drug targeting CD47 may be delivered or administered to one or more non-human animals of the present invention, followed by monitoring of, or performing one or more assays on, the non-human animals (or cells isolated therefrom) to determine the effect of the drug on the non-human animal. Pharmacokinetic properties include, but are not limited to, how an animal processes the drug into various metabolites (or detection of the presence or absence of one or more drug metabolites, including, toxic metabolites), drug half-life, circulating levels of drug after administration (e.g., serum concentration of drug), anti-drug response (e.g., anti-drug antibodies), drug absorption and distribution, route of administration, routes of excretion and/or clearance of the drug. In some embodiments, pharmacokinetic and pharmacodynamic properties of drugs (e.g., CD47 modulators) are monitored in or through the use of non-human animals of the present invention.

Non-human animals of the present invention provide an in vivo system for assessing the on-target toxicity of a drug targeting CD47. In various embodiments, a drug targeting CD47 may be delivered or administered to one or more non-human animals of the present invention, followed by monitoring of or performing one or more assays on the non-human animals (or cells isolated therefrom) to determine the on-target toxic effect of the drug on the non-human animal. Typically, drugs are intended to modulate one or more functions of their targets. To give but one example, a CD47 modulator is intended to modulate CD47-mediated functions (e.g., CD47 induced apoptosis) through interacting in some way with the CD47 molecule on the surface of one or more cells. In some embodiments, such a modulator may have an adverse effect that is an exaggeration of the desired pharmacologic action(s) of the modulator. Such effects are termed on-target effects. Exemplary on-target effects include too high of a dose, chronic activation/inactivation, and correct action in an incorrect tissue. In some embodiments, on-target effects of a drug targeting CD47 identified in or through the use of non-human animals of the present invention are used to determine a previously unknown function(s) of CD47.

Non-human animals of the present invention provide an in vivo system for assessing the off-target toxicity of a drug targeting CD47. In various embodiments, a drug targeting CD47 may be delivered or administered to one or more non-human animals of the present invention, followed by monitoring of or performing one or more assays on the non-human animals (or cells isolated therefrom) to determine the off-target toxic effect of the drug on the non-human animal. Off-target effects can occur when a drug interacts with an unintended target (e.g., cross-reactivity to a common epitope). Such interactions can occur in an intended or unintended tissue. To give but one example, mirror image isomers (enantiomers) of a drug can lead to off-target toxic effects. Further, a drug can inappropriately interact with and unintentionally activate different receptor subtypes. Exemplary off-target effects include incorrect activation/inhibition of an incorrect target regardless of the tissue in which the incorrect target is found. In some embodiments, off-target effects of a drug targeting CD47 are determined by comparing the effects of administering the drug to non-human animals of the present invention to one or more reference non-human animals.

In some embodiments, performing an assay includes determining the effect on the phenotype (e.g., change in body weight) and/or genotype of the non-human animal to which the drug is administered. In some embodiments, performing an assay includes determining lot-to-lot variability for a CD47 modulator (e.g., an antagonist or an agonist). In some embodiments, performing an assay includes determining the differences between the effects of a drug targeting CD47 administered to a non-human animal of the present invention and a reference non-human animal. In various embodiments, reference non-human animals may have a modification as described herein, a modification that is different as described herein (e.g., one that has a disruption, deletion or otherwise non-functional CD47 gene) or no modification (i.e., a wild-type non-human animal).

Exemplary parameters that may be measured in non-human animals (or in and/or using cells isolated therefrom) for assessing the pharmacokinetic properties, on-target toxicity, and/or off-target toxicity of a drug targeting CD47 include, but are not limited to, agglutination, autophagy, cell division, cell death, complement-mediated hemolysis, DNA integrity, drug-specific antibody titer, drug metabolism, gene expression arrays, hematocrit levels, hematuria, metabolic activity, mitochondrial activity, oxidative stress, phagocytosis, protein biosynthesis, protein degradation, protein secretion, stress response, target tissue drug concentration, non-target tissue drug concentration, transcriptional activity and the like. In various embodiments, non-human animals of the present invention are used to determine a pharmaceutically effective dose of a CD47 modulator.

Non-human animals of the present invention provide an improved in vivo system for the development and characterization of candidate therapeutics for use in cancer. In various embodiments, non-human animals of the present invention may be implanted with a tumor, followed by administration of one or more candidate therapeutics. In some embodiments, candidate therapeutics may include a multi-specific antibody (e.g., a bi-specific antibody) or an antibody cocktail; in some embodiments, candidate therapeutics include combination therapy such as, for example, administration of mono-specific antibodies dosed sequentially or simultaneously. The tumor may be allowed sufficient time to be established in one or more locations within the non-human animal. Tumor cell proliferation, growth, etc. may be measured both before and after administration with the candidate therapeutic(s). Cytotoxicity of candidate therapeutics may also be measured in the non-human animal as desired.

Non-human animals of the present invention provide improved in vivo system elucidating mechanisms of human cell-to-cell interaction through adoptive transfer. In various embodiments, non-human animals of the present invention may by implanted with a tumor xenograft, followed by a second implantation of tumor infiltrating lymphocytes could be implanted in the non-human animals by adoptive transfer to determine the effectiveness in eradication of solid tumors or other malignancies. Such experiments may be done with human cells due to the exclusive presence of human CD47 without competition with endogenous CD47 of the non-human animal. Alternatively, such experiments may include the use of mouse cells from a NOD/SCID or BRG (BALB/c Rag2$^{-/-}$IL-2Rγc$^{-/-}$) background. Further, therapies and pharmaceuticals for use in xenotransplantation can be improved and/or developed in such non-human animals.

Non-human animals of the present invention provide an improved in vivo system for maintenance and development of human hematopoietic stem cells through engraftment. In various embodiments, non-human animals of the present invention provide improved development and maintenance of human stem cells within the non-human animal. In various embodiments, increased populations of differentiated human B and T cells are observed in the blood, bone marrow, spleen and thymus of the non-human animal. In various embodiments, optimal T and NK cell homeostasis is observed in cells in the blood, bone marrow, spleen and thymus of the non-human animal. In various embodiments, non-human animals of the present invention demonstrate an increase in the level or amount of red blood cells (RBCs) as compared to one or more reference non-human animals.

Non-human animals of the present invention can be employed to assess the efficacy of a therapeutic drug targeting human cells. In various embodiments, a non-human animal of the present invention is transplanted with human cells, and a drug candidate targeting such human cells is administered to such non-human animal. The therapeutic efficacy of the drug is then determined by monitoring the human cells in the non-human animal after the administration of the drug. Drugs that can be tested in the non-human animals include both small molecule compounds, i.e., compounds of molecular weights of less than 1500 kD, 1200 kD, 1000 kD, or 800 daltons, and large molecular compounds (such as proteins, e.g., antibodies), which have intended therapeutic effects for the treatment of human diseases and conditions by targeting (e.g., binding to and/or acting on) human cells.

In some embodiments, the drug is an anti-cancer drug, and the human cells are cancer cells, which can be cells of a primary cancer or cells of cell lines established from a primary cancer. In these embodiments, a non-human animal of the present invention is transplanted with human cancer cells, and an anti-cancer drug is given to the non-human animal. The efficacy of the drug can be determined by assessing whether growth or metastasis of the human cancer cells in the non-human animal is inhibited as a result of the administration of the drug.

In specific embodiments, the anti-cancer drug is an antibody molecule, which binds to an antigen on human cancer cells. In particular embodiments, the anti-cancer drug is a bi-specific antibody that binds to an antigen on human cancer cells, and to an antigen on other human cells, for example, cells of the human immune system (or "human immune cells") such as B cells and T cells.

In some embodiments, a non-human animal of the present invention is engrafted with human immune cells or cells that differentiate into human immune cells. Such non-human animal with engrafted human immune cells is transplanted with human cancer cells, and is administered an anti-cancer drug, such as a bi-specific antibody that binds to an antigen on human cancer cells and to an antigen on human immune cells (e.g., T cells). The therapeutic efficacy of the bi-specific antibody can be evaluated based on its ability to inhibit growth or metastasis of the human cancer cells in the non-human animal. In a specific embodiment, the non-human animal of the present invention is engrafted with human CD34$^+$ hematopoietic progenitor cells which give rise to human immune cells (including T cells, B cells, NK cells, among others). Human B cell lymphoma cells (e.g., Raji cells) are transplanted into such non-human animal with engrafted human immune cells, which is then administered with a bi-specific antibody that binds to tumor antigen (e.g., an antigen on normal B cells and certain B cell malignancies such as CD20) and to the CD3 subunit of the T cell receptor, to test the ability of the bi-specific antibody to inhibit tumor growth in the non-human animal.

EXAMPLES

The following examples are provided so as to describe to those of ordinary skill in the art how to make and use methods and compositions of the invention, and are not intended to limit the scope of what the inventors regard as their invention. Unless indicated otherwise, temperature is indicated in Celsius, and pressure is at or near atmospheric.

Example 1. Humanization of an Endogenous Cluster of Differentiation 47 (CD47) Gene This example illustrates exemplary methods of humanizing an endogenous gene encoding cluster of differentiation 47 (CD47) in a non-human mammal such as a rodent (e.g., a mouse). The methods described in this example can be employed to humanize an endogenous CD47 gene of a non-human animal using any human sequence, or combination of human sequences (or sequence fragments) as desired. In this example, a human CD47 gene that appears in bacterial artificial chromosome (BAC) clone RP11-69A17 is employed for humanizing an endogenous CD47 gene of a mouse.

A targeting vector for humanization of the genetic material encoding an extracellular N-terminal IgV domain and five transmembrane domains of an endogenous CD47 gene was constructed using VELOCIGENE® technology (see, e.g., U.S. Pat. No. 6,586,251 and Valenzuela et al. (2003) High-throughput engineering of the mouse genome coupled with high-resolution expression analysis, *Nature Biotech.* 21(6):652-659; incorporated herein by reference).

Briefly, mouse bacterial artification chromosome (BAC) clone RP23-230L20 (Invitrogen) was modified to delete the sequence containing exons 2-7 of an endogenous CD47 gene and insert exons 2-7 of a human CD47 gene using human BAC clone RP11-69A 17 (Invitrogen), which encodes amino acids 16-292 of a human CD47 polypeptide. Endogenous DNA containing genomic DNA corresponding to exons 1, 8 and 9 of isoform 2 as well as the 5' and 3' untranslated regions (UTRs) were retained. Sequence analysis of the human CD47 sequence contained in BAC clone RP11-69A17 confirmed all CD47 exons and splicing signals. Sequence analysis revealed that the sequence matched the reference genome and CD47 transcripts NM_001777.3 and NM_198793.2. The genomic DNA corresponding to exons 2-7 of an endogenous CD47 gene (~30.8 kb) was replaced in BAC clone RP23-230L20 by homologous recombination in bacterial cells to insert a DNA fragment containing ~23.9 kb of genomic human DNA corresponding to exons 2-7 of a human CD47 gene from BAC clone RP11-69A17and ~4995 bp corresponding to a self-deleting neomycin cassette flanked by recombinase recognition sites (loxP-hUb1-em7-Neo-pA-mPrm1-Crei-loxP; see U.S. Pat. Nos. 8,697,851, 8,518,392 and 8,354,389, which are incorporated herein by reference). The self-deleting neomycin cassette was added to the end of the ~23.9 kb human DNA fragment containing exons 2-7 of the human CD47 gene (FIG. 2). The targeting vector contained, from 5' to 3', a 5' homology arm containing ~39 kb of mouse genomic DNA from BAC clone RP23-230L20, ~29.3 kb of human genomic DNA from BAC clone RP11-69A17 (containing exons 2-7 of a human CD47 gene), a self-deleting neomycin cassette flanked by loxP sites, and ~98.8 kb of mouse genomic DNA from BAC clone RP23-230L20. After homolgous recombination in bacterial cells with the targeting vector described above, a modified RP23-230L20 BAC clone was created that resulted in a humanized CD47 gene which contained a mouse 5' UTR, a mouse exon 1, human exons 2-7, mouse exons 8-9 and a mouse 3'UTR. Protein sequences of four projected alternatively spliced isoforms of humanized CD47 are provided in Table 3 which indicate the resulting mouse and human amino acids encoded by the mouse and human DNA, respectively.

Figure 3:
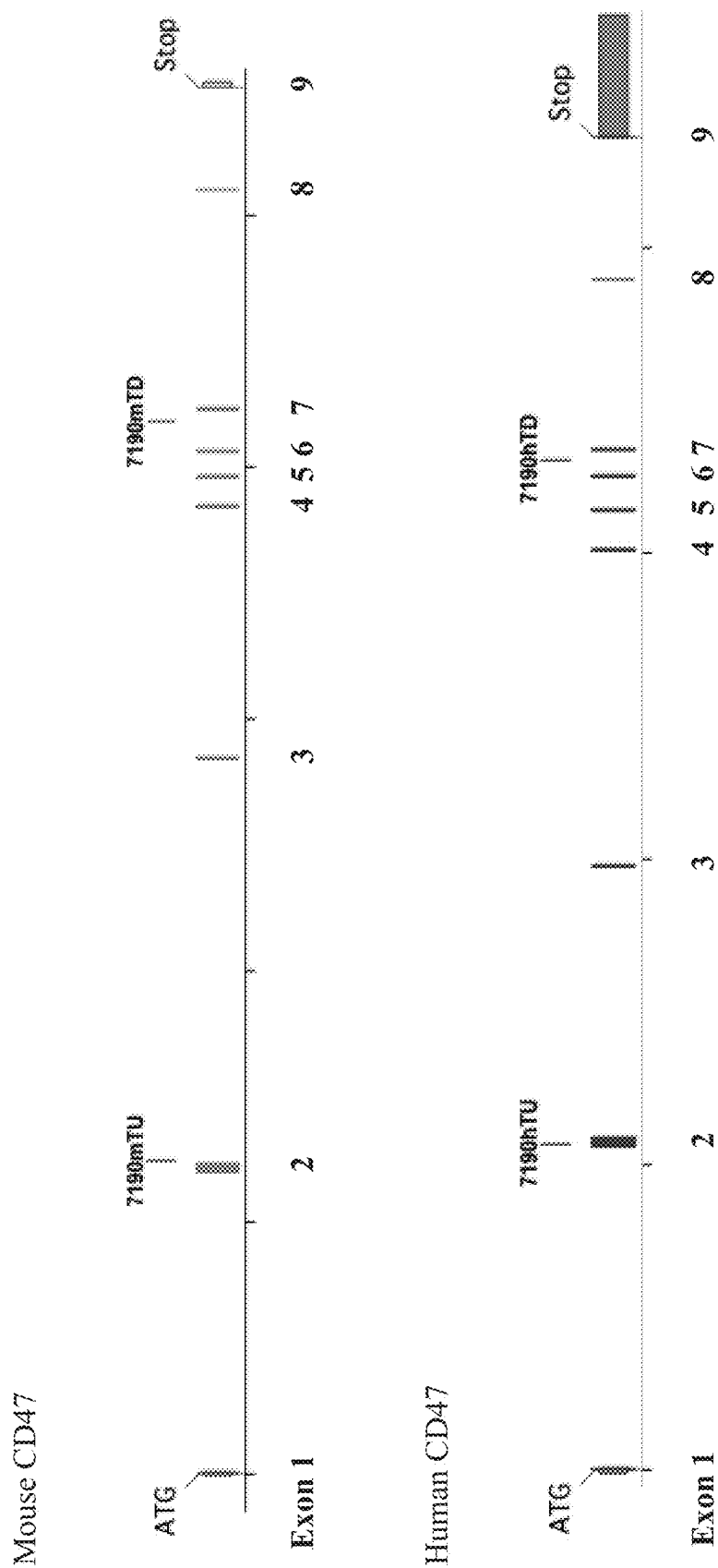
FIG. 3 shows a diagram, not to scale, of the genomic organization of a mouse and human Cluster of Differentiation 47 (CD47) genes. Locations of probes used in an assay described in Example 1 are indicated.

The modified BAC clone described above was used to electroporate F1H4 (50% 129/S6/SvEv/Tac, 50% C57BL/6NTac; Auerbach, W. et al. (2000) *Biotechniques* 29(5): 1024-8, 1030, 1032) mouse embryonic stem (ES) cells to create modified ES cells comprising an endogenous CD47 gene that is humanized from exons 2-7. Positively targeted ES cells containing a humanized CD47 gene were identified by an assay (Valenzuela et al., supra) that detected the presence of the human CD47 sequences (e.g., exons 2-7) and confirmed the loss and/or retention of mouse CD47 sequences (e.g., exons 1, 8 and 9 and/or exons 2-7). Table 4 sets forth the primers and probes that were used to confirm humanization of an endogenous CD47 gene as described above (FIG. 3). The nucleotide sequence across the upstream insertion point included the following, which indicates endogenous mouse sequence upstream of the insertion point (contained within the parentheses below with an AsiSI restriction site italicized) linked contiguously to a human CD47 sequence present at the insertion point: (GCAGACATGA TTACTTCAGA GCTTTCAAAG CTAGATACTG TACCTTGCAT ATTCCAACAC) GCGA TCGC ATTTTAAGAT TTTCCATCCT AGTGGAAAGA TATGATTTGA TTCATCCTAT TTACTTTGTA TATTAAAGTA CAGTAGAACC TGCCACTTTT (SEQ ID NO: 33). The nucleotide sequence across the downstream insertion point at the 5' end of the self-deleting neomycin cassette included the following, which indicates human CD47 genomic sequence contiguous with cassette sequence downstream of the insertion point (contained within the parentheses below with loxP sequence italicized): GGATCCATTT TAAGTAATAG AATAGGATTT TTAATTGTTC CAGTGTTTCT GTGATAGAGC TGTCCTGCAC AGACCTGTTT (CTCGAGATAA CTTCGTATAA TGTATGCTAT ACGAAGTTA T ATGCATGGCC TCCGCGCCGG GTTTTGGCGC CTCCCGCGGG) (SEQ ID NO: 34). The nucleotide sequence across the downstream insertion point at the 3' end of the neomycin cassette included the following, which indicates cassette sequence contiguous with mouse genomic sequence 3' of exon 7 of an endogenous CD47 gene (contained within the parentheses below with loxP sequence italicized): CATGTCTGGA A TAACTTCGTA 1A4 TGT4 TG CTATACGAAG TTATGCTAGT AACTATAACG GTCCTAAGGT AGCGACTAGC (ATTAGTATGG AAGGTCCGTC CACTGTCCAG GTTCCTCTTG CGGAGCTCTT TGTCTCTCTG GACTCTGTAT ACACTGCTTG) (SEQ ID NO: 35). The nucleotide sequence across the downstream insertion point after deletion of the neomycin cassette (76 bp remaining) included the following, which indicates human and mouse genomic sequence juxtaposed with remaining cassette sequence loxP sequence (contained within the parentheses below with loxP sequence italicized): GGATCCATTT TAAGTAATAG AATAGGATTT TTAATTGTTC CAGTGTTTCT GTGATAGAGC TGTCCTGCAC AGACCTGTTT (CTCGAGATAA CTTCGTA TAA 7G TA TGCTA T ACGAAGTTA T GCTAGTAACT ATAACGGTCC TAAGGTAGCG ACTAGC)ATT AGTATGGAAG GTCCGTCCAC TGTCCAGGTT CCTCTTGCGG AGCTCTTTGT CTCTCTGGAC TCTGTATACA CTGCTTGCAT (SEQ ID NO: 36).

Positive ES cell clones were then used to implant female mice using the VELOCIMOUSE® method (see, e.g., U.S. Pat. No. 7,294,754 and Poueymirou et al., F0 generation mice that are essentially fully derived from the donor gene-targeted ES cells allowing immediate phenotypic analyses, 2007, *Nature Biotech.* 25(1):91-99) to generate a litter of pups containing an insertion of exons 2-7 of a human CD47 gene into an endogenous CD47 gene of a mouse. Mice bearing the humanization of exons 2-7 of an endogenous CD47 gene were again confirmed and identified by genotyping of DNA isolated from tail snips using a modification of allele assay (Valenzuela et al., supra) that detected the presence of the human CD47 gene sequences. Pups are genotyped and cohorts of animals heterozygous for the humanized CD47 gene construct are selected for characterization.

TABLE 4

| Name | Primer | Sequence (5'-3') |
| --- | --- | --- |
| 7190mTU | Forward | TGCAGAAGTCACTAGGAGGAAT (SEQ ID NO:2 1) |
|  | Probe | TCAGTCAACTTGTTCTGGGTTGTTT (SEQ ID NO: 22) CC |
|  | Reverse | GTGCCAGACTCAGTTTCTATCCA (SEQ ID NO: 23) |
| 7190mTD | Forward | TGCTGCCAATATACGGCTTCTG (SEQ ID NO: 24) |
|  | Probe | CAGCTCTCATAGCCAACTATGGTG (SEQ ID NO: 25) CC |
|  | Reverse | TCAAGCAGAGCCTGGTTATCTG (SEQ ID NO: 26) |
| 7190hTU | Forward | GTCGTCATTCCATGCTTTGTTAC (SEQ ID NO: 27) |
|  | Probe | TGGAGGCACAAAACACTACTGAAG (SEQ ID NO: 28) TATACG |
|  | Reverse | GGACAGTGGACTTGTTTAGAGC (SEQ ID NO: 29) |
| 7190hTD | Forward | GGCTTGGTGGCTGATTGTTCT (SEQ ID NO: 30 |
|  | Probe | AGCACCCAAACTGATATGCCTGTA (SEQ ID NO: 31) TTTG |
|  | Reverse | TGGGAACTGGTGTTTCAAGTCTA (SEQ ID NO: 32) |

Example 2. Expression of Humanized CD47 Polypeptide by Mouse Red Blood Cells This Example demonstrates that non-human animals (e.g., rodents) modified to contain a humanized CD47 gene according to Example 1 can be used to screen CD47 modulators (e.g., anti-CD47 antibodies) and determine various characterisitics such as, for example, pharamcokinetics and safety profiles. In this Example, several anti-CD47 antibodies are screened on mouse red blood cells (RBCs) isolated from rodents made in accordance with Example 1, which rodents express a humanized CD47 polypeptide as described herein.

Briefly, 2 mL of whole blood from humanized CD47 mice (n=2) was transferred to a 15 mL tube and centrifuged at 200×g for 10 minutes at 4° C. The plasma and buffy coat were aspirated and then 15 mL of PBS was added and the cells were mixed gently. The mixture was centrifuged again at 200×g for five minutes at 4° C. The supernatant was aspirated and the cells were washed two additional times. Pelleted RBCs were resuspended to a final volume in 10 mL of PBS. The resuspended RBCs were centrifuged a final time at 200×g for 10 minutes at 4° C. The volume of packed RBCs was estimated 0.5 mL and diluted to a concentration of 0.5% with PBS (0.5 mL packed RBC/100 mL PBS). Actual RBC concentration was determined with a Cellometer Auto T4 ($1.5 \times 10^7$/mL; Nexcelom Bioscience).

Figure 4:
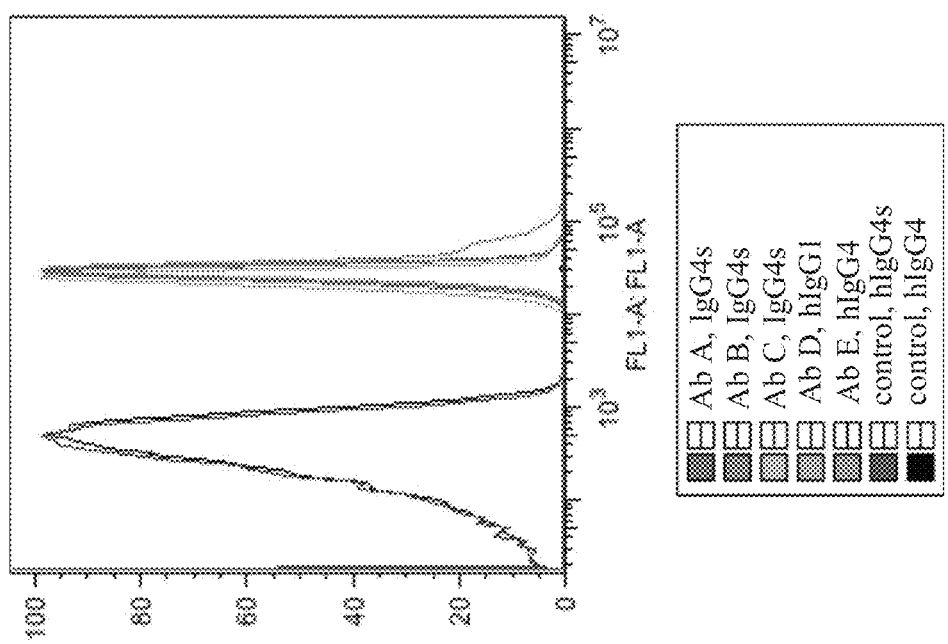
FIG. 4 shows an exemplary histogram of CD47 expression in red blood cells from humanized CD47 mice detected by anti-CD47 antibodies. Ab A, Ab B, Ab C, Ab D and Ab E: anti-CD47 antibodies; hIgG4s: human IgG4 of irrelevant specificity with modified Fc region that has reduced effector function; hIgG4: human IgG4 antibody of irrelevant specificity.

Eighty (80) µL of 0.5% mouse RBCs were added to each well of a 96-well V-bottom plate. Anti-CD47 antibodies were added into each well (20 µL at 33 nM). The plate was gently tapped to mix and incubated on ice for 30 minutes. The plate was then washed twice with staining buffer (PBS with 2% FBS). Secondary antibody Fab-488 (Alexa Fluor 488-conjugated AffiniPure mouse anti-human IgG, F(ab')$_2$ fragment specific, Jackson Immuno Research) was added to each well at a concentration of 10 µg/mL. The plate was incubated again on ice for 30 minutes, followed by washing once with staining buffer. The cells in each well were resuspended in 200 µL of staining buffer and filtered through a 96-well filter plate. The cells in the plate were analyzed using the BD ACCURI™ C6 system (BD Biosciences). Exemplary results are shown in FIG. 4. The mean fluorescence intensity (MFI) above isotype control for each tested antibody is shown in Table 5.

TABLE 5

| Antibody | MFI | Fold above isotype control |
|---|---|---|
| Ab A, hIgG4s | 28898 | 28 |
| Ab B, hIgG4s | 27545 | 246 |
| Ab C, hIgG4s | 24620 | 270 |
| Ab D, hIgG1 | 29882 | 267 |
| Ab E, hIgG4 | 33423 | 298 |
| Control, hIgG4s | 112 | — |
| Control, hIgG4 | 112 | — | hIgG4s: human IgG4 with modified Fc region that has reduced effector function

As shown in FIG. 4, all anti-CD47 antibodies bound to RBCs from humanized CD47 mice. Taken together, this Example demonstrates that (1) non-human animals (e.g., rodents) engineered to contain a humanized CD47 gene as described herein express a humanized CD47 polypeptide on the surface of cells (e.g., RBCs) of the non-human animal, and (2) such cells are useful for screening CD47 modulators (e.g., CD47 antibodies) and determining the pharmacokinetic profiles of such modulators.

Example 3. Hemagglutination of Mouse Red Blood Cells Expressing Humanized CD47 Polypeptide This Example further demonstrates that non-human animals (e.g., rodents) modified to contain a humanized CD47 gene according to Example 1 can be used in various assays (e.g., hemagglutination assay) to screen CD47 modulators (e.g., anti-CD47 antibodies) and determine various characterisitics such as, for example, pharamcokinetics and safety profiles. In this Example, several anti-CD47 antibodies are screened on mouse red blood cells (RBCs) that express a humanized CD47 polypeptide as described herein to determine antibody concentration that promotes hemagglutination.

Briefly, RBCs from wild-type and humanized CD47 mice (n=2) were prepared as described in Example 2. Twenty (20) µL of anti-CD47 antibody (at 5-fold serial dilution) was added into wells 1-12 across a 96-well V-bottom plate followed by the addition of 80 µL of 0.5% mouse RBCs to all wells of the plate. The plates were tapped gently to mix and incubated at room temperature (24-27° C.) for 30 minutes. Agglutination endpoint was observed visually (i.e., RBCs settle to the bottom in negative samples, while RBCs agglutinate in positive samples). Exemplary results are shown in FIG. 5, with boxes to outline the wells that show heme-agglutination.

Figure 5:
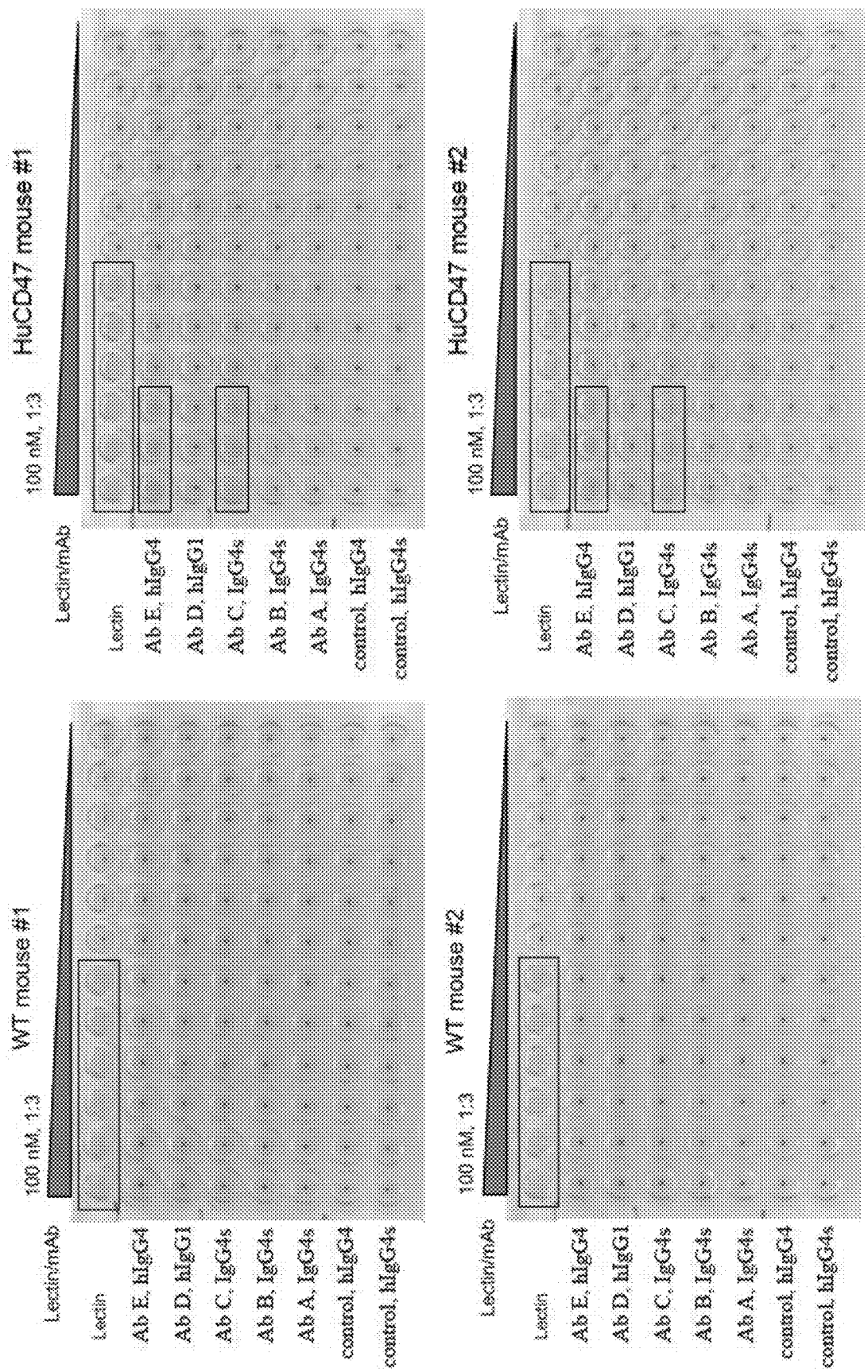
FIG. 5 shows exemplary hemagglutination of mouse red blood cells from wild-type (n=2) and humanized CD47 (n=2) mice by anti-CD47 antibodies. WT: wild-type; HuCD47: humanized CD47; Ab A, Ab B, Ab C, Ab D and Ab E: anti-CD47 antibodies; hIgG4s: human IgG4 of irrelevant specificity with modified Fc region that has reduced effector function; hIgG4: human IgG4 antibody of irrelevant specificity.

As shown in FIG. 5, only lectin caused agglutination in wild-type mice. However, two anti-CD47 antibodies (Ab E and Ab C) in addition to lectin induced agglutination in RBCs from two humanized CD47 rodents made according to Example 1. The concentration at which these two antibodies induced agglutination started from 11 nM. Taken together, this Example demonstrates that non-human animals (e.g., rodents) engineered to contain a humanized CD47 gene as describe herein can be used to assess one or more properties (e.g., hemagglutination) of CD47 modulators (e.g., CD47 antibodies).

Example 4. Pharmacokinetic Clearance of CD47 Modulators in Humanized CD47 Rodents This Example illustrates a method of assessing the pharmacokinetic clearance of CD47 modulators (e.g., anti-CD47 antibodies) in non-human animals (e.g., rodents) modified to contain a humanized CD47 gene according to Example 1. In this Example, wild-type and humanized CD47 rodents (e.g., mice) were administered anti-CD47 antibodies and serum levels of antibodies were determined using an ELISA assay.

Briefly, wild-type (n=5) or mice homozygous for humanized CD47 (n=5; as described above) were administered four anti-CD47 antibodies (Ab F, Ab G, Ab H and Ab I) and an IgG4s isotype control antibody (IgG4s). The genetic background of the mice were 75% CD57BL/6 and 25% 129Sv. Each antibody was tested in five humanized CD47 rodents. All antibodies were administered subcutaneously at a dose of 50 mg/kg. One pre-bleed was collected one day prior to administration of antibody (day 0). Post-injection bleeds were collected at 6 hours, 1 day, 2 days, 3 days, 4 days, 7 days, 10 days and 14 days. Serum fractions from bleeds were separated and subjected to total human antibody analysis using an ELISA immunoassay.

Figure 6:
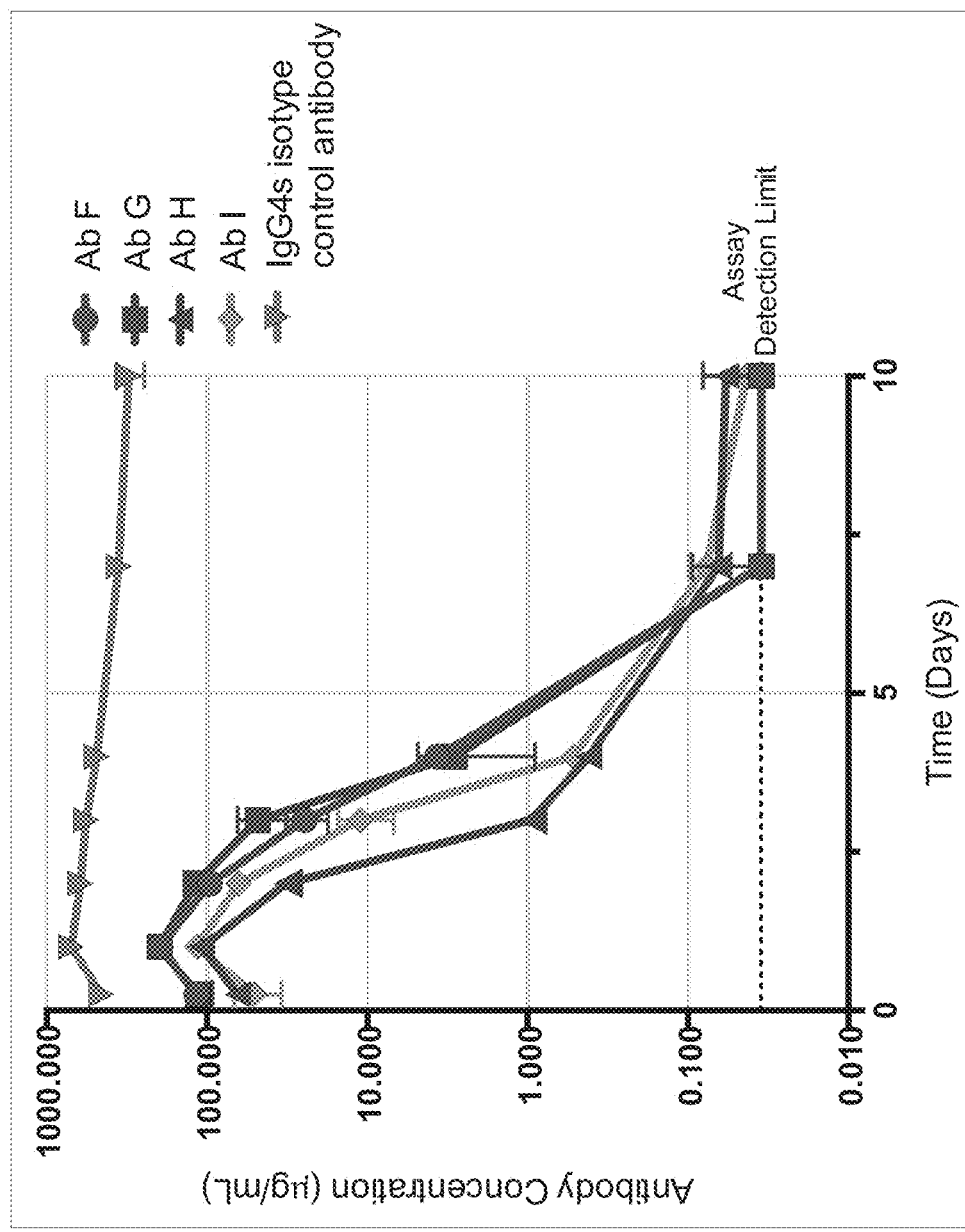
FIG. 6 shows exemplary pharmacokinetic profiles of anti-CD47 antibodies in humanized CD47 mice represented as antibody concentration (in μg/mL, y-axis) over time (in days, x-axis); Ab F, Ab G, Ab H and Ab I: anti-CD47 antibodies; hIgG4s: human IgG4 antibody of irrelevant specificity with modified Fc region that has reduced effector function.

Briefly, a goat anti-human IgG polyclonal antibody (Jackson ImmunoResearch) was coated onto 96-well plates to capture the tested human antibodies in the sera, and then plate bound antibodies were detected using a goat anti-human IgG polyclonal antibody conjugated with horseradish peroxidase (Jackson ImmunoResearch) and TMB substrate (BD Pharmingen). The serum samples were in six-dose serial dilutions and reference standards of the respective antibodies in 12-dose serial dilutions. Drug antibody concentrations in the sera were calculated based on the reference standard curve generated using Graphpad Prism software. Exemplary results are shown in FIG. 6 and Table 6.

The data demonstrated that the antibodies administered to wild-type and humanized mice as described herein were well tolerated. Taken together, this Example demonstrates that non-human animals of the present invention can be used to assess one or more pharmacokinetic properties of a drug targeting CD47 (e.g., an anti-CD47 antibody) such as, for example, circulating drug levels. Moreover, non-human animals described herein can be used to assess the toxicity of a drug targeting CD47 by determining adverse effects after administration.

and 10 days and a urine test was performed as needed (at 6 hours and when urine color deviated from yellow color) to determine red blood cell counts. Exemplary results are shown in FIGS. 7-9.

Figure 7:
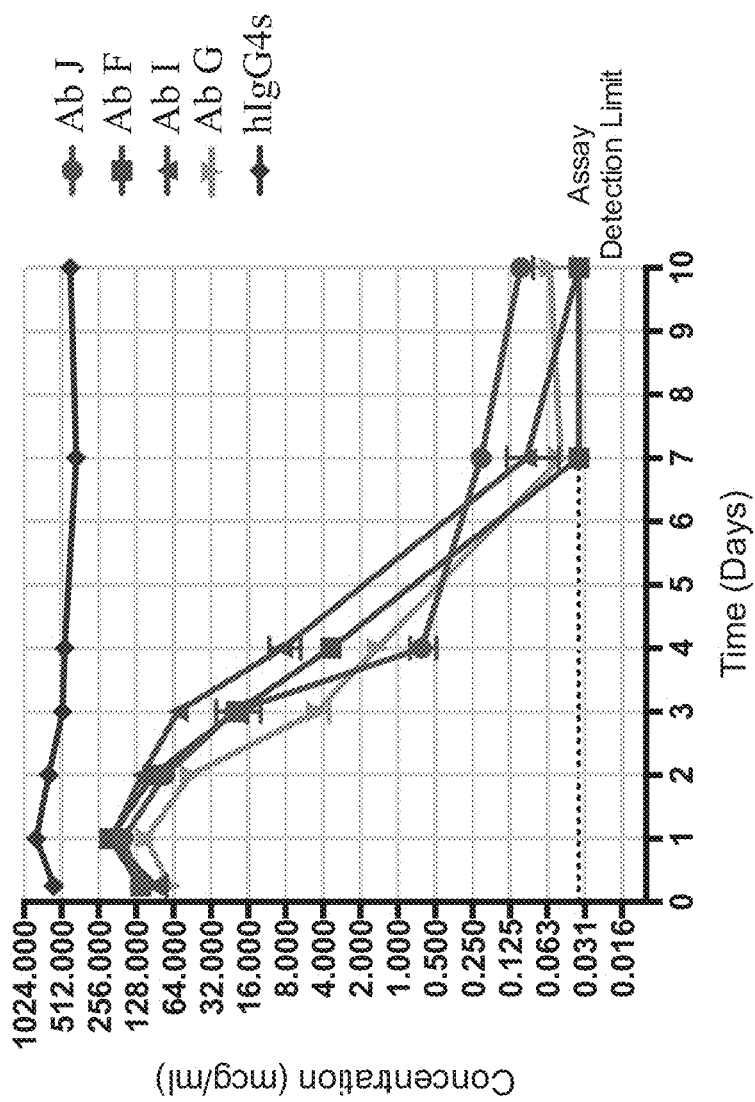
FIG. 7 shows exemplary pharmacokinetic profiles of anti-CD47 antibodies in humanized CD47/SIRPα mice (CD47$^{hu/hu}$SIRPα$^{hu/hu}$) represented as antibody concentration (in mcg/mL, y-axis) over time (in days, x-axis). Ab J, Ab F, Ab G and Ab I: anti-CD47 antibodies; hIgG4s: human IgG4 antibody of irrelevant specificity with modified Fc region that has reduced effector function.
Figure 8:
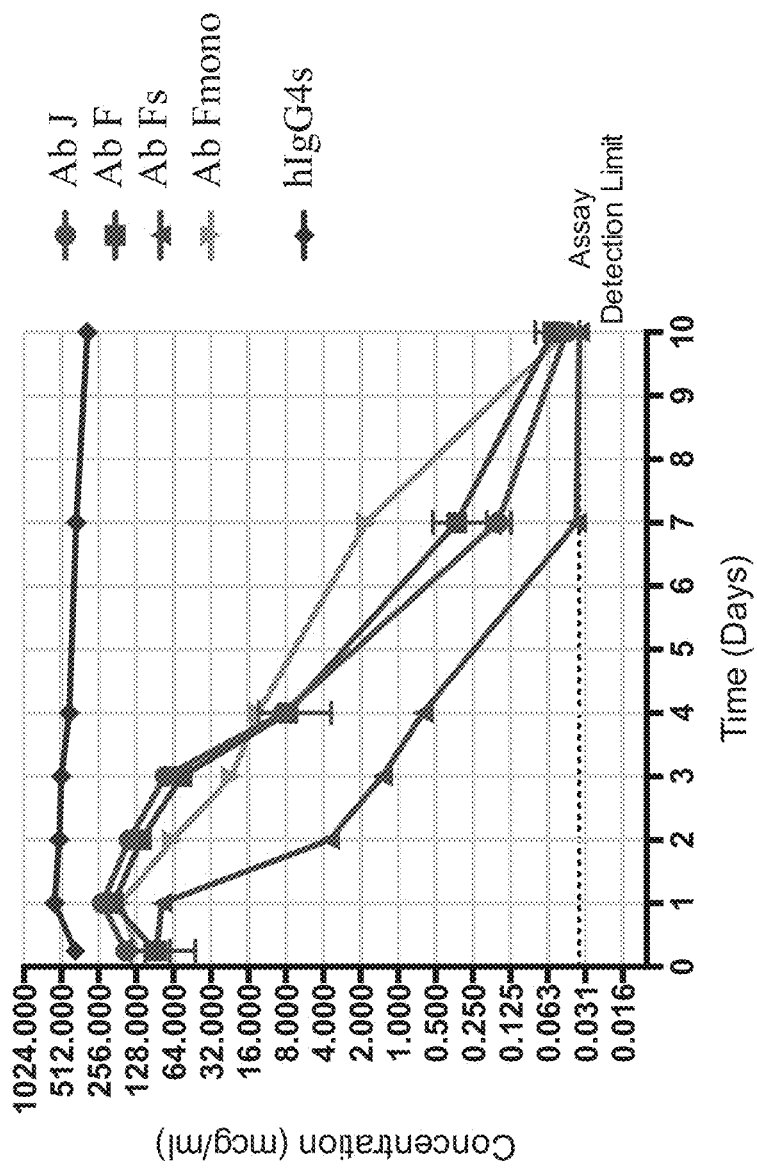
FIG. 8 shows exemplary pharmacokinetic profiles of anti-CD47 antibodies in humanized CD47/SIRPα mice (CD47$^{hu/hu}$SIRPα$^{hu/hu}$) represented as antibody concentration (in mcg/mL, y-axis) over time (in days, x-axis). Ab J, Ab F: anti-CD47 antibodies; Ab Fs: Ab F with modified Fc region that has reduced effector function; Ab Fmono: monovalent version of Ab F; hIgG4s: human IgG4 antibody of irrelevant specificity with modified Fc region that has reduced effector function.
Figure 9:
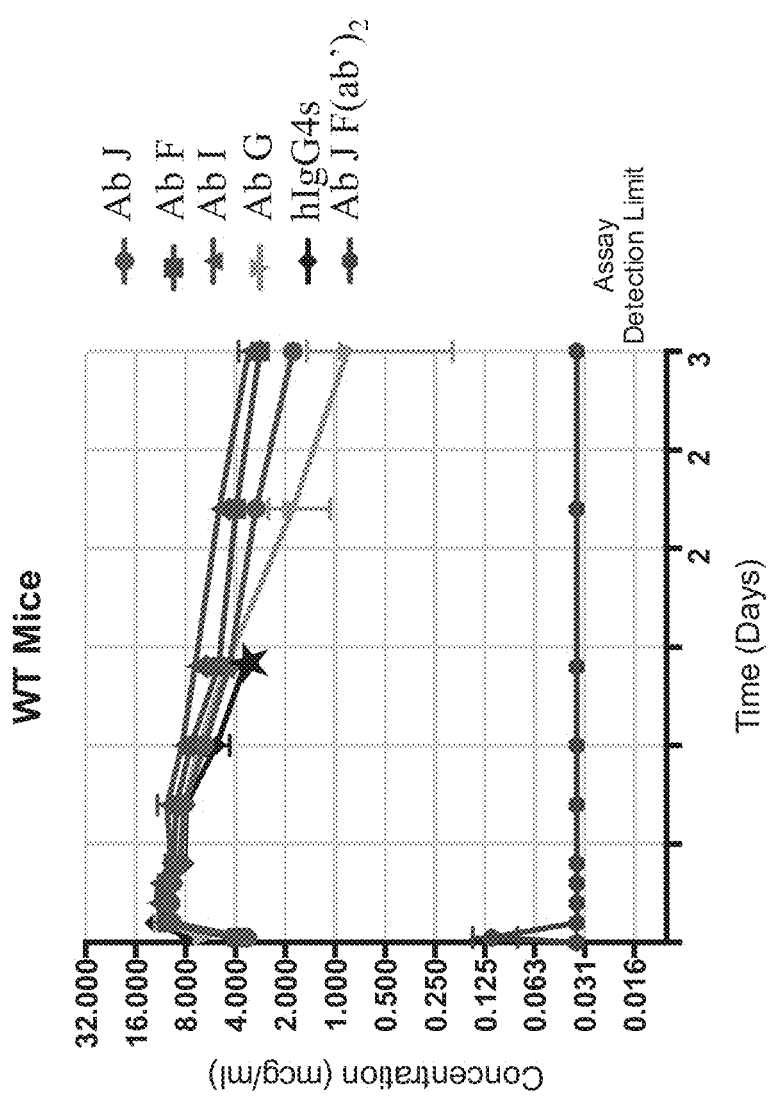
FIG. 9 shows exemplary pharmacokinetic profiles of anti-CD47 antibodies in wild type mice represented as antibody concentration (in mcg/mL, y-axis) over time (in days, x-axis). Mice demonstrating mouse anti-human antibody response (MAHA) were excluded. Ab J, Ab F, Ab I and Ab G: anti-CD47 antibodies; hIgG4s: human IgG4 antibody of irrelevant specificity with modified Fc region that has reduced effector function (star: all points after 15 days were excluded from hIgG4s treatment group due to MAHA); Ab J F(ab')$_2$: F(ab')$_2$ fragment of Ab J.

As shown in FIGS. 7 and 8, all anti-CD47 antibodies demonstrated target-mediated clearance in $CD47^{hu/hu}SIRP\alpha^{hu/hu}$ mice and, in particular, many demonstrated similar pharmacokinetic profiles. Further, a monovalent version of one anti-CD47 antibody (Ab F) demonstrated greater bioavailability than its bivalent equivalent (FIG. 8). The inventors observed similar pharmacokinetic profiles for the antibodies among multiple experiments with humanized CD47 and double humanized animals (i.e., $CD47^{hu/hu}SIRP\alpha^{hu/hu}$ mice).

Ab J had less of an effect on hematocrit levels than other anti-CD47 antibodies tested (Ab F, Ab G, Ab I, etc.) and

TABLE 6

Serum antibody concentrations (μg/mL ± SEM)

| Antibody | 6 hour | Day 1 | Day 2 | Day 3 | Day 4 | Day 7 | Day 10 |
|---|---|---|---|---|---|---|---|
| Ab F | 116.7 ± 14.0 | 196.4 ± 10.6 | 96.0 ± 13.3 | 24.7 ± 7.0 | 3.7 ± 0.42 | <0.35 | <0.35 |
| Ab G | 115.0 ± 22.1 | 198.8 ± 23.4 | 118.4 ± 20.9 | 48.3 ± 16.0 | 2.9 ± 1.97 | <0.35 | <0.35 |
| Ab H | 64.5 ± 3.85 | 108.0 ± 5.13 | 32.0 ± 6.08 | 1.0 ± 0.2 | 0.4 ± 0.03 | 0.06 ± 0.03 | 0.05 ± 0.02 |
| Ab I | 51.1 ± 16.6 | 115.2 ± 14.8 | 63.8 ± 8.3 | 11.1 ± 4.2 | 0.5 ± 0.1 | 0.1 ± 0.02 | <0.35 |
| IgG4s Isotype control | 458.2 ± 34.4 | 702.5 ± 32.3 | 616.6 ± 27.0 | 567.1 ± 39.5 | 488.9 ± 45.0 | 357.0 ± 51.1 | 307.6 ± 61.1 |

Example 5. Pharmacokinetic Profiles of CD47 Modulators in Humanized CD47/SIRPα Rodents This Example illustrates a method of assessing the pharmacokinetic clearance of CD47 modulators (e.g., anti-CD47 antibodies) in non-human animals (e.g., rodents) modified to contain humanized CD47 (according to Example 1) and SIRPα genes. In particular, humanized CD47 rodents described herein were modified to further contain a humanized SIRPα gene that contains an endogenous portion and a human portion, which human portion encodes the extracellular domain of a human SIRPα protein (e.g., amino acids 28-362 of a human SIRPα protein) and which endogenous portion encodes an intracellular domain of an endogenous SIRPα protein (e.g., amino acids encoding transmembrane and intracellular portions of a murine SIRPα protein) as described in PCT/US 14/56,910, filed Sep. 23, 2014, which is incorporated herein by reference. Double humanized CD47/SIRPα mice were made by breeding humanized SIRPα mice to humanized CD47 mice. In this Example, double humanized CD47/SIRPα rodents (e.g., mice) were administered various anti-CD47 antibodies and their corresponding pharmacokinetic profiles were determined.

Briefly, groups of wild type (n=5) and mice homozygous for humanized CD47 and SIRPα genes ($CD47^{hu/hu}$ $SIRP\alpha^{hu/hu}$; n=5 per group) were administered selected anti-CD47 antibodies and an IgG4 isotype control antibody (hIgG4s). The genetic background of the mice were 75% CD57BL/6 and 25% 129Sv. All antibodies were administered in a single subcutaneous dose of 50 mg/kg. One pre-bleed was collected one day prior to administration of antibody (day 0). Post-injection bleeds were collected at 6 hours, 1 day, 2 days, 3 days, 4 days, 7 days and 10 days. Serum fractions from bleeds were separated and subjected to total human antibody analysis using an ELISA immunoassay (described above). Additionally, hematocrit levels were measured at 6 hours, 1 day, 2 days, 3 days, 4 days, 7 days comparable changes in hematocrit levels to control (hIgG4s) in $CD47^{hu/hu}SIRP\alpha^{hu/hu}$ mice. Measurements of hematocrit on days 2-4 showed the largest drop from normal range (~38.5-45.1%), which included groups administered Abs F, G and I. In particular, a monovalent form of Ab F demonstrated a delayed lowering effect on hematocrit as compared to other antibodies tested. The inventors reasoned that differences in hematocrit levels among the various treatment groups could be attributed to a difference in epitope recognized by the various antibodies. Also, mice dosed with selected anti-CD47 antibodies demonstrated positive urine dipstick tests for heme at 6 hours. For example, Ab J and Ab F treatment groups each had one mouse positive for heme on day 1, while all other timepoints were negative. No significant weight loss (>20%) was observed in any treatment group.

Taken together, this Example demonstrates that non-human animals of the present invention provide an in vivo system for assessing the pharmacokinetic properties and/or profiles of one or more drugs targeting CD47 (e.g., one or more anti-CD47 antibodies) such as, for example, circulating drug levels. Moreover, non-human animals as described herein engineered to further contain other humanized genes (e.g., humanized SIRPα) can be used to assess the target-mediated clearance of one or more drugs targeting CD47.

EQUIVALENTS

Having thus described several aspects of at least one embodiment of this invention, it is to be appreciated by those skilled in the art that various alterations, modifications, and improvements will readily occur to those skilled in the art. Such alterations, modifications, and improvements are intended to be part of this disclosure, and are intended to be within the spirit and scope of the invention. Accordingly, the foregoing description and drawing are by way of example only and the invention is described in detail by the claims that follow.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification.

Those skilled in the art will appreciate typical standards of deviation or error attributable to values obtained in assays or other processes described herein.

The publications, websites and other reference materials referenced herein to describe the background of the invention and to provide additional detail regarding its practice are hereby incorporated by reference.

We claim:

1. A method of assessing an effect of an anti-cancer drug candidate targeting human cancer cells, the method comprising:
   providing a genetically modified mouse whose genome comprises a replacement of a genomic fragment comprising exons 2-7 of a mouse CD47 gene at an endogenous mouse CD47 locus with a human genomic fragment comprising exons 2-7 of a human CD47 gene to form a humanized CD47 gene,
   wherein the exons of the humanized CD47 gene consist of exon 1 of the mouse CD47 gene, exons 2-7 of the human CD47 gene, and the remaining exons downstream of exon 7 of the mouse CD47 gene,
   wherein exons 2-7 of the human CD47 gene encode an amino acid sequence that is at least 98% identical with the amino acid sequence as set forth in amino acids 16-292 of SEQ ID NO: 10,
   wherein the humanized CD47 gene is under control of the endogenous mouse CD47 promoter at the endogenous mouse CD47 locus,
   wherein the genetically modified mouse expresses a humanized CD47 protein encoded by the humanized CD47 gene;
   transplanting one or more human cancer cells into the genetically modified mouse;
   administering the anti-cancer drug candidate to the genetically modified mouse; and
   monitoring the one or more human cancer cells in the genetically modified mouse before and after the administration of the anti-cancer drug candidate to determine the effect of the anti-cancer drug candidate on the one or more human cancer cells in the genetically modified mouse.

2. The method of claim 1, wherein the genome of the genetically modified mouse further comprises a replacement of a genomic fragment comprising exons 2, 3 and 4 of a mouse SIRPα gene at an endogenous mouse SIRPα locus with a genomic fragment comprising exons 2, 3 and 4 of a human SIRPα gene to form a humanized SIRPα gene, wherein the humanized SIRPα gene is operably linked to the endogenous mouse SIRPα promoter at the endogenous mouse SIRPα locus, and wherein the humanized SIRPα gene encodes a humanized SIRPα protein comprising an extracellular portion of the human SIRPα protein encoded by the human SIRPα gene and an intracellular portion of the endogenous mouse SIRPα protein encoded by the mouse SIRPα gene.

3. The method of claim 2, wherein the humanized SIRPα gene comprises exons 1, 5, 6, 7 and 8 of the mouse SIRPα gene.

4. The method of claim 1, wherein the anti-cancer drug candidate is an antibody.

5. The method of claim 4, wherein the genetically modified mouse further comprises human immune cells.

6. The method of claim 5, wherein the anti-cancer drug candidate is a bi-specific antibody that binds human CD47 and an antigen on the transplanted human cancer cells.

7. The method of claim 1, wherein exons 2-7 of the human CD47 gene encode the amino acid sequence as set forth in amino acids 16-292 of SEQ ID NO: 10.

\* \* \* \* \*